(12) United States Patent
Koelle et al.

(10) Patent No.: US 7,666,434 B2
(45) Date of Patent: Feb. 23, 2010

(54) RAPID, EFFICIENT PURIFICATION OF HSV-SPECIFIC T-LYMPHOCYTES AND HSV ANTIGENS IDENTIFIED VIA SAME

(75) Inventors: David M. Koelle, Seattle, WA (US); Zhi Liu, Seattle, WA (US); Lawrence Corey, Mercer Island, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 12/233,280

(22) Filed: Sep. 18, 2008

(65) Prior Publication Data

US 2009/0148468 A1 Jun. 11, 2009

Related U.S. Application Data

(62) Division of application No. 11/364,438, filed on Feb. 28, 2006, now Pat. No. 7,431,934, which is a division of application No. 10/623,429, filed on Jul. 18, 2003, now Pat. No. 7,078,041.

(60) Provisional application No. 60/396,791, filed on Jul. 18, 2002.

(51) Int. Cl.
*A61K 39/245* (2006.01)
(52) U.S. Cl. .................. 424/229.1; 424/231.1
(58) Field of Classification Search ........................ None
See application file for complete search history.

(56) References Cited

U.S. PATENT DOCUMENTS

| | | | |
|---|---|---|---|
| 4,859,587 A | 8/1989 | Roizman | |
| 5,538,724 A | 7/1996 | Butcher | |
| 6,375,952 B1 | 4/2002 | Koelle | |
| 6,413,518 B1 | 7/2002 | Koelle | |
| 6,814,969 B2 | 11/2004 | Koelle | |
| 6,821,519 B2 * | 11/2004 | Day et al. | 424/231.1 |
| 6,855,317 B2 | 2/2005 | Koelle | |
| 6,962,709 B2 | 11/2005 | Koelle | |
| 7,037,509 B2 | 5/2006 | Koelle | |
| 2002/0090610 A1 | 7/2002 | Hosken et al. | |

FOREIGN PATENT DOCUMENTS

| | | |
|---|---|---|
| WO | WO 95/06055 | 3/1995 |
| WO | WO 95/16779 A | 6/1995 |
| WO | WO 98/20016 | 5/1998 |
| WO | WO 01/23414 | 4/2001 |

OTHER PUBLICATIONS

De Plaen, E., "Cloning of Genes Coding for Antigens Recognized by Cytolytic T Lymphocytes," Immunology Methods Manual, 1997, 692-718.
Dolan, A., The Genome Sequence of Herpes Simplex Virus Type 2, Journal of Virology, 1998, 72(3):2010-2021.
Fuhlbrigge, Robert C. et al., "Cutaneous lymphocyte antigen is a specialized form of PSGL-1 expressed on skin-homing T cells", Nature, Oct. 30, 1997, vol. 389, pp. 978-981.
Homey, B., "CCL27-CCRIO Interactions Regulate T Cell-mediated Skin Inflammation", Nature Medicine, Feb. 1992, 8(2).
Khan, Naeem et al., "Comparative Analysis of CD8+ T Cell Responses against Human Cytomegalovirus Proteins pp65 and Immediate Early 1 Shows Similarities in Precursor Frequency, Oligoclonality, and Phenotype", The Journal of Infectious Diseases, Mar. 2002, vol. 185, pp. 1025-1034.
Koelle, D.M., "CD8 CTL from Genital Herpes Simplex Lesions; Recognition of Viral Tegument and Immediate Early Proteins and Lysis of Infected Cutaneous Cells", Journal of Immunology, Mar. 2001, 166(6):4049-4058.
Koelle, D.M., "Expression of Cutaneous Lymphocyte-associated Antigen by CD8(+) T Cells Specific for a Skin-trophic Virus", The Journal of Clinical Investigation, Aug. 2002, 110(4):537-548.
Koelle, D.M., "Recognition of Herpes Simplex Virus Type 2 Tegument Proteins by CD4 T Cells . . . . " Jnl. of Virology, 1998, 72(9): 7476-7483.
Koelle, D.M., "The Roles of T Lymphocytes in Host Responses to Herpes Simplex Virus," Herpes, 1995, 2:83-88.
Koelle, D.M., "Clearance of HSV-2 from Recurrent Genital Lesions Correlates with Infiltration of HSV-Specific Cytotoxic T Lymphoctyes," The Journal of Clinical Investigation, 1998, 101(7):1500-1508.
Koelle, D.M., "Preferential Presentation of Herpes Simplex Virus T-Cell Antigen by HLA DQA1*0501/DQB1*0201 in Comparison to HLA DQA1*0201/DQ81*0201," Human Immunology, 1997, 53(2):195-205.
Koelle, D.M., "Direct Recovery of Herpes Simplex Virus (HSV)-Specific T Lymphocyte Clones from Recurrent Genital HSV-2 Lesions," The Journal of Infectious Diseases, 1994, 169:956-61.
Koelle, D.M.., "Antigenic Specificities of Human CD+ T-Cell Clones Recovered from Recurrent Genital Herpes Simples Virus Type 2 Lesions," Journal of Virology, 1994, 68(5):2803-2810.
Kwok, W.W., "Peptide Binding Affinity and pH Variation Establish Functional Thresholds for Activation of HLA-DQ-Restricted T Cell Recognition," Human Immunology, 1999, 60(7):619-626.

(Continued)

*Primary Examiner*—Ali R. Salimi
(74) *Attorney, Agent, or Firm*—Karen S. Canady; canady + lortz LLP

(57) ABSTRACT

Described is a method of identifying an immunologically active antigen of a virus that attacks skin, as well as a method of enriching a population of lymphocytes for T lymphocytes that are specific to a virus that attacks skin. Also provided are HSV antigens and epitopes that are useful for the prevention and treatment of HSV infection that have been identified via the methods of the invention. T-cells having specificity for antigens of the invention have demonstrated cytotoxic activity against cells loaded with virally-encoded peptide epitopes, and in many cases, against cells infected with HSV. The identification of immunogenic antigens responsible for T-cell specificity provides improved anti-viral therapeutic and prophylactic strategies. Compositions containing antigens or polynucleotides encoding antigens of the invention provide effectively targeted vaccines for prevention and treatment of HSV infection.

19 Claims, 22 Drawing Sheets

OTHER PUBLICATIONS

Marshall, Natalie A., "Rapid reconstitution of Epstein-Barr virus-specific T lymphocytes following allogeneic stem cell transplantation", Immunology, Oct. 15, 2000, Blood, vol. 96, No. 8, pp. 2814-2821.

Nozawa, Naoki, "Identification and Characterization of the UL7 Gene Product of Herpes Simplex Virus Type 2", Virus Genes, Jun. 2002, 24(3):257-266.

Paoletti, "Applications of Pox Virus Vectors to Vaccination: An Update," Proceedings of the National Academy of Science USA, Oct. 1996, 93:11349-11353.

Pober, Jordan S. et al., "Human Endothelial Cell Presentation of Antigen and the Homing of Memory/Effector T Cells to Skin", Annals New York Academy of Sciences, 2001, vol. 941, pp. 12-25.

Posavad, C.M., "High Frequency of CD8+Cytotoxic T-Lymphoctye Precursors Specific for Herpes Simplex Viruses in Persons with Genital Herpes," Journal of Virology, 1996, 70(11):8165-8168.

Reichstetter, S., "MCH-Peptide Ligand Interactions Establish a Functional Threshold for Antigen-Specific T Cell Recognition," Human Immunology, 1999, 60(7):608-618.

Roizman, B., "Herpes Simplex Viruses and Their Replication", Fundamental Virology, $2^{nd}$ Edition, ed. Fields et al, Raven Press, 1991, New York, pp. 849-895.

Stanberry, "Glycoprotein-D-Adjuvant Vaccine to Prevent Genital Herpes," N. Engl. J. Med., 2002, 347(21):1652-1661.

Stanberry, Lawrence R., "Prospects for Control of Herpes Simplex Virus Disease through Immunization", Clinical Infectious Diseases, Mar. 2000, vol. 30, pp. 549-566.

Tigges, M.A., "Human CD8+Herpes Simplex Virus-Specific Cytotoxic T-Lymphocyte Clones Recognize Diverse Virion Protein Antigens," Journal of Virology, 1992, 66(3):1622-1634.

Williams, "Characterization of a Herpes Simplex Virus Type 2 Deoxyuridine . . . " Virology, 1987, 156:282-292.

Williams, "Deoxyuridine Triphosphate Nucleotidohydrolase Induced by Herpes Simplex Virus Type 1," Jnl. of Biological Chemistry, 1984, 259(16): 10080-10084.

* cited by examiner

RAPID, EFFICIENT PURIFICATION OF HSV-SPECIFIC T-LYMPHOCYTES AND HSV ANTIGENS IDENTIFIED VIA SAME

This application is a divisional of U.S. patent application Ser. No. 11/364,438, filed Feb. 28, 2006, now U.S. Pat. No. 7,431,934, issued Oct. 7, 2008, which is a divisional of U.S. patent application Ser. No. 10/623,429, filed Jul. 18, 2003, now U.S. Pat. No. 7,078,041, issued Jul. 18, 2006, which claims the benefit of U.S. provisional patent application No. 60/396,791, filed Jul. 18, 2002, the entire contents of each of which are incorporated herein by reference.

STATEMENT REGARDING FEDERALLY SPONSORED RESEARCH

The invention disclosed herein was made with Government support under Grant Nos. AI50132 and AI30731, awarded by the National Institutes of Health. The government has certain rights in this invention.

TECHNICAL FIELD OF THE INVENTION

The invention relates to molecules, compositions and methods that can be used for the treatment and prevention of viral infection. More particularly, the invention identifies epitopes of HSV proteins that can be used for methods, molecules and compositions having the antigenic specificity of HSV-specific T cells, and in particular, of CLA+, CD8+ T cells. In addition, the invention relates to a method for purifying virus-specific T lymphocytes and for identifying further epitopes useful in the development of diagnostic and therapeutic agents for detecting, preventing and treating viral infection.

BACKGROUND OF THE INVENTION

HSV-2 infects about 22% of persons in the US. The level of infection is increasing. HSV-2 infection is associated with an increased risk of acquisition of HIV-1 infection, the main cause of AIDS. HSV-2 infection is associated with death or morbidity of infants who are infected in the neonatal period by transit through areas of HSV-2 infection in the cervix or vagina. HSV-2 also causes painful recurrent ulcerations in the genital or rectal areas of some infected persons and as such leads to a very high level of health care utilization and pharmacy costs. There is no licensed preventative vaccine. There are positive data from a phase III clinical trial showing about 40% efficacy to prevent HSV-2 infection, and about 70% efficacy to prevent HSV-2-induced clinical disease (Stanberry, 2002, N. Engl. J. Med. 347(21):1652-1661. However there was only positive efficacy data in the subset of study participants who were female and who were uninfected with HSV type 1 at the time the study started. A very large phase III confirmatory clinical trial in HSV-1 uninfected women only is currently being planned and will take several years.

Once HSV-2 infection occurs, the virus causes latent infection of the sensory neurons in the ganglia that enervate the area of skin or mucosal infection. Periodically, the virus reactivates from latency in the neurons, travels down their axons, and causes a productive infection of the skin or mucosa in the areas that are enervated by the neuron. Current therapy can decrease this lytic replication in the skin or mucosa. However, current therapy does not remove latent virus from neurons. If the antiviral therapy is not being taken at the time the virus reactivates in the neuron, it will not prevent replication of the virus in the skin or mucosa, and thus is not able to reduce new symptoms or block the chance of shedding of live HSV-2 into the environment and thus transmission of HSV-2. Current therapy can be taken on a continual basis (suppressive therapy), which reduces symptomatic outbreaks and HSV-2 shedding, but as soon as it is stopped, the same underlying pattern of recurrent symptoms and lesions returns.

There remains a need to identify specific epitopes capable of eliciting an effective immune response to HSV infection. Such information can lead to the identification of more effective immunogenic antigens useful for the prevention and treatment of HSV infection.

SUMMARY OF THE INVENTION

The invention provides HSV antigens, polypeptides comprising HSV antigens, polynucleotides encoding the polypeptides, vectors, and recombinant viruses containing the polynucleotides, antigen-presenting cells (APCs) presenting the polypeptides, immune cells directed against HSV, and pharmaceutical compositions. The pharmaceutical compositions can be used both prophylactically and therapeutically. The invention additionally provides methods, including methods for preventing and treating HSV infection, for killing HSV-infected cells, for inhibiting viral replication, for enhancing secretion of antiviral and/or immunomodulatory lymphokines, and for enhancing production of HSV-specific antibody. For preventing and treating HSV infection, for enhancing secretion of antiviral and/or immunomodulatory lymphokines, for enhancing production of HSV-specific antibody, and generally for stimulating and/or augmenting HSV-specific immunity, the method comprises administering to a subject a polypeptide, polynucleotide, recombinant virus, APC, immune cell or composition of the invention. The methods for killing HSV-infected cells and for inhibiting viral replication comprise contacting an HSV-infected cell with an immune cell of the invention. The immune cell of the invention is one that has been stimulated by an antigen of the invention or by an APC that presents an antigen of the invention. A method for producing such immune cells is also provided by the invention. The method comprises contacting an immune cell with an APC, preferably a dendritic cell, that has been modified to present an antigen of the invention. In a preferred embodiment, the immune cell is a T cell such as a CD4+ or CD8+ T cell.

The invention provides a method of identifying an immunologically active antigen of a virus that attacks skin. The method comprises obtaining peripheral blood mononuclear cells (PBMC) from a subject infected with the virus that attacks skin, and isolating lymphocytes from the PBMC that express cutaneous lymphocyte-associated antigen (CLA). The method further comprises identifying CLA-positive lymphocytes that selectively kill cells infected with the virus that attacks skin, and determining the identity of the antigen present in the identified lymphocyte. Accordingly, die antigen whose identity is determined in this manner is the immunologically active antigen of the virus that attacks skin. The invention additionally provides antigens and epitopes of viruses that attack skin, which antigens and epitopes are useful for eliciting an immune response to the virus. These compositions can be used to prevent, treat and diagnose viral infection.

Examples of viruses that attack skin include herpes simplex virus (HSV), including HSV-1 and HSV-2, human papilloma virus (HPV), and varicella zoster virus (VZV). Examples of HSV antigens that have been identified by the method of the invention include UL7, UL25, UL26, UL6, US6 or US8 of HSV-2. In addition, immunologically active epitopes within these HSV-2 proteins have been identified, namely, 174-186 or 50-192 of UL7, 405-413 or 322-417 of UL25, 475-483 or 404-627 of UL26, 354-362 or 254-722 of UL46, 365-373 or 342-393 of US6, and 518-526 or 503-545 of US8.

The invention further provides a method of enriching a population of lymphocytes for T lymphocytes that are specific to a virus that attacks skin. The method comprises obtaining peripheral blood mononuclear cells (PBMC) from a subject infected with the virus that attacks skin, and isolating lymphocytes from the PBMC that express cutaneous lymphocyte-associated antigen (CLA). The method further comprises isolating CLA-positive lymphocytes that selectively kill cells infected with the virus that attacks skin. The CLA-positive lymphocytes isolated by selective cell killing are the T lymphocytes specific to the virus that attacks skin.

The invention additionally provides pharmaceutical compositions comprising the HSV antigens and epitopes identified herein. Also provided is an isolated polynucleotide that encodes a polypeptide of the invention, and a composition comprising the polynucleotide. The invention additionally provides a recombinant virus genetically modified to express a polynucleotide of the invention, and a composition comprising the recombinant virus. In preferred embodiments, the virus is a vaccinia virus, canary pox virus, HSV, lentivirus, retrovirus or adenovirus. A composition of the invention can be a pharmaceutical composition. The composition can optionally comprise a pharmaceutically acceptable carrier and/or an adjuvant.

BRIEF DESCRIPTION OF THE FIGURES

FIG. 1A shows an analysis of PBMC from a person with HSV-2 infection. Each dot is one lymphocyte. The X-axis shows the level of expression of CD8α, as measured with a fluorescent mAb which is specific for CD8α. The Y-axis shows the level of binding by a fluorescently labeled tetramer of the HLA B*0702 molecule bound to a peptide from HSV-2 with the sequence of protein VP22, amino acids 49-57. This reagent, called tetramer B7-RPR only binds to HSV-2-specific CD8 T-cells. The cells in the upper right quadrant are HSV-2-specific CD8 T-cells. The cells in the lower right quadrant are CD8 T-cells with other specificities. Panel B1 of FIG. 1B shows an analysis of the cell surface expression of CLA, as detected with a mAb specific for CLA, which is limited to the cells in the upper right quadrant of FIG. 1A. Panel B2 of FIG. 1B is similar except that the cells in the lower right quadrant of FIG. 1A are analyzed. Panels C1 and C2 of FIG. 1C are similar except that the expression of CD28 is analyzed. Overall, the data show that HSV-2-specific CD8 T-cells identified by tetramer B7-RPR express high levels of CLA and CD28.

FIG. 2A shows the forward scatter and side scatter characteristics of the PBMC. Each dot is one cell. Box R1 indicates the cells with the physical characteristics of lymphocytes, based on their forward scatter (an index of size) and side scatter (an index of granularity). FIG. 2B shows the expression of CD8α, and CD28 amongst the cells in the R1 box in FIG. 2A. Only the cells in box R1 are shown in the analysis in FIG. 2B. The cells in region R2 have high expression of CD8α and CD28. FIG. 2C shows the expression of CLA. Only the cells in region R1 and region R2 are shown in the analysis in FIG. 2C. The horizontal bar M1 and the corresponding region R3 indicate the cells that have high expression of CLA. The lymphocytes expressing high levels of CD8α and CD28 and CLA (R1 and R2 and R3) were selected using a Becton Dickinson FacsVantage™ cell sorter and used for subsequent antigen discovery.

FIG. 4A shows the cytotoxicity of the sorted CD8-high, CD28-high, CLA-low cells. FIG. 4B shows the cytotoxicity of the sorted CD8-high, CD28-high, CLA-high cells, which are able to kill autologous HSV-2-infected cells. The results show that cells that were selected on the basis of expression of CD8, CD28, and CLA specifically recognize and kill HSV-2 infected autologous cells, while cells that were selected on the basis of the expression of CD8α, CD28, but low levels of CLA do not recognize and kill HSV-2 infected autologous cells.

FIG. 5A: Killing by HSV-2-specific CD8 T-cell clone 10569.1F3. Peptide is DRLDNRLQL (SEQ ID NO: 1), predicted to be encoded by HSV-2 ORF UL25, amino acids 405-413. FIG. 5B: Killing by HSV-2-specific CD8 T-cell clone 6376.1E4. Peptide is GPHETITAL (SEQ ID NO: 2), predicted to be encoded by HSV-2 ORF UL26, amino acids 475-483. FIG. 5C: Killing by HSV-2-specific CD8 T-cell clone 5491.E2. Peptide is ASDSLNNEY (SEQ ID NO: 4), predicted to be encoded by HSV-2 ORF UL46, amino acids 354-362. FIG. 5D: Killing by HSV-2-specific CD8 T-cell clone 10569.2B9. Peptide is RRAQMAPKR (SEQ ID NO: 5), predicted to be encoded by HSV-2 ORF US6, amino acids 365-373.

FIG. 6A: Lesion-derived clone 5491.2000.48, specific for HSV-2 VP22 amino acids 49-57, stained with tetramer B7-RPR, comprised of HLA B*0702 and HSV-2 VP22 amino acids 49-57, and anti-CD8α. FIG. 6B: Similar analysis of clone negative control clone 5491.2000.48, specific for ICP0 amino acids 743-751. FIG. 6C: Similar analysis of PBMC from HSV-2-infected, B*0702-bearing subject 7282 stimulated for 12 days with VP22 amino acids 49-57. FIG. 6D: Cytotoxicity of a typical clone, 7282.12, derived after sorting the cells in panel c for high expression of CD8α and tetramer binding. Targets were autologous EBV-LCL either untreated (♦), infected with HSV-2 (■), or pulsed with peptide VP22 49-57 (●). Among 21 resultant clones, 18 (86%) were cytotoxic towards HLA B7-expressing EBV-LCL pulsed with peptide VP22 49-57 or infected with HSV-2, and each cytotoxic clone stained positive with tetramer B7-RPR. FIG. 6E: Clone 5491.2000.81 stains with tetramer B7-APA. FIG. 6F: Negative control clone 5491.2000.48 does not stain with tetramer B7-APA. FIG. 6G: Clone 5491.2000.81 kills autologous EBV-LCL infected with HSV-2 (▲) but not HSV-1 (♦) or uninfected (■). FIG. 6H: Lysis of autologous EBV-LCL pulsed with peptide ICP0 743-751 by clone 5941.2000.81. FIG. 6I: Proportion of CD8α-high cells in whole PBMC of HLA B*0702-expressing subjects which bind tetramer B7-RPR, specific for HSV-2 protein VP22, amino acids 49-57. Integers above bars are number of replicate aliquots of PBMC stained in each experiment. Bar heights are mean values. Error bars are standard deviations of the mean. For subjects 6376, 4196, and 5491, experiments were conducted on aliquots of PBMC thawed on two days (A and B) but obtained at a single phlebotomy. The inter-assay and intra-assay variabilities using replicate aliquots of cells were <10%. Controls (con) 1-3 are HSV-2 infected but B10702-negative; controls 4-6 are HSV-uninfected and B*0702-positive.

FIG. 7A: Tetramer B7-RPR and anti-CD8α staining of lymphocytes in PBMC from six HSV-2-infected, B*0702 subjects. Subject numbers at top are in same order as FIG. 6E and the percentages of CD8α-high lymphocytes staining with the tetramers are given in FIG. 6E. Quadrant lines are cutoffs for CD8α-high and tetramer binding. FIG. 7B: Expression of CLA by CD8α-high lymphocytes that stain with tetramer B7-RPR. FIG. 7C: Expression of CLA by CD8α-high lymphocytes that do not stain with tetramer B7-RPR. The percentage of CLA positive cells is indicated for each histogram. FIG. 7D: Staining of PBMC from HLA A*0201 subject with tetramers A2-GLA specific for T-cells reactive with HSV-2 VP13/14 551-559 (left), A2-VLE or A2-NVP specific for T-cells reactive with CMV 1E-1 316-324 or pp 65 595-603, respectively (middle), or A2-CLG or A2-GLC specific for T-cells reactive with EBV LMP2 246-434 or BMLF-1 280-288, respectively (right), and anti-CD8α. For subject 10433, the gates for tetramer-high and tetramer-low CD8+ cells are shown. For CMV and EBV, the dot-plots correspond to lines 5, 1, 12, and 10 of Table 4. The proportion of CD8α-high cells staining with tetramer, and the quadrants indicating cutoffs for CD8α and tetramer binding, are shown. FIG. 7E: Expression of CLA by CD8α-high lymphocytes that stain with herpesvirus tetramers. FIG. 7F: Expression of CLA by CD8α-high lymphocytes not staining with the indicated tetramers B8-RPR. Percentage of CLA positive cells are indicated.

FIG. 8A: PBMC from B*0702-bearing, HSV-2 infected subject 5491 (left two panels) or two different A*0201-bearing subjects (right two panels) stimulated for 13 days with HSV-2 VP22 49-57 (left), HSV-2 ICP0 743-751 (next), or EBV BMLF 280-288 (right two panels). Dot-plots display binding of the relevant tetramers and anti-CD8α. Quadrant lines are cutoffs for CD8α-high and tetramer binding. The percentages of CD8α-high cells that are tetramer-positive are indicated. FIG. 8B: Expression of CLA by CD8α-high lymphocytes that stain with HSV-2 or EBV tetramers. FIG. 8C: Expression of CLA by CD8α-high lymphocytes that do not stain with tetramer. Percentage of CLA positive cells as in FIG. 7.

FIG. 9A: PBMC from donor 4196 were gated for lymphocyte size and scatter, high CD8α expression, and binding of tetramer B7-RPR specific for VP22 49-57. Expression of CD28, CD62L, and CCR7 is displayed in the indicated histograms. FIG. 9B: Similar data for CD8α-high lymphocytes from the same donor which did not bind tetramer B7-RPR.

FIG. 10A: Frozen section of HSV-2 lesion from subject 5491 stained with anti-E-selectin and haematoxylin Original magnification 20×. FIG. 10B: Normal skin from subject 5491 stained with anti-E-selectin and haematoxylin. The epidermis is at upper right. Original magnification 20×. FIG. 10C: HSV-2 lesion stained with anti-CLA. Hair follicle and epidermis at lower left. Original magnification 4×. FIG. 10D: Normal skin stained with anti-CLA. Original magnification 20×. Epidermis at right. FIG. 10E: HSV-2 lesion stained with hematoxylin and eosin. FIG. 10F: Normal skin stained with hematoxylin and eosin. FIG. 10G: Lymphocytes expanded for 11 days from the biopsy stained with HSV-2 tetramer B7-RPR (left) or B7-APA (right) and anti-CD8α. Quadrant lines are cutoffs for CD8α-high and tetramer binding. The percentages of CD8α-high cells that are tetramer-positive are indicated. FIG. 10H: Expression of CLA by CD8α-high, tetramer-binding cells for tetramer B7-RPR-PE (left) or B7-APA-PE (right). FIG. 10I: Expression of CLA by CD8α-high, tetramer non-binding cells. Percentages of CLA positive cells as in FIG. 7.

FIG. 12A: Binding of anti-CD8α antibody to lymphocytes (gated on forward and side scatter) from subject 6376. FIG. 12B: CD8α+ cells from panel A were analyzed for expression of CLA. FIG. 12C: CLA+ cells from panel B were analyzed for binding of allophycocyanin (APC)-conjugated tetramer B7-RPR FIG. 12D: CLA-cells from panel B were analyzed for binding of tetramer B7-RPR. Note the Y-axis scales differ for each panel. The percentages of cells recorded as positive are shown in each panel.

FIG. 14A: Cytotoxicity of VP11/12 gene UL46) and VP13/14 (gene UL47)-specific CD8 CTL clones against autologous LCL infected with parental HSV-2 HG52, UL47 deletion virus (del47), virus with UL47 re-inserted (47rev), wild-type vaccine (vWT), and vaccinia expressing UL47 (vUL47). FIG. 14B: Proliferation of VP16 (gene UL48)-specific CD4+ T-cell clone 1A.B.25.1 to inactivated virus antigen prepared from the indicated strains and autologous PBMC as APC. Values are mean of triplicate CPM 3H thymidine incorporation minus mean CPM for mock antigen (221 cpm).

FIG. 15A: Cytotoxicity of against autologous EBV-LCL in the presence or absence of HSV-2 infection and blocking anti-HLA mAb. FIG. 15B: Comparison of IFN-γ secretion by clone 3D8 and typical class I-restricted clones 1F3 (B*1402/UL25 405-413) and 2B9 (B*27052/gD2 365-373), each from subject 2, after co-cultivation with autologous EBV-LCL treated as indicated, and effect of anti-HLA class I mAb. FIG. 15C: Cell-surface expression of lymphocyte markers.

DETAILED DESCRIPTION OF THE INTENTION

Figure 1B:
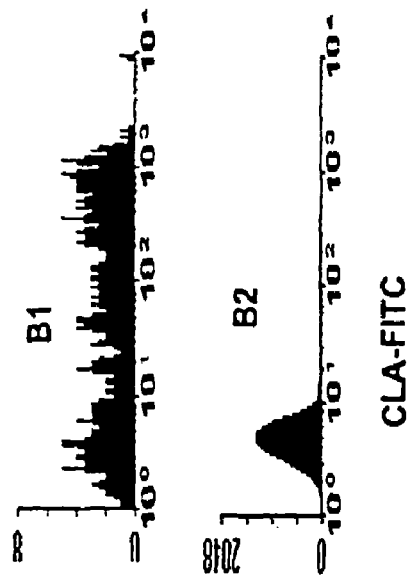
FIGS. 1A-1C. Representative data showing that HSV-2-specific CD8 T-cells express high levels of CLA and CD28.
Figure 1A:
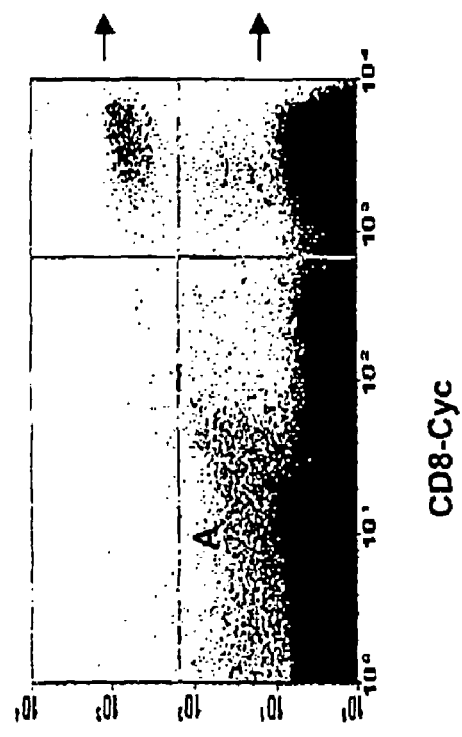
Figure 1C:
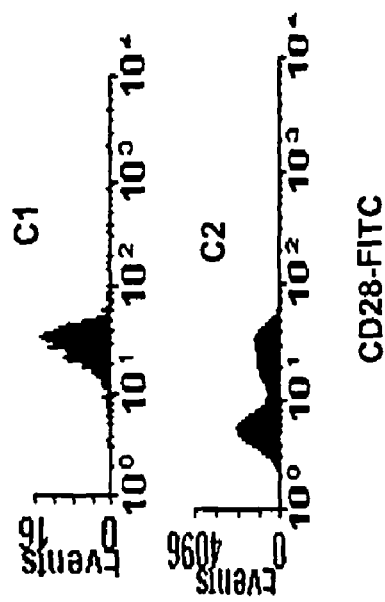

The invention is based on discovery of a means by which HSV-2-specific lymphocytes in the blood become programmed to traffic to the skin during episodes of recurrent HSV-2 infection. Specifically, these T-cells have been found to express the glycoprotein epitope termed CLA (cutaneous lymphocyte-associated antigen). The invention makes use of this discovery to provide a method to purity HSV-2-specific T-lymphocytes from the blood that are HSV-2-specific based on sorting blood cells by a set of criteria that include the surface expression of CLA, CD8, and the co-stimulatory molecule CD28. This provides a method of rapid and efficient isolation of HSV-2-specific CD8 T-cells from blood. After obtaining these rare cells from the blood, a method of genetic expression cloning can be applied to determine the exact HSV-2 open reading frames (ORFs; antigens), and the exact short peptide sequences (epitopes) encoded by the HSV-2 genome, that are recognized by these HSV-2-specific CD8 T-cells.

The invention provides HSV antigens and epitopes that are useful for the prevention and treatment of HSV infection. Disclosed herein are antigens and/or their constituent epitopes confirmed to be recognized by T-cells derived from herpetic lesions. In some embodiments, T-cells having specificity for antigens of the invention have demonstrated cytotoxic activity against virally infected cells. The identification of immunogenic antigens responsible for T-cell specificity facilitates the development of improved anti-viral therapeutic and prophylactic strategies. Compositions containing antigens or polynucleotides encoding antigens of the invention provide effectively targeted vaccines for prevention and treatment of HSV infection. Available data indicate that boosting of HSV-2-specific immune responses can prevent infection or reduce the symptoms of HSV-2 in persons who are already infected. These cells can have one or more antiviral effect, including the ability to kill HSV-2-infected cells thereby reducing the output of infectious HSV-2, and secrete proteins with antiviral properties.

DEFINITIONS

All scientific and technical terms used in this application have meanings commonly used in the art unless otherwise specified. As used in this application, the following words or phrases have the meanings specified.

As used herein, "polypeptide" includes proteins, fragments of proteins, and peptides, whether isolated from natural sources, produced by recombinant techniques or chemically synthesized. Polypeptides of the invention typically comprise at least about 6 amino acids, and can be at least about 15 amino acids. Typically, optimal immunological potency is obtained with lengths of 8-10 amino acids.

As used herein, "HSV polypeptide" includes HSV-1 and HSV-2, unless otherwise indicated. References to amino acids of HSV proteins or polypeptides are based on the genomic sequence information regarding HSV-2 (strain HG52) as described in A. Dolan et al., 1998, J. Virol. 72(3): 2010-2021.

As used herein, "substitutional variant" refers to a molecule having one or more amino acid substitutions or deletions in the indicated amino acid sequence, yet retaining the ability to be "immunologically active", or specifically recognized by an immune cell. The amino acid sequence of a substitutional variant is preferably at least 80% identical to the native amino acid sequence, or more preferably, at least 90% identical to the native amino acid sequence. Typically, the substitution is a conservative substitution.

One method for determining whether a molecule is "immunologically active", or can be specifically recognized by an immune cell, is the cytotoxicity assay described in D. M. Koelle et al., 1997, Human Immunol. 53:195-205. Other methods for determining whether a molecule can be specifically recognized by an immune cell are described in the examples provided hereinbelow, including the ability to stimulate secretion of interferon-gamma or the ability to lyse cells presenting the molecule. An immune cell will specifically recognize a molecule when, for example, stimulation with the molecule results in secretion of greater interferon-gamma than stimulation with control molecules. For example, the molecule may stimulate greater than 5 pg/ml, or preferably greater than 10 pg/ml, interferon-gamma secretion, whereas a control molecule will stimulate less than 5 pg/ml interferon-gamma.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

The term "nucleic acid" or "polynucleotide" refers to a deoxyribonucleotide or ribonucleotide polymer in either single- or double-stranded form, and unless otherwise limited, encompasses known analogs of natural nucleotides that hybridize to nucleic acids in a manner similar to naturally occurring nucleotides.

As used herein, "antigen-presenting cell" or "APC" means a cell capable of handling and presenting antigen to a lymphocyte. Examples of APCs include, but are not limited to, macrophages, Langerhans-dendritic cells, follicular dendritic cells, B cells, monocytes, fibroblasts and fibrocytes. Dendritic cells are a preferred type of antigen presenting cell. Dendritic cells are found in many non-lymphoid tissues but can migrate via the afferent lymph or the blood stream to the T-dependent areas of lymphoid organs. In non-lymphoid organs, dendritic cells include Langerhans cells and interstitial dendritic cells. In the lymph and blood, they include afferent lymph veiled cells and blood dendritic cells, respectively. In lymphoid organs, they include lymphoid dendritic cells and interdigitating cells.

As used herein, "modified" to present an epitope refers to antigen-presenting cells (APCs) that have been manipulated to present an epitope by natural or recombinant methods. For example, the APCs can be modified by exposure to the isolated antigen, alone or as part of a mixture, peptide loading, or by genetically modifying the APC to express a polypeptide that includes one or more epitopes.

As used herein, "pharmaceutically acceptable salt" refers to a salt that retains the desired biological activity of the parent compound and does not impart any undesired toxicological effects. Examples of such salts include, but are not limited to, (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalenedisulfonic acids, polygalacturonic acid; (b) salts with polyvalent metal cations such as zinc, calcium, bismuth, barium, magnesium, aluminum, copper, cobalt, nickel, cadmium, and the like; or (c) salts formed with an organic cation formed from N,N'-dibenzylethylenediamine or ethylenediamine; or (d) combinations of (a) and (b) or (c), e.g., a zinc tannate salt; and the like. The preferred acid addition salts are the trifluoroacetate salt and the acetate salt.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline.

Compositions comprising such carriers are formulated by well known conventional methods (see, for example, *Remington's Pharmaceutical Sciences,* 18th edition, A. Gennaro, ed., Mack Publishing Co., Easton, Pa., 1990).

As used herein, "adjuvant" includes those adjuvants commonly used in the art to facilitate the stimulation of an immune response. Examples of adjuvants include, but are not limited to, helper peptide; aluminum salts such as aluminum hydroxide gel (alum) or aluminum phosphate; Freund's Incomplete Adjuvant and Complete Adjuvant (Difco Laboratories, Detroit, Mich.); Merck Adjuvant 65 (Merck and Company, Inc., Rahway, N.J.); AS-2 (Smith-Kline Beecham); QS-21 (Aquilla); MPL or 3d-MPL (Corixa Corporation, Hamilton, Mont.); LEIF; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A; muramyl tripeptide phosphatidyl ethanolamine or an immunostimulating complex, including cytokines (e.g., GM-CSF or interleukin-2, -7 or -12) and immunostimulatory DNA sequences. In some embodiments, such as with the use of a polynucleotide vaccine, an adjuvant such as a helper peptide or cytokine can be provided via a polynucleotide encoding the adjuvant.

As used herein, "a" or "an" means at least one, unless clearly indicated otherwise.

As used herein, to "prevent" or "protect against" a condition or disease means to hinder, reduce or delay the onset or progression of the condition or disease.

Overview

HSV-2 encodes about 85 proteins using DNA which contains about 85 genes. The genes have names such as UL4, standing for unique long gene 4, or US4, standing for unique short gene 4. The proteins have several overlapping and complex sets of nomenclature that include names such as VP22, standing for virion protein number 22, or ICP35, standing for infected cell protein number 35. Each gene can encode one or more proteins.

Very little is known about which genes encode proteins that are recognized by HSV-2-specific CD8 T-cells. Each unique clonotype of CD8 T-cell recognizes an 8 to 10 amino acid linear fragment of a protein encoded by HSV-2. Most of these fragments, called epitopes, are 9 amino acids long, but there is no strict upper limit on their length. Each epitope is physically bound to a molecule on the surface of a cell (termed the antigen presenting cells). Typically, the antigen presenting cell is infected with HSV-2, although this is not always the case. In some instances, the antigen presenting cell may phagocytose material from outside the cell that contains non-viable HSV-2 material.

The HLA molecule, in the case of CD8 T-cell recognition, is a heterodimer composed of a HLA class I heavy chain molecule and the molecule $\beta 2$ microglobulin. Because there are many different allelic variants of HLA class I molecules in the human population, an HSV-2 epitope peptide that binds to one allelic variant of HLA class I may not bind to another allelic variant. As a consequence, a HSV-2 epitope peptide that is recognized by CD8 T-cells from one person may not be recognized by CD8 T-cells from another person.

An HSV-2 antigen which has been proven to contain at least one smaller peptide epitope may contain diverse epitopes that are capable of being recognized by CD8 T-cells from many different persons. This pattern has generally been noted for the human immune response to many viruses. The invention described herein relates to the identity of several of HSV-2 protein antigens encoded by HSV-2 genes, and peptide epitopes that are internal fragments of these HSV-2 proteins. These HSV-2 proteins are logical vaccine compounds because they are now proven to stimulate CD8 T-cell responses.

The identification of which HSV-2 proteins are recognized by HSV-2-specific CD8 T-cells has been significantly limited by the difficulty in obtaining clones of HSV-2-specific CD8 T-cells. It has been estimated that less than 1 in 1000 circulating CD8 T-cells in the blood are HSV-2-specific (Posavad et al 1996). In the cloning process, a single cell is stimulated to divide many times and provide a population of genetically identical cells, which are then used to determine which HSV-2 epitope and parent antigen are being recognized. Obtaining these clones has been problematic and only two examples have been published in which HSV-2-specific CD8 T-cell clones have been obtained from blood samples and the HSV-2 antigens and epitopes that they recognize have been determined. The previously used method involves re-stimulating the very rare HSV-2-specific CD8 T-cells in the blood by using autologous HSV-2-infected LCL. This method is susceptible to bias in the population of the resulting cells, in that only memory CD8 T-cells that recognize HSV-2 antigens that are presented by the LCL may be re-stimulated. In addition, the previous method may lead to the repetitive isolation of genetically identical progeny of the same CD8 T-cell in the original blood sample, purely as a consequence of their replication in cell culture prior to the cloning step. The method of the invention overcomes both of these potential shortcomings.

The method of the invention takes advantage of the cell surface expression of a molecule associated with the homing of T-cells to the skin to rapidly and efficiently purify HSV-2-specific CD8 T-cells from the blood. With this method, it is possible to obtain large panels (up to 20 or more) of HSV-2-specific CD8 T-cells from a small blood specimen in about 2 weeks. This method has been used to isolate several series of HSV-2-specific CD8 T-cell clones. In several examples, blood samples have been obtained from persons who have very mild HSV-2 infection. These people have no symptoms or lesions. The study of the immune response in persons who have no symptoms or lesions can facilitate identification of the immune responses associated with this successful adaptation to the HSV-2 infection and provide rational benchmarks for vaccination or immune therapy.

Figure 2A:
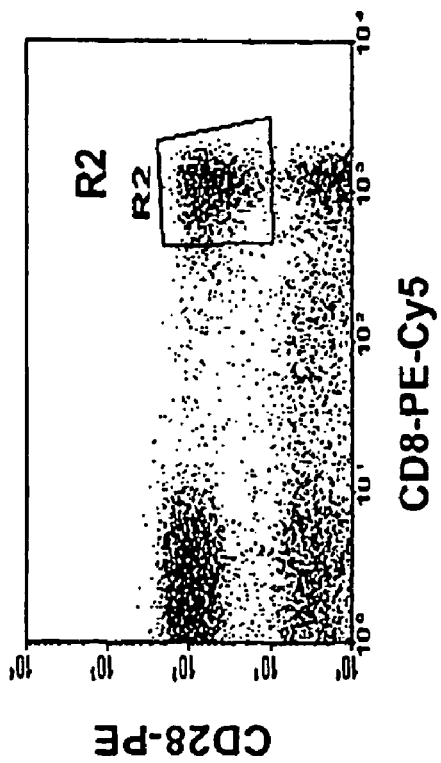
FIGS. 2A-2C. Representative data from a typical human subject showing the physical and antigen expression characteristics of the cells that are sorted to purify HSV-2-specific T-cells from un-manipulated PBMC. The PBMC are stained with three different fluorescently labeled mAb.
Figure 2B:
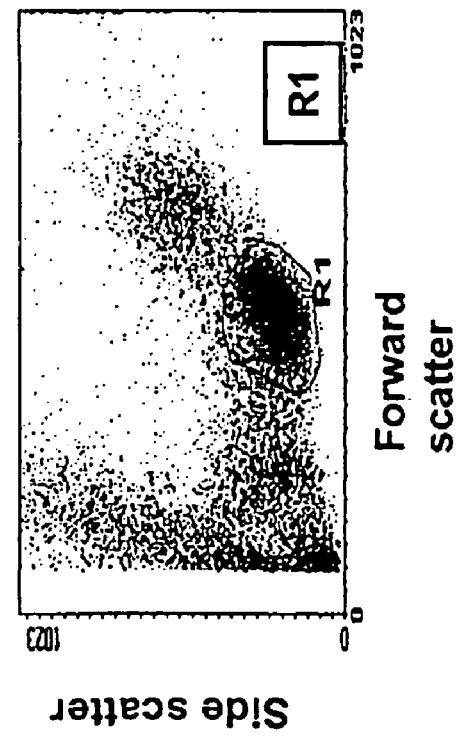
Figure 2C:
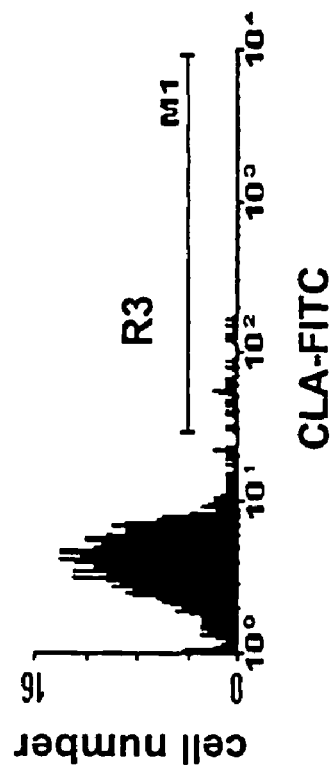

T-cell homing to skin includes an adherence step and a cell migration step. In the adherence step, circulating T-cells exhibit rolling adhesion to the inner surface of vascular endothelial cells in the dermis. It is believed that a molecular determinant that is very tightly associated with an antigen termed CLA (cutaneous lymphocyte associated antigen) is the adhesion molecule on the T-lymphocyte. About 5% of circulating CD8 T-lymphocytes express CLA. CLA is defined by the binding of an anti-CLA monoclonal antibody. The molecular determinant that is very tightly associated with CLA is able to bind to E-selectin. E-selectin expression is up-regulated in the dermis on endothelial cells in the presence of inflammation. As demonstrated in the Examples hereinbelow, circulating HSV-2-specific CD8 T-cells preferentially express CLA. About 50-80% of circulating HSV-2-specific CD8 T-cells express CLA (FIG. 2). In addition, circulating HSV-2-specific T-cells that recognize the same specific epitope in UL49 also highly (>85%) express the cell surface protein CD28.

Figure 3:
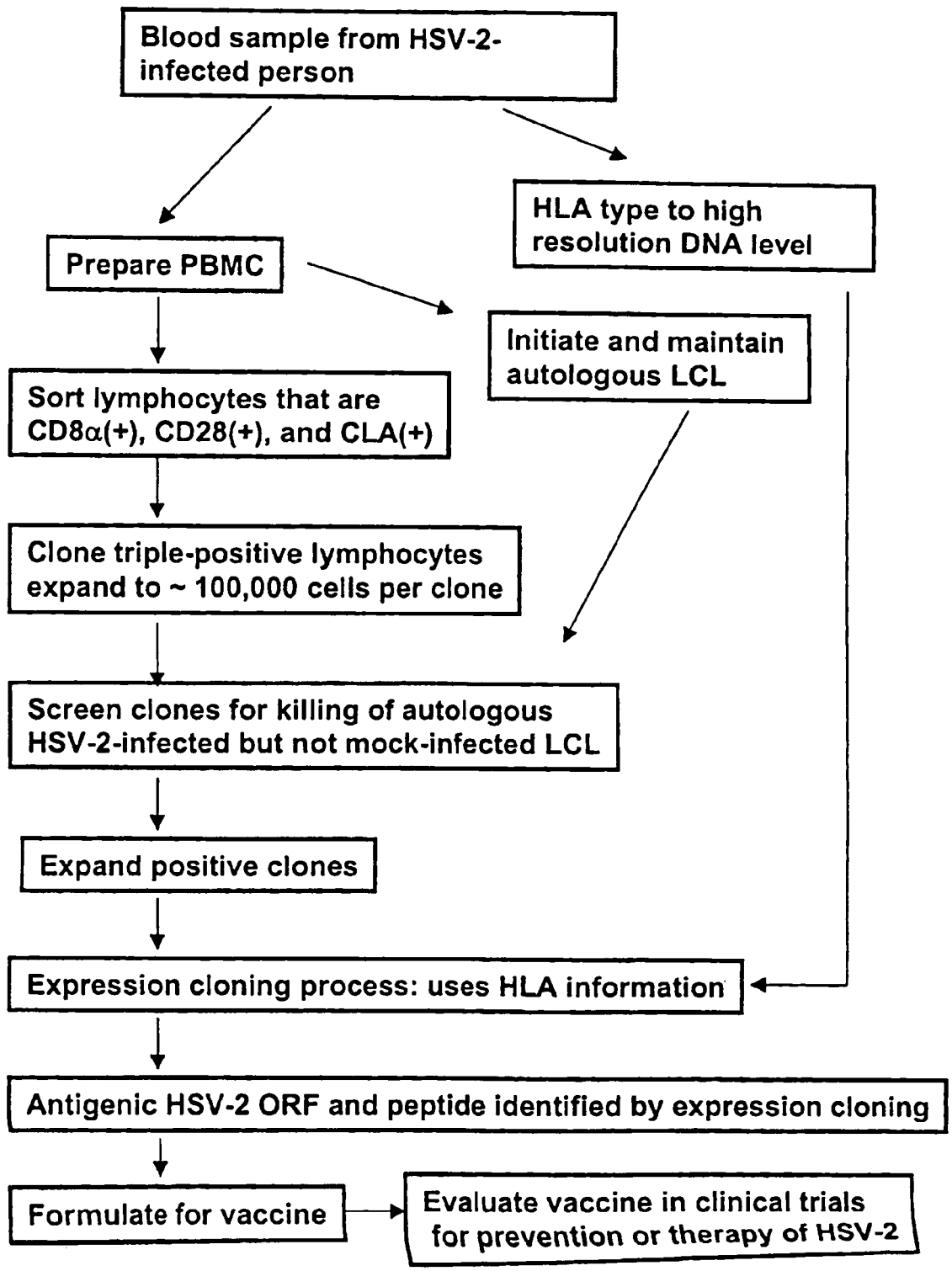
FIG. 3. General outline of one example of the process, based on the use of the skin-homing receptor, CLA, to discover vaccine compounds to prevent or treat HSV-2 infection.

This discovery was used to design a purification procedure to purify HSV-2-specific CD8 T-cells from the blood. Based on an hypothesis that HSV-2-specific CD8 T-cells of diverse fine specificity (recognizing many different antigens) would all express CLA and CD28, cells that express CD8, CD28, and CLA were purified from the blood (FIG. 2 shows representative data from an example of cell sorting). The starting specimen contains PBMC, which are whole un-manipulated mononuclear cells from the blood. Many HSV-2-specific T-cell clones were obtained. Expression cloning technology was then used to determine their fine specificity. Fine specificity includes the HSV-2 antigen and peptide epitope that each clone recognized, together with the specific HLA class I allelic variant that was required for the recognition. FIG. 3 gives the overall schema for the method.

Purification of Virus-Specific T Lymphocytes

The invention provides a method for the rapid and efficient enrichment of cells bearing the skin-homing-associated CLA molecule. This method is useful for identifying and obtaining viral antigens recognized by T-cells that are specific for viruses that attack the skin. Examples include any of the numerous varieties of human papillomavirus (HPV), which causes warts and cervical and penile and anal cancer, members of the pox virus family such as small pox, vaccinia and molluscum contagiosum, and varicella zoster virus (VZV) that causes chicken pox and herpes zoster, as well as herpes simplex virus (HSV). The following describes an embodiment of the method applied to the identification of HSV-2 antigens. Those skilled in the art will appreciate the ease with which the method can be applied to other pathogens that attack the skin.

Blood is obtained from a person with HSV-2 infection. Infection is typically diagnosed by the presence of antibodies to HSV-2 in the blood. A portion of the blood can be tested to determine which allelic forms of DNA are present at the HLA class I A and B loci. The blood is processed to yield peripheral blood mononuclear cells (PBMC) using conventional techniques. For example, PBMC can be isolated from whole blood samples using different density gradient centrifugation procedures (e.g., Ficoll-Hypaque gradient; Bennett & Breit, 1994, J. Leukoc. Biol. 56:236-240).

A portion of the PBMC are immortalized, typically by infecting them with live Epstein-Barr virus. The resultant cell line, termed LCL, are a convenient antigen presenting cell for testing candidate HSV-2-specific CD8 CTL clones in a cytotoxicity (cell killing) assay. The LCL are maintained in continuous cell culture using standard methods. A general scheme outlining one embodiment of the method is provided in FIG. 3.

Another portion of the PBMC can be labeled with one or more markers for sorting. One marker is used to detect CLA status, and additional markers can be used to select for other desired lymphocyte features. In a typical embodiment, the PBMC are stained with three monoclonal antibodies (mAb), each of which further comprises a distinct detectable marker. In one embodiment, each mAb is chemically bound to a different fluorescent molecule. The staining can either be done on a fresh preparation of PBMC or can be done on PBMC that have been stored in a cold environment and then resuscitated in a living form.

In one embodiment, the first mAb binds to the $\alpha$ subunit of CD8, the second mAb binds to CD28, and the third mAb binds to CLA. The cells can be processed with a cell sorter. Cells can be selected and retained on the basis of the following characteristics: 1) when analyzed for forward scatter and side scatter, fall in the distribution characteristic for lymphocytes, 2) express high levels of CD8$\alpha$, 3) are positive for expression of CD28, and 4) express high levels of CLA. These cells are sorted into a physiologically compatible cell culture fluid. FIG. 2 shows an example of data from a cell sorting procedure.

In some embodiments, it may be desirable to determine whether or not HSV-2-specific CD8 T-cells have been isolated by this sorting procedure. In this variation of the method, the sorted cells are expanded as a bulk population of mixed cells. A mitogenic substance that causes the lymphocytes to divide, and proper growth media, growth factors, and feeder cells are provided. The resultant expanded cell population can then be tested in a cell killing assay.

Figure 4:
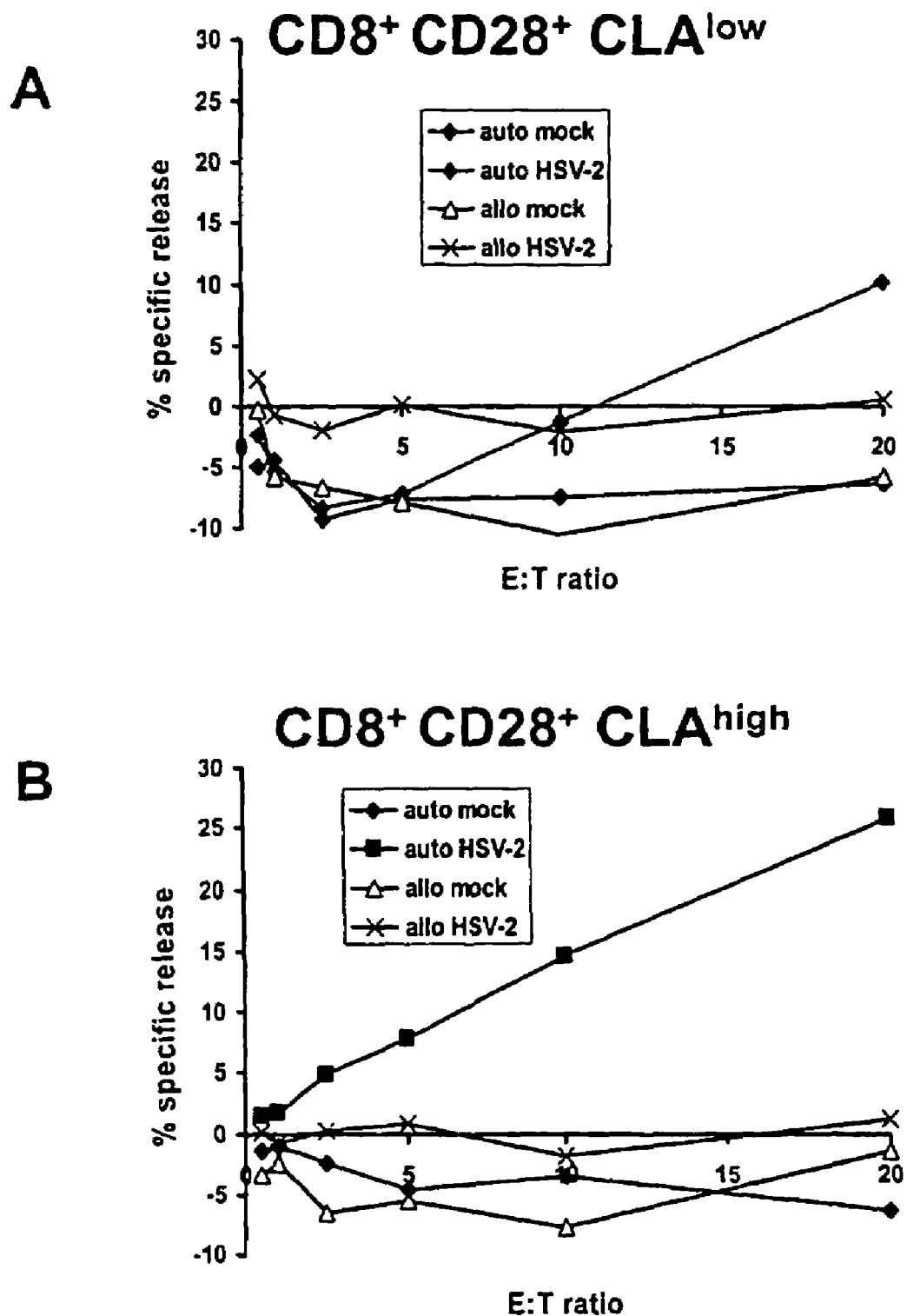
FIGS. 4A-4B. Representative data from a typical human subject showing that sorting cells that express high levels of CLA leads to the enrichment of HSV-2-specific CTL. PBMC are stained with mAb specific for CD8α, CD28, and CLA, and sorted into two groups of cells. Both groups are high expressers of CD8 and CD28. The groups differ in their expression of CLA. After sorting the cells are expanded as a bulk culture, and are tested for the killing of autologous ("auto"), or HLA class I-mismatched allogeneic ("allo") LCL that have been either infected with HSV-2 or not infected.
Figure 5:
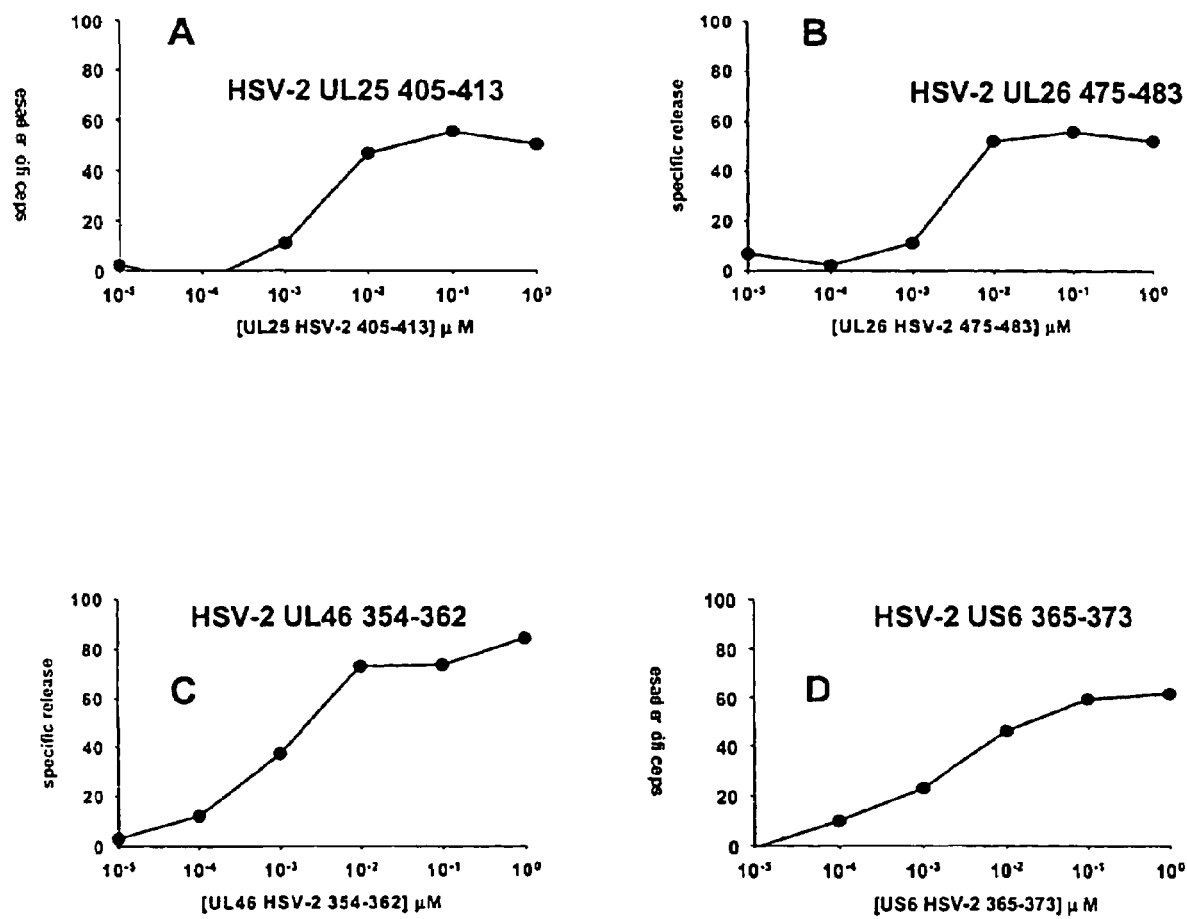
FIGS. 5A-5D. Representative graphs showing the ability of nine amino acid-long synthetic peptides, which in each case correspond to the predicted amino acid sequence HSV-2 open reading frame, to allow HSV-2-specific T-lymphocytes clones that were purified by the skin-homing method to recognize and kill HSV-2-infected cells. In each case, increasing concentrations of peptide were incubated with the autologous LCL "target" cells. Concentrations in molarity are shown on the X axis. The Y axis indicates the extent to which the T-cell clone, which had been purified from the blood on the basis of CLA skin-homing receptor expression, killed the peptide-treated target cell. The indicated statistic, $EC_{50}$, is a graphical estimate of the concentration in molarity of the HSV-2-encoded peptide that is required to allow 50% of maximal recognition by the HSV-2-specific T-cell clone.
Figure 6A:
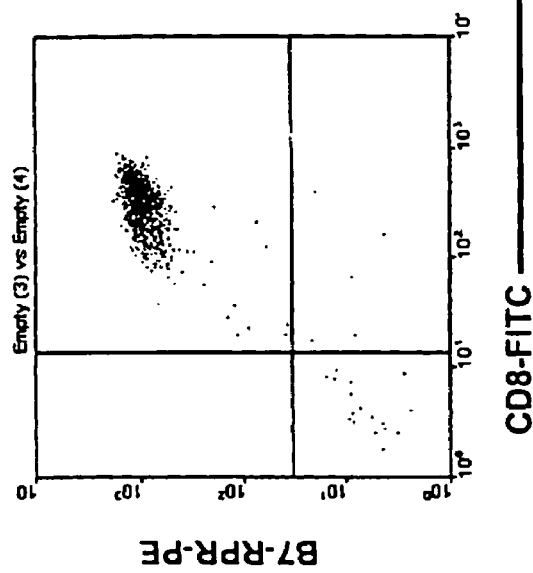
FIGS. 6A-6I. Specificity of tetramer staining and detection of HSV-specific cells in PBDMC.
Figure 6B:
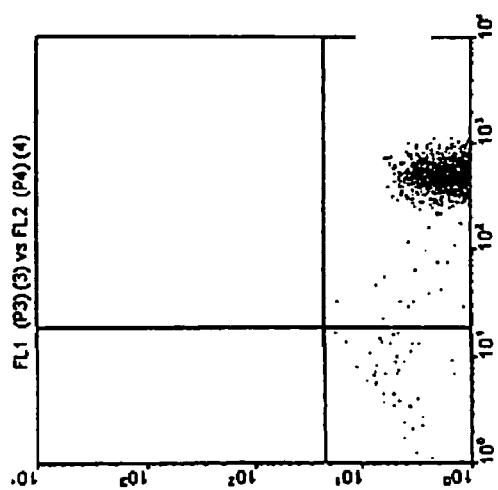
Figure 6C:
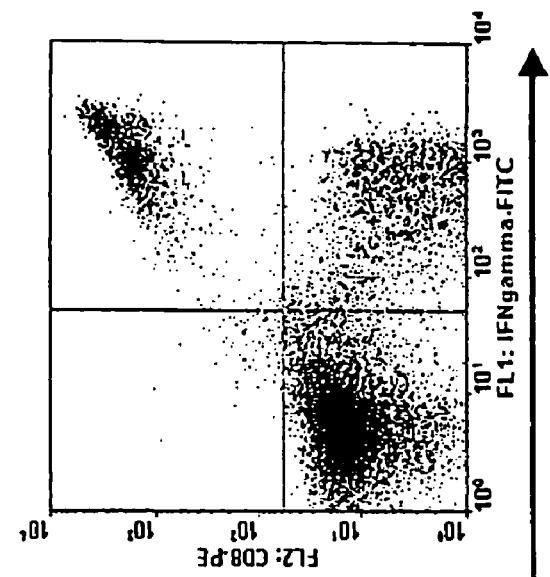
Figure 6D:
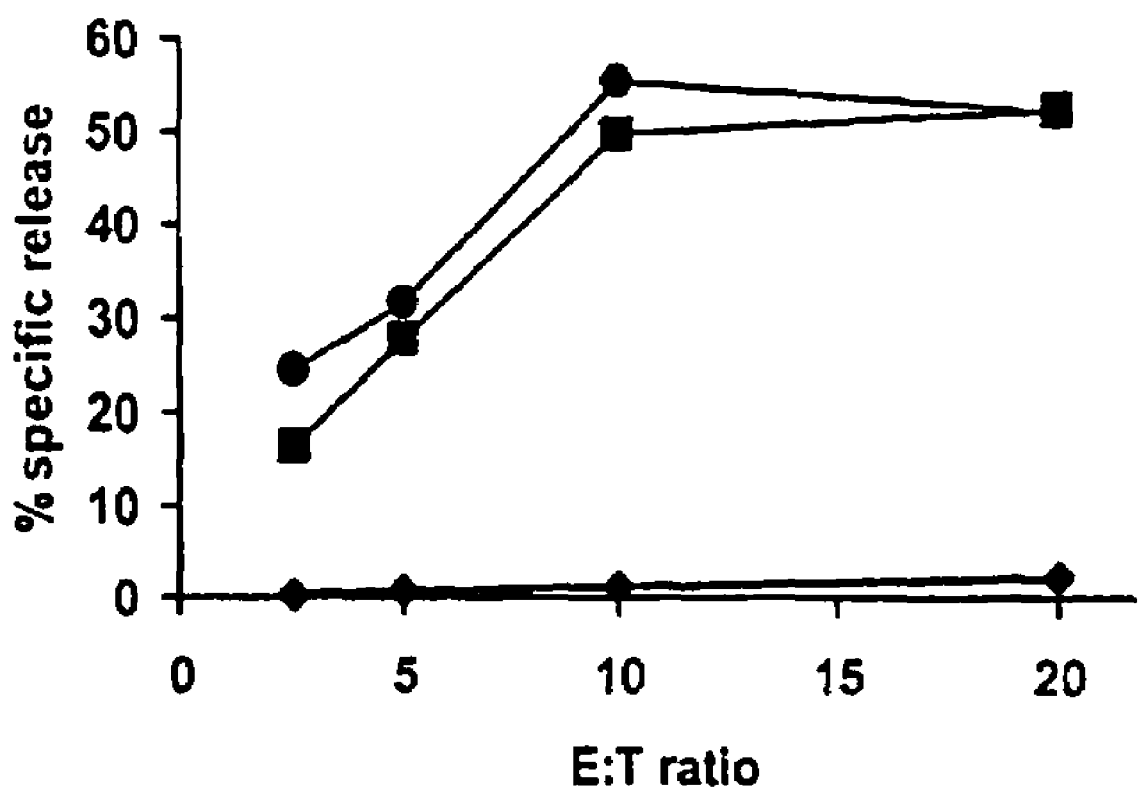
Figure 6F:
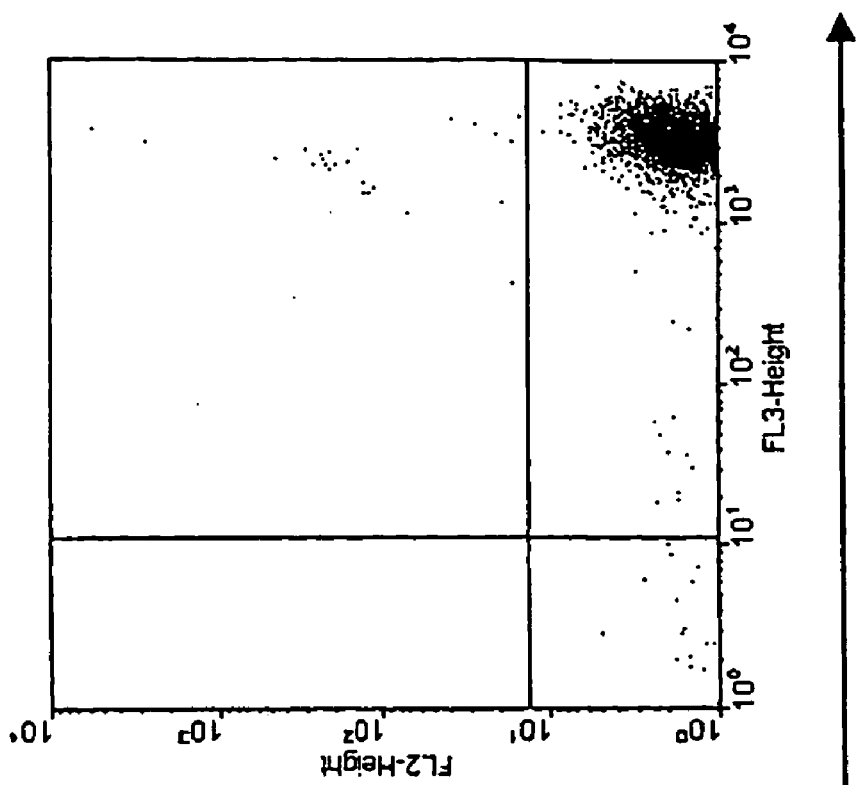
Figure 6E:
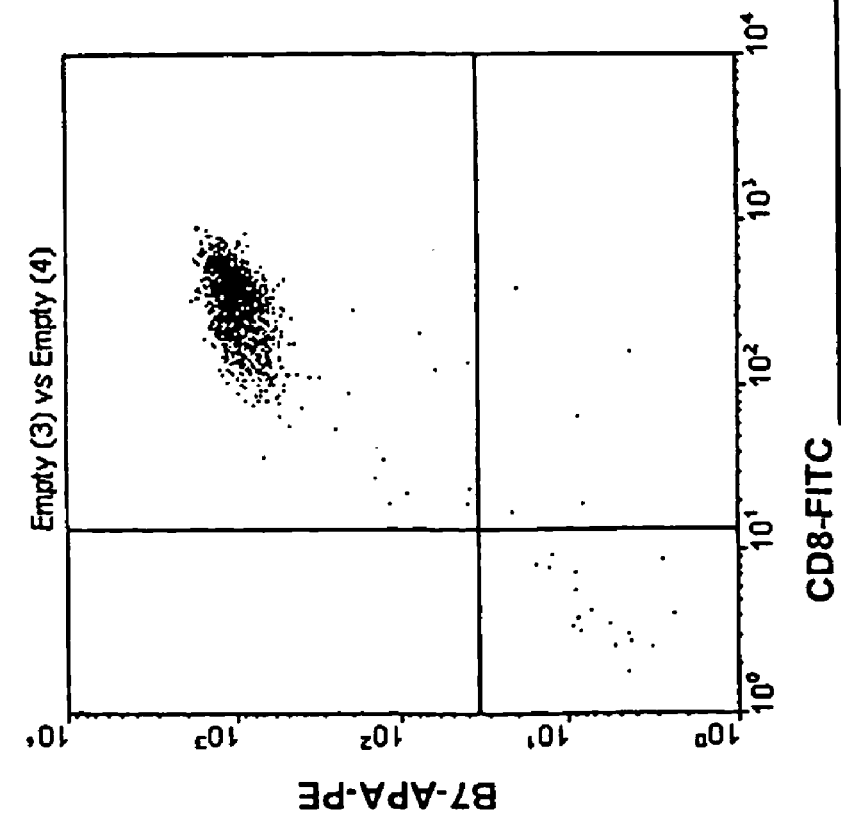
Figure 6H:
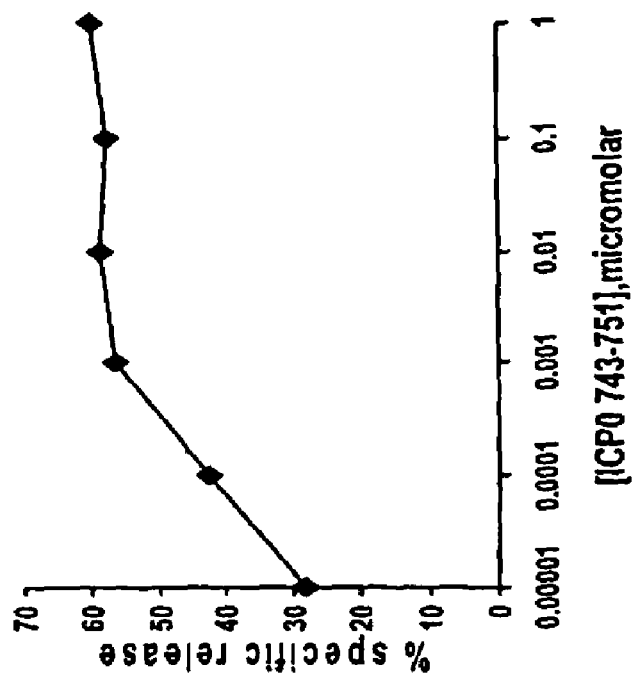
Figure 6G:
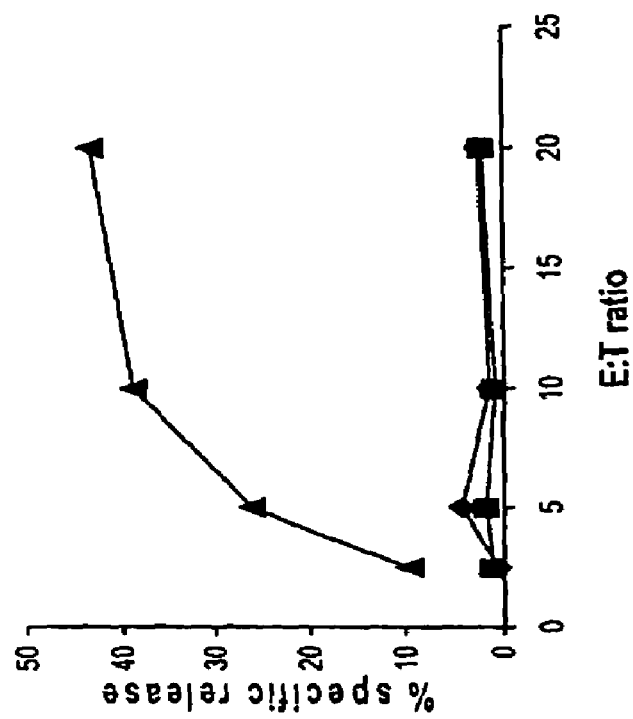
Figure 6I:
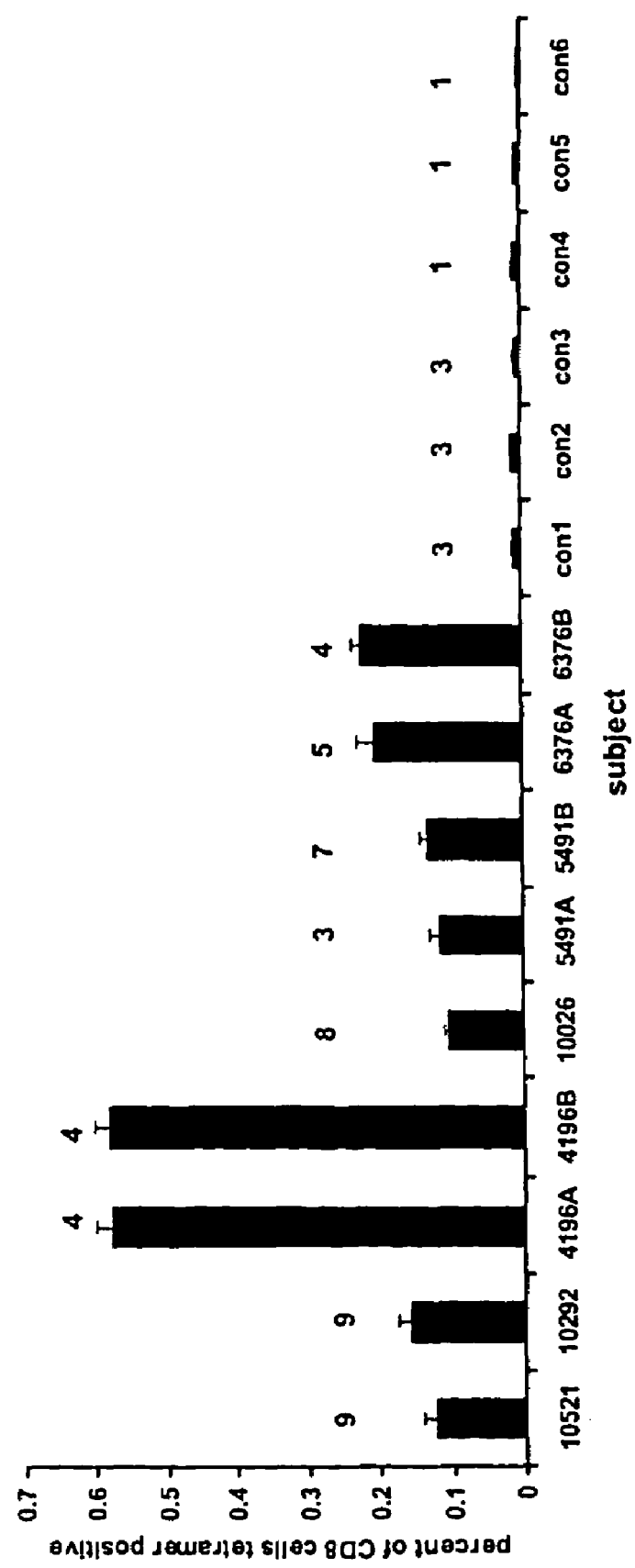

Examples of data from a human subject is shown in FIG. 4. In this example, cells with high and low levels of CLA were each expanded separately to study the association of CLA expression and HSV-2-specific killing activity. Only the CLA-high cells showed killing of HSV-2-specific autologous LCL. The CLA-low cells were otherwise sorted on the same criteria (CD8$\alpha$-high and CD28-high) and cultured and tested in an identical fashion. The CLA-low cells had no killing activity. The fact that the CLA-high cells only killed autologous HSV-2-infected cells, but not non-self or allogeneic HSV-2 infected cells, indicates that typical CD8 HLA class I CTL were present.

To isolate HSV-2-specific T-cell clones in another variant of the method, the sorted CLA-high, CD28-high, CD8$\alpha$-high cells are, immediately after sorting them from PBMC, diluted and plated at one cell peer well or lower density into small culture wells. To each well, a combination of inactivated cells, mitogenic substances, and growth factors are added in a liquid medium that enhance the growth of the single live lymphocyte. These clonal cultures are expanded in cell number.

To test the candidate clones for specificity for HSV-2, standard methods are used. Autologous LCL are either infected overnight with HSV-2 or left uninfected. When the candidate clones are about 2 weeks old and have reached the growth stage of approximately 100,000 cells, a portion of each clone is tested for its ability to kill both the uninfected and HSV-2 infected cells. The desired clones are the clones that do not kill the uninfected autologous LCL but do kill the HSV-2 infected autologous LCL. A standard assay can be used, such as a chromium release cytotoxicity assay.

Examples of the purification of HSV-2-specific CD8 CTL from blood specimens from eight different HSV-2-infected adult humans are shown in Table 1. For each subject, the number of clones screened in CTL assays and the number positive are indicated. The criteria for being listed as positive are >25% specific release for HSV-2-infected autologous cells, and no appreciable killing of non-infected autologous cells. For most subjects and most clones, HSV-2-specific and HLA class I-restricted CTL activity has been confirmed in more than one assay. The far right column indicates the percentage of all clones that were screened that were HSV-2-specific by killing HSV-2-infected autologous cells.

TABLE 1

Isolation of HSV-2-specific CD8 CTL clones from blood specimens using the cell sorting method which includes CLA expression as a sorting criteria.

| Subject ID no. | Number of clones positive | Number of clones screened | Percentage of clones positive for killing of HSV-2 infected autologous cells |
|---|---|---|---|
| 6376 | 6 | 172 | 3.5 |
| 10433 | 5 | 64 | 7.8 |
| 10295 | 14 | 86 | 16.3 |
| 10569 | 95 | 319 | 29.8 |

TABLE 1-continued

Isolation of HSV-2-specific CD8 CTL clones from blood specimens using the cell sorting method which includes CLA expression as a sorting criteria.

| Subject ID no. | Number of clones positive | Number of clones screened | Percentage of clones positive for killing of HSV-2 infected autologous cells |
|---|---|---|---|
| 10063 | 32 | 96 | 33.3 |
| 5491 | 5 | 82 | 6.1 |
| 5101 | 5 | 192 | 2.6 |
| 10352 | 2 | 150 | 1.3 |

The clones that meet these criteria can be further expanded in cell number by using standard techniques. For determining their fine specificity (the identity of the HSV-2 antigen and epitope they recognize), they are typically expanded to at least 200 million cells. These cells can be frozen in aliquots for later use.

Antigen and Epitope Determination

The fine specificity of HSV-2-specific CD8 T-cell clones identified by the above method can be determined using expression cloning, e.g., as described in U.S. Pat. No. 6,375,952, issued Apr. 23, 2002. The method can include identification of the allelic form of the HLA class I molecule that binds to the HSV-2 epitope. Typically, a fragment of the HSV-2 genome that contains the final epitope is initially identified. This initial fragment usually is predicted to encode a portion of one or more HSV-2 antigens. Table 2 lists exemplary results from the process of epitope discovery resulting from the CLA-based cell sorting method described herein and followed by expression cloning. FIG. 3 shows an example of how the methods of CLA-based cell sorting can be combined with expression cloning to identify vaccines for prevention or therapy.

TABLE 2

DNA sequences of HSV-2 ORFs recognized by HSV-2-specific T-cell clones purified from blood on the basis of CLA expression.

| | | | Properties of Initial + Genomic Fragment | | | |
|---|---|---|---|---|---|---|
| Donor[1] | Clone name | HLA restricting allele[2] | HSV-2 nucleotide numbers[3] | Predicted HSV-2 gene[4] | Predicted HSV-2 protein or proteins[5] | HSV-2 peptide shown to be active in cell killing assays[6] |
| 10569 | 1F3 | B*1402 | 49999-50287 | UL25 | UL25 322-417 | UL25 amino acids 405-413, SEQ ID NO: 1: DRLDNRLQL |
| 6376 | 1E4 | B*0702 | 52294-52910 | UL26 and UL26.5[7] | UL26: 404-627[8] | UL26 amino acids 475-483, SEQ ID NO: 2: GPHETITAL[8] |
| 10295 | F8 | B*1402 | 17406-17824 | UL7 | UL7: 50-192 | UL7 amino acids 174-186, SEQ ID NO: 3: HASPFERVRCLLL |
| 5491 | E2 | A*0101 | 99085-10083 | UL46 | VP11/12 254-722 | UL46 amino acids 354-362, SEQ ID NO: 4: ASDSLNNEY |
| 10569 | 2B9 | B*27052 | 142038-142393 | US6 | gD2 342-393 | US6 amino acids 365-373, SEQ ID NO: 5: RRAQMAPKR |

TABLE 2-continued

DNA sequences of HSV-2 ORFs recognized by HSV-2-specific T-cell clones purified from blood on the basis of CLA expression.

| | | | Properties of Initial + Genomic Fragment | | | |
|---|---|---|---|---|---|---|
| Donor[1] | Clone name | HLA restricting allele[2] | HSV-2 nucleotide numbers[3] | Predicted HSV-2 gene[4] | Predicted HSV-2 protein or proteins[5] | HSV-2 peptide shown to be active in cell killing assays[6] |
| 5101 | 2H1 | B*5701 | 145347-146693 | US8 and US9 | gE2 503-545 and US9 1-89 | US8 amino acids 518-526, SEQ ID NO: 6: KSRRPLTTF |

[1]Internal subject identifier from the clinic.
[2]HLA nomenclature from Marsh et al., 2000, The HLA Facts Book, Academic Press, San Diego. The listed HLA alleles were each obtained as cDNA clones and used in the expression cloning process as detailed in Koelle et al., 2001, J. Immunol. 166: 4049-4058.
[3]Beginning and ending nucleotide residues of the initially positive fragment of the HSV-2 strain HG52 genome, as analyzed using the nucleotide sequence on file as Genbank file number NC_001798.
[4]Name of the HSV-2 open reading frame that is predicted to be included in the nucleotide residues present in the active fragment.
[5]Name of the corresponding HSV-2 protein that is predicted be encoded by the HSV-2 gene. Nomenclature is per Roizman and Knipe, 2001, In: Fields Virology, Fourth Edition, Vol. 2. Ed: Knipe and Howley, Lippincott Williams and Wilkins, Philadelphia, pages 2399-2460. Also listed are the predicted amino acids encoded by the fragment of the indicated gene that are encoded by the initial positive DNA fragment from the HSV-2 library used in expression cloning.
[6]The sequence, using the standard single letter nomenclature for L-amino acids, of the epitope peptides that are recognized by the indicated CD8 T-cell clones. Also listed are the amino acid residue numbers from the predicted protein sequence as listed in Genbank file number NC_001798. When loaded onto LCL that express that indicated allelic form of HLA class 1, the indicated CD8 T-cell clone will kill the peptide-loaded LCL. Peptides were synthesized by standard chemistry by a commercial laboratory and dissolved in DMSO prior to testing.
[7]Note that for CD8 T cell clone 1E4, the nucleotide residues are in two different open reading frames, designated UL26 and UL26.5. These open reading frames have different ATG triplets that encode the methionine residue that begins different proteins, but are in-frame, and have the same predicted stop codon. UL26.5 is therefore a shorter version of UL26. Details of the nomenclature are available in Roizman and Knipe, 2001 (supra).
[8]Note that the UL26 open reading frame is predicted to encode several proteins including VP24, VP21, VP22a, and ICP35. For simplicity, the term UL26 is used for a predicted protein sequence and the number of the amino acids residues in the UL26 open reading frame that form an active peptide epitope are listed. Details of the nomenclature are available in Roizman and Knipe, 2001 (supra).

HSV Polypeptides

In one embodiment, the invention provides an isolated herpes simplex virus (HSV) polypeptide. The polypeptide comprises a UL7, UL25, UL26, UL46 (VP1/12), US6 (gD2) or US8 (gE2) protein or a fragment thereof. In one embodiment, the fragment comprises amino acids 174-186 or 50-192 of UL7; 405-413 or 322-417 of UL25; 475-483 or 404-627 of UL26; 354-362 or 254-722 of UL46; 365-373 or 342-393 of US6; or 518-526 or 503-545 of US6. A fragment of the invention consists of less than the complete amino acid sequence of the corresponding protein, but includes the recited epitope. As is understood in the art and confirmed by assays conducted using fragments of widely varying lengths, additional sequence beyond the recited epitope can be included without hindering the immunological response. A fragment of the invention can be as few as 8 amino acids in length, or can encompass 10%, 20%, 30%, 40%, 50%, 60%, 70%, 80%, 90% or 95% of the full length of the protein.

The reference to amino acid residues is made with respect to the proteins of the HSV-2 genome as described in A. Dolan et al., 1998, J. Virol. 72(3):2010-2021. The amino acid sequences of UL7, UL25, UL26, UL46 (VP11/12), UL54 (ICP27), or US6 (gD2) are as follows.

UL7

(SEQ ID NO: 7)

```
  1 madptpadeg taaailkqai agdrslveva egisnqallr macevrqvsd rqprftatsv 61 lrvdvtprgr lrfvldgssd dayvasedyf krcgdqptyr gfavvvltan edhvhslavp 121 plvllhrlsl frptdlrdfe lvcllmylen cprshatpsl fvkvsawlgv varhaspfer 181 vrclllrsch wilntlmcma gvkpfddelv lphwymahyl lannpppvls alfcatpqss 241 alqlpgpvpr tdcvaynpag vmgscwnskd lrsalvywwl sgspkrrtss lfyrfc
```

-continued

UL25

(SEQ ID NO: 8)

```
  1 mdpyypfdal dvwehrrfiv adsrsfitpe fprdfwmlpv fnipretaae raavlqaqrt
 61 aaaaalenaa lqaaelpvdi errirpieqq vhhiadalea letaaaaaee adaardaear
121 gegaadgaap sptagpaaae mevqivrndp plrydtnlpv dllhmvyagr gaagssgvvf
181 gtwyrtiqer tiadfplttr sadfrdgrms ktfmtalvls lqscgrlyvg qrhysafeca
241 vlclyllyrt thesspdrdr apvafgdlla rlprylarla avigdesgrp qyryrddklp
301 kaqfaaaggr yehgalathv viatlvrhgv lpaapgdvpr dtstrvnpdd vahrddvnra
361 aaaflarghn lflwedqtll ratantital avlrrllang nvyadrldnr lqlgmlipga
421 vpaeaiarga sgldsgaiks gdnnlealcv nyvlplyqad ptveltqlfp glaalcldaq
481 agrplastrr vvdmssgarq aalvrltale linrtrtntt pvgeiinahd algiqyeqgp
541 gllaqqarig lasntkrfat fnvgsdydll yflclgfipq ylsva
```

UL26

(SEQ ID NO: 9)

```
  1 masaemrerl eaplpdravp iyvagflaly dsgdpgelal dpdtvraalp penplpinvd
 61 hrarcevgrv lavvndprgp ffvgliacvq lervletaas aaiferrgpa lsreerllyl
121 itnylpsvsl stkrrqdevp pdrtlfahva lcaigrrlgt ivtydtslda aiapfrhldp
181 atregvrrea aeaelalagr twapqvealt htllstavnn mmlrdrwslv aerrrqagia
241 ghtylqasek fkiwgaesap apergyktga pgamdtspaa svpapqvavr arqvassssss
301 ssfpapadmn pvsasgapap pppgdgsylw ipashynqlv tgqsaprhpp ltacglpaag
361 tvayghpgag psphypppppa hpypgmlfag pspleaqiaa lvgaiaadrq agglpaaagd
421 hgirgsakrr rheveqpeyd cgrdepdrdf pyypgearpe prpvdsrraa rqasgpheti
481 talvgavtsl qqelahmrar thapygpypp vgpyhhphad tetpaqppry pakavylppp
541 hiappgppls gavpppsypp vavtpgpapp lhqpspahah ppppppgptp ppaaslpqpe
601 apgaeagalv nassaahvnv dtaraadlfv sqmmgsr
```

UL46 (VP11/12)

(SEQ ID NO: 10)

```
  1 mqrrargass lrlarcltpa nlirganagv perrifagcl lptpegllsa avgvlrqrad
 61 dlqpafltga drsvrlaarh hntvpesliv dglasdphyd yirhyasaak qalgevelsg
121 gqlsrailaq ywkylqtvvp sgldipddpa gdcdpslhvl lrptllpkll vrapfksgaa
181 aakyaaavag lrdaahrlqq ymffmrpadp srpstdtalr lsellayvsv lyhwaswmlw
241 tadkyvcrrl gpadrrfval sgsleapaet farhldrgps gttgsmqcma lraavsdvlg
301 hltrlahlwe tgkrsggtyg ivdaivstve vlsivhhhaq yiinatltgy vvwasdslnn
361 eyltaavdsq erfcrtaapl fptmtapswa rmelsikswf gaalapdllr sgtpsphyes
421 ilrlaasgpp ggrgavggsc rdkiqrtrrd nappplprar phstpaaprr crrhredlpe
481 pphvdaadrg pepcagrpat yythmagapp rlpprnpapp eqrpaaaarp laaqreaagv
541 ydavrtwypd aeaepdqmen tyllpdddaa mpagvglgat paadttaaaa wpaeshapra
601 psedadsiye svgedggrvy eeipwvrvye nicprrrlag gaalpgdapd spyieaenpl
661 ydwggsalfs prratrapdp glslspmpar prtnalandg ptnvaalsal ltklkrgrhq
721 sh
```

-continued

US6 (gD2)
(SEQ ID NO: 11)
```
  1 mgrltsgvgt aallvvavgl rvvcakyala dpslkmadpn rfrgknlpvl dqltdppgvk 61 rvyhiqpsle dpfqppsipi tvyyavlera crsvllhaps eapqivrgas dearkhtynl 121 tiawyrmgdn caipitvmey tecpynkslg vcpirtqprw syydsfsavs ednlgflmha 181 pafetagtyl rlvkindwte itqfilehra rasckyalpl rippaaclts kayqqgvtvd 241 sigmlprfip enqrtvalys lkiagwhgpk ppytstllpp elsdttnatq pelvpedped 301 salledpagt vssqippnwh ipsiqdvaph hapaapsnpg liigalagst laviviggia 361 fwvrrraqma pkrlrlphir dddappshqp lfy
```

US8 (gE2)
(SEQ ID NO: 12)
```
  1 margaglvff vgvwvvscla aaprtswkrv tsgedvvllp apaertrahk llwaaeplda 61 cgplrpswva lwpprrvlet vvdaacmrap eplaiayspp fpagdeglys elawrdrvav 121 vneslviyga letdsglytl svvglsdear qvasvvlvve papvptptpd dydeeddagv 181 tnarrsafpp qppprrppva ppthprvipe vshvrgvtvh metleailfa pgetfgtnvs 241 ihaiahddgp yamdvvwmrf dvpsscadmr iyeaclyhpq lpeclspada pcavsswayr 301 lavrsyagcs rttppprcfa earmepvpgl awlastvnle fqhaspqhag lylcvvyvdd 361 hihawghmti staaqyrnav veqhlpqrqp epveptrphv raphpapsar gplrlgavlg 421 aalllaalgl sawacmtcwr rrswravksr asatgptyir vadselyadw ssdsegerdg 481 slwqdpperp dspstngsgf eilsptapsv yphsegrksr rplttfgsgs pgrrhsqasy 541 psvlw
```

The polypeptide can be a fusion protein. In one embodiment, the fusion protein is soluble. A soluble fusion protein of the invention can be suitable for injection into a subject and for eliciting an immune response. Within certain embodiments, a polypeptide can be a fusion protein that comprises multiple polypeptides as described herein, or that comprises at least one polypeptide as described herein and an unrelated sequence. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., 1985, Gene 40:39-46; Murphy et al., 1986, Proc. Natl. Acad. Sci. USA 83:8238-8262; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located 5' to the DNA sequence encoding the first polypeptides. Similarly, stop codons required to end translation and transcription termination signals are present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al., 1997, New Engl. J. Med., 336:86-9).

Within preferred embodiments, an immunological fusion partner is derived from protein D, a surface protein of the gram-negative bacterium *Haemophilus* influenza B (WO 91/18926). Preferably, a protein D derivative comprises approximately the first third of the protein (e.g., the first N-terminal 100-110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenza virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; Gene 43:265-292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see Biotechnology 10:795-798, 1992). Within a preferred embodiment, a repeat portion of LYTA may be incorporated into a fusion protein. A repeat portion is found in the C-terminal region starting at residue 178. A particularly preferred repeat portion incorporates residues 188-305.

In some embodiments, it may be desirable to couple a therapeutic agent and a polypeptide of the invention, or to couple more than one polypeptide of the invention. For example, more than one agent or polypeptide may be coupled directly to a first polypeptide of the invention, or linkers that provide multiple sites for attachment can be used. Alternatively, a carrier can be used. Some molecules are particularly suitable for intercellular trafficking and protein delivery, including, but not limited to, VP22 (Elliott and O'Hare, 1997, Cell 88:223-233; see also Kim et al., 1997, J. Immunol. 159:1666-1668; Rojas et al., 1998, Nature Biotechnology 16:370; Kato et al., 1998, FEBS Lett. 427(2):203-208; Vives et al., 1997, J. Biol. Chem. 272(25):16010-7; Nagahara et al., 1998, Nature Med. 4(12):1449-1452).

A carrier may bear the agents or polypeptides in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088).

In general, polypeptides (including fusion proteins) and polynucleotides as described herein are isolated. An "isolated" polypeptide or polynucleotide is one that is removed from its original environment. For example, a naturally occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not part of the natural environment.

The polypeptide can be isolated from its naturally occurring form, produced by recombinant means or synthesized chemically. Recombinant polypeptides encoded by DNA sequences described herein can be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably the host cells employed are *E. coli*, yeast or a mammalian cell line such as Cos or CHO. Supernatants from the soluble host/vector systems that secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Fragments and other variants having less than about 100 amino acids, and generally less than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, wherein amino acids are sequentially added to a growing amino acid chain (Merrifield, 1963, J. Am. Chem. Soc. 85:2146-2149). Equipment for automated synthesis of polypeptides is commercially available from suppliers such as Perkin Elmer/Applied BioSystems Division (Foster City, Calif.), and may be operated according to the manufacturer's instructions.

Variants of the polypeptide for use in accordance with the invention can have one or more amino acid substitutions, deletions, additions and/or insertions in the amino acid sequence indicated that result in a polypeptide that retains the ability to elicit an immune response to HSV or HSV-infected cells. Such variants may generally be identified by modifying one of the polypeptide sequences described herein and evaluating the reactivity of the modified polypeptide using a known assay such as a T cell assay described herein. Polypeptide variants preferably exhibit at least about 70%, more preferably at least about 90%, and most preferably at least about 95% identity to the identified polypeptides. These amino acid substitutions include, but are not necessarily limited to, amino acid substitutions known in the art as "conservative".

A "conservative" substitution is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gin, asn, ser, thr, (2) cys, ser, tyr, thr, (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

One can readily confirm the suitability of a particular variant by assaying the ability of the variant polypeptide to elicit an immune response. The ability of the variant to elicit an immune response can be compared to the response elicited by the parent polypeptide assayed under identical circumstances. One example of an immune response is a cellular immune response. The assaying can comprise performing an assay that measures T cell stimulation or activation. Examples of T cells include CD4 and CD8 T cells.

One example of a T cell stimulation assay is a cytotoxicity assay, such as that described in Koelle, D M et al., Human Immunol. 1997, 53; 195-205. In one example, the cytotoxicity assay comprises contacting a cell that presents the antigenic viral peptide in the context of the appropriate HLA molecule with a cell, and detecting the ability of the T cell to kill the antigen presenting cell. Cell killing can be detected by measuring the release of radioactive $^{51}$Cr from the antigen presenting cell. Release of $^{51}$Cr into the medium from the antigen presenting cell is indicative of cell killing. An exemplary criterion for increased killing is a statistically significant increase in counts per minute (cpm) based on counting of $^{51}$Cr radiation in media collected from antigen presenting cells admixed with T cells as compared to control media collected from antigen presenting cells admixed with media.

Polynucleotides, Vectors, Host Cells and Recombinant Viruses

The invention provides polynucleotides that encode one or more polypeptides of the invention. The complete genome sequence of HSV-2, strain HG 52, can be found on the NCBI web site (www.ncbi.nih.gov), Accession No. Z86099. The polynucleotide can be included in a vector. The vector can further comprise an expression control sequence operably linked to the polynucleotide of the invention. In some embodiments, the vector includes one or more polynucleotides encoding other molecules of interest. In one embodiment, the polynucleotide of the invention and an additional polynucleotide can be linked so as to encode a fusion protein.

Within certain embodiments, polynucleotides may be formulated so to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

The invention also provides a host cell transformed with a vector of the invention. The transformed host cell can be used in a method of producing a polypeptide of the invention. The method comprises culturing the host cell and recovering the polypeptide so produced. The recovered polypeptide can be purified from culture supernatant.

Vectors of the invention can be used to genetically modify a cell, either in vivo, ex vivo or in vitro. Several ways of genetically modifying cells are known, including transduction or infection with a viral vector either directly or via a retroviral producer cell, calcium phosphate precipitation, fusion of the recipient cells with bacterial protoplasts containing the DNA, treatment of the recipient cells with liposomes or microspheres containing the DNA, DEAE dextran, receptor-mediated endocytosis, electroporation, micro-injection, and many other techniques known to those of skill. See, e.g., Sambrook et al. Molecular Cloning—A Laboratory Manual (2nd ed.) 1-3, 1989; and Current Protocols in Molecular Biology, F. M. Ausubel et al., eds., Greene Publishing Associates, Inc. and John Wiley & Sons, Inc., (1994 Supplement).

Examples of viral vectors include, but are not limited to retroviral vectors based on, e.g., HIV, SIV, and murine retroviruses, gibbon ape leukemia virus and other viruses such as adeno-associated viruses (AAVs) and adenoviruses. (Miller et al. 1990, Mol. Cell Biol. 10:4239; J. Kolberg 1992, NIH Res. 4:43, and Cometta et al. 1991, Hum. Gene Ther. 2:215). Widely used retroviral vectors include those based upon murine leukemia virus (MuLV), gibbon ape leukemia virus (GaLV), ecotropic retroviruses, simian immunodeficiency virus (SIV), human immunodeficiency virus (HIV), and combinations. See, e.g. Buchscher et al. 1992, J. Virol. 66(5): 2731-2739; Johann et al. 1992, J. Virol. 66(5):1635-1640; Sommerfelt et al. 1990, Virol. 176:58-59; Wilson et al. 1989, J. Virol. 63:2374-2378; Miller et al. 1991, J. Virol. 65:2220-2224, and Rosenberg and Fauci 1993 in Fundamental Immunology, Third Edition, W. E. Paul (ed.) Raven Press, Ltd., New York and the references therein; Miller et al. 1990, Mol. Cell Biol. 10:4239; R. Kolberg 1992, J. NIH Res. 4:43; and Cometta et al. 1991, Hum. Gene Ther. 2:215.

In vitro amplification techniques suitable for amplifying sequences to be subcloned into an expression vector are known. Examples of such in vitro amplification methods, including the polymerase chain reaction (PCR), ligase chain reaction (LCR), Qβ-replicase amplification and other RNA polymerase mediated techniques (e.g., NASBA), are found in Sambrook et al. 1989, Molecular Cloning—A Laboratory Manual (2nd Ed) 1-3; and U.S. Pat. No. 4,683,202; PCR Protocols A Guide to Methods and Applications (Innis et al. eds.) Academic Press Inc. San Diego, Calif. 1990. Improved methods of cloning in vitro amplified nucleic acids are described in U.S. Pat. No. 5,426,039.

The invention additionally provides a recombinant microorganism genetically modified to express a polynucleotide of the invention. The recombinant microorganism can be useful as a vaccine, and can be prepared using techniques known in the art for the preparation of live attenuated vaccines. Examples of microorganisms for use as live vaccines include, but are not limited to, viruses and bacteria. In a preferred embodiment, the recombinant microorganism is a virus. Examples of suitable viruses include, but are not limited to, vaccinia virus, canary pox virus, retrovirus, lentivirus, HSV and adenovirus.

Compositions

The invention provides compositions that are useful for treating and preventing HSV infection. The compositions can be used to inhibit viral replication and to kill virally-infected cells. In one embodiment, the composition is a pharmaceutical composition. The composition can comprise a therapeutically or prophylactically effective amount of a polypeptide, polynucleotide, recombinant virus, APC or immune cell of the invention. An effective amount is an amount sufficient to elicit or augment an immune response, e.g., by activating T cells. One measure of the activation of T cells is a cytotoxicity assay, as described in D. M. Koelle et al., 1997, Human Immunol. 53:195-205. In some embodiments, the composition is a vaccine.

The composition can optionally include a carrier, such as a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions of the present invention. Formulations suitable for parenteral administration, such as, for example, by intraarticular (in the joints), intravenous, intramuscular, intradermal, intraperitoneal, and subcutaneous routes, and carriers include aqueous isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, preservatives, liposomes, microspheres and emulsions.

The composition of the invention can further comprise one or more adjuvants. Examples of adjuvants include, but are not limited to, helper peptide, alum, Freund's, muramyl tripeptide phosphatidyl ethanolamine or an immunostimulating complex, including cytokines. In some embodiments, such as with the use of a polynucleotide vaccine, an adjuvant such as a helper peptide or cytokine can be provided via a polynucleotide encoding the adjuvant Vaccine preparation is generally described in, for example, M. F. Powell and M J. Newman, eds., "Vaccine Design (the subunit and adjuvant approach)," Plenum Press (NY, 1995). Pharmaceutical compositions and vaccines within the scope of the present invention may also contain other compounds, which may be biologically active or inactive. For example, one or more immunogenic portions of other viral antigens may be present, either incorporated into a fusion polypeptide or as a separate compound, within the composition or vaccine.

A pharmaceutical composition or vaccine may contain DNA encoding one or more of the polypeptides of the invention, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, 1998, Crit. Rev. Therap. Drug Carrier Systems 15:143-198, and references cited therein. Appropriate nucleic acid expression systems contain the necessary DNA sequences for expression in the patient (such as a suitable promoter and terminating signal). Bacterial delivery systems involve the administration of a bacterium (such as *Bacillus-Calmette-Guerrin*) that expresses an immunogenic portion of the polypeptide on its cell surface or secretes such an epitope. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., 1989, Proc. Natl. Acad. Sci. USA 86:317-321; Flexner et al., 1989, Ann. My Acad. Sci. 569:86-103; Flexner et al., 1990, Vaccine 8:17-21; U.S. Pat. Nos. 4,603,112, 4,769,330, and 5,017,487; WO 89/01973; U.S. Pat. No. 4,777,127; GB 2,200,651; EP 0,345,242; WO 91102805; Berkner, 1988, Biotechniques 6:616-627; Rosenfeld et al., 1991, Science 252:431-434; Kolls et al., 1994, Proc. Acad. Acad. Sci. USA 91:215-219; Kass-Eisler et al., 1993, Proc. Natl. Acad. Sci. USA 90:11498-11502; Guzman et al., 1993, Circulation 88:2838-2848; and Guzman et al., 1993, Cir. Res. 73:1202-1207. Techniques for incorporating DNA into such expression systems are well known to those of ordinary skill in the art. The DNA may also be "naked," as described, for example, in Ulmer et al., 1993, Science 259:1745-1749 and reviewed by Cohen, 1993, Science 259:1691-1692. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Any of a variety of adjuvants may be employed in the vaccines of this invention. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Aid); Merck Adjuvant 65 (Merck and Company, Inc., Rahway, N.J.); aluminum salts such as aluminum hydroxide gel (alum) or aluminum phosphate; salts of calcium, iron or zinc; an insoluble suspension of acylated tyrosine acylated sugars; cationically or anionically derivatized polysaccharides; polyphosphazenes biodegradable microspheres; monophosphoryl lipid A and quil A. Cytokines, such as GM CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-γ, IL-2 and IL-12) tend to favor the induction of cell mediated immune responses to an administered antigen. In contrast, high levels of Th2-type cytokines (e.g., IL-4, IL-5, IL-6, IL-10 and TNF-β) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, 1989, Ann. Rev. Immunol. 7:145-173.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt MPL™ adjuvants are available from Corixa Corporation (see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555. Another preferred adjuvant is a saponin, preferably QS21, which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprises an oil-in-water emulsion and tocopherol. A particularly potent adjuvant formulation involving QS21, 3D-MPL and tocopherol in an oil-in-water emulsion is described in WO 95/17210. Another adjuvant that may be used is AS-2 (Smith-Kline Beecham). Any vaccine provided herein may be prepared using well known methods that result in a combination of antigen, immune response enhancer and a suitable carrier or excipient.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets HSV-infected cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have antiviral effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, Nature 392:245-251, 1998) and have been shown to be effective as a physiological adjuvant for eliciting prophylactic or therapeutic immunity (see Timmerman and Levy, Ann. Rev. Med. 50:507-529, 1999). In general, dendritic cells may be identified based on their typical shape (stellate in situ, with marked cytoplasmic processes (dendrites) visible in vitro) and based on the lack of differentiation markers of B cells (CD19 and CD20), T cells (CD3), monocytes (CD14) and natural killer cells (CD56), as determined using standard assays. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (Zitvogel et al., 1998, Nature Med. 4:594-600).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce maturation and proliferation of dendritic cells.

Dendritic cells are conveniently categorized as "immature" and "mature" cells, which allows a simple way to discriminate between two well-characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor, mannose receptor and DEC-205 marker. The mature phenotype is typically characterized by a lower expression of theses markers, but a high expression of cell surface molecules responsible for T cell activation such as class I and class II MHC, adhesion molecules (e.g., CD54 and CD11) and costimulatory molecules (e.g., CD40, CD80 and CD86).

APCs may generally be transfected with a polynucleotide encoding a polypeptide (or portion or other variant thereof) such that the polypeptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In aim and c<vivo transfection of dendritic cells, for example, may generally be performed using any methods known in the art, such as those described in WO 97/24447, or the gene gun approach described by Mahvi et al., 1997, Immunology and Cell Biology 75:456-460. Antigen loading of dendritic cells may be achieved by incubating dendritic cells or progenitor cells with the tumor polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in die presence of the polypeptide.

Administration of the Compositions

Treatment includes prophylaxis and therapy. Prophylaxis or treatment can be accomplished by a single direct injection at a single time point or multiple time points. Administration can also be nearly simultaneous to multiple sites. Patients or subjects include mammals, such as human, bovine, equine, canine, feline, porcine, and ovine animals. Preferably, the patients or subjects are human.

Compositions are typically administered in vivo via parenteral (e.g. intravenous, subcutaneous, and intramuscular) or other traditional direct routes, such as buccal/sublingual, rectal, oral, nasal, topical, (such as transdermal and ophthalmic), vaginal, pulmonary, intraarterial, intraperitoneal, intraocular, or intranasal routes or directly into a specific tissue.

The compositions are administered in any suitable manner, often with pharmaceutically acceptable carriers. Suitable methods of administering cells in the context of the present invention to a patient are available, and, although more than one route can be used to administer a particular cell composition, a particular route can often provide a more immediate and more effective reaction than another route.

The dose administered to a patient, in the context of the present invention should be sufficient to effect a beneficial therapeutic response in the patient over time, or to inhibit infection or disease due to infection. Thus, the composition is administered to a patient in an amount sufficient to elicit an effective immune response to the specific antigens and/or to alleviate, reduce, cure or at least partially arrest symptoms and/or complications from the disease or infection. An amount adequate to accomplish this is defined as a "therapeutically effective dose."

The dose will be determined by the activity of the composition produced and the condition of the patient, as well as the body weight or surface areas of the patient to be treated. The size of the dose also will be determined by the existence, nature, and extent of any adverse side effects that accompany the administration of a particular composition in a particular patient. In determining the effective amount of the composition to be administered in the treatment or prophylaxis of diseases such as HSV infection, the physician needs to evaluate the production of an immune response against the virus, progression of the disease, and any treatment-related toxicity.

For example, a vaccine or other composition containing a subunit HSV protein can include 1-10,000 micrograms of HSV protein per dose. In a preferred embodiment, 10-1000 micrograms of HSV protein is included in each dose in a more preferred embodiment 10-100 micrograms of HSV protein dose. Preferably, a dosage is selected such that a single dose will suffice or, alternatively, several doses are administered over the course of several months. For compositions containing HSV polynucleotides or peptides, similar quantities are administered per dose.

In one embodiment, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an antiviral immune response, and is at least 10-50% above the basal (i.e., untreated) level. Such vaccines should also be capable of causing an immune response that leads to an improved clinical outcome in vaccinated patients as compared to non-vaccinated patients. In general, for pharmaceutical compositions and vaccines comprising one or more polypeptides, the amount of each polypeptide present in a dose ranges from about 0.1 µg to about 5 mg per kg of host. Preferably, the amount ranges from about 10 to about 1000 µg per dose. Suitable volumes for administration will vary with the size, age and immune status of the patient, but will typically range from about 0.1 mL to about 5 mL, with volumes less than about 1 mL being most common.

Compositions comprising immune cells are preferably prepared from immune cells obtained from the subject to whom the composition will be administered. Alternatively, the immune cells can be prepared from an HLA-compatible donor. The immune cells are obtained from the subject or donor using conventional techniques known in the art, exposed to APCs modified to present an epitope of the invention, expanded ex vivo, and administered to the subject. Protocols for ex vivo therapy are described in Rosenberg et al., 1990, New England J. Med. 9:570-578. In addition, compositions can comprise APCs modified to present an epitope of the invention.

Immune cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to enrich and rapidly expand antigen-specific T cell cultures in order to generate a sufficient number of cells for immunotherapy. In particular, antigen-presenting cells, such as dendritic, macrophage, monocyte, fibroblast and/or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., 1997, Immunological Reviews 157:177).

Administration by many of the routes of administration described herein or otherwise known in the art may be accomplished simply by direct administration using a needle, catheter or related device, at a single time point or at multiple time points.

In Vivo Testing of Identified Antigens

Conventional techniques can be used to confirm the in vivo efficacy of the identified HSV antigens. For example, one technique makes use of a mouse challenge model. Those skilled in the art, however, will appreciate that these methods are routine, and that other models can be used.

Once a compound or composition to be tested has been prepared, the mouse or other subject is immunized with a series of injections. For example up to 10 injections can be administered over the course of several months, typically with one to 4 weeks elapsing between doses. Following the last injection of the series, the subject is challenged with a dose of virus established to be a uniformly lethal dose. A control group receives placebo, while the experimental group is actively vaccinated. Alternatively, a study can be designed using sublethal doses. Optionally, a dose-response study can be included. The end points to be measured in this study include death and severe neurological impairment, as evidenced, for example, by spinal cord gait. Survivors can also be sacrificed for quantitative viral cultures of key organs including spinal cord, brain, and the site of injection. The quantity of virus present in ground up tissue samples can be measured. Compositions can also be tested in previously infected animals for reduction in recurrence to confirm efficacy as a therapeutic vaccine.

Efficacy can be determined by calculating the $IC_{50}$, which indicates the micrograms of vaccine per kilogram body weight required for protection of 50% of subjects from death. The $IC_{50}$ will depend on the challenge dose employed. In addition, one can calculate the $LD_{50}$, indicating how many infectious units are required to kill one half of the subjects receiving a particular dose of vaccine. Determination of the post mortem viral titer provides confirmation that viral replication was limited by the immune system.

A subsequent stage of testing would be a vaginal inoculation challenge. For acute protection studies, mice can be used. Because they can be studied for both acute protection and prevention of recurrence, guinea pigs provide a more physiologically relevant subject for extrapolation to humans. In this type of challenge, a non-lethal dose is administered, the guinea pig subjects develop lesions that heal and recur. Measures can include both acute disease amelioration and recurrence of lesions. The intervention with vaccine or other composition can be provided before or after the inoculation, depending on whether one wishes to study prevention versus therapy.

Methods of Treatment and Prevention

The invention provides a method for treatment and/or prevention of HSV infection in a subject. The method comprises administering to the subject a composition of the invention. The composition can be used as a therapeutic or prophylactic vaccine. In one embodiment, the HSV is HSV-2. Alternatively, the HSV is HSV-1. The invention additionally provides a method for inhibiting HSV replication, for killing HSV-infected cells, for increasing secretion of lymphokines having antiviral and/or immunomodulatory activity, and for enhancing production of herpes-specific antibodies. The method comprises contacting an HSV-infected cell with an immune cell directed against an antigen of the invention, for example, as described in the Examples presented herein. The contacting can be performed in vitro or in vivo. In a preferred embodiment, the immune cell is a T cell. T cells include CD4 and CD8 T cells. Compositions of the invention can also be used as a tolerizing agent against immunopathologic disease.

In addition, the invention provides a method of producing immune cells directed against HSV. The method comprises contacting an immune cell with an HSV polypeptide of the invention. The immune cell can be contacted with the polypeptide via an antigen-presenting cell, wherein the antigen-presenting cell is modified to present an antigen included in a polypeptide of the invention. Preferably, the antigen-presenting cell is a dendritic cell. The cell can be modified by, for example, peptide loading or genetic modification with a nucleic acid sequence encoding the polypeptide. In one embodiment, the immune cell is a T cell. T cells include CD4 and CD8 T cells. Also provided are immune cells produced by the method. The immune cells can be used to inhibit HSV replication, to kill HSV-infected cells, in vitro or in vivo, to increase secretion of lymphokines having antiviral and/or immunomodulatory activity, to enhance production of herpes-specific antibodies, or in the treatment or prevention of HSV infection in a subject.

Methods of Detecting HSV Infection

The invention also provides methods and kits for detecting HSV infection in a subject. In one embodiment, the diagnostic assay can be used to identify the immunological responsiveness of a patient suspected of having a herpetic infection and to predict responsiveness of a subject to a particular course of therapy. The assay comprises exposing T cells of a subject to an antigen of the invention, in the context of an appropriate APC, and testing for immunoreactivity by, for example, measuring IFNγ, proliferation or cytotoxicity. Suitable assays are described in more detail in the Examples.

In one embodiment, the invention provides a for detecting HSV infection in a subject, wherein the method comprises contacting a biological sample obtained from the subject with a polypeptide of the invention; and detecting the presence of a binding agent that binds to the polypeptide in the sample, thereby detecting HSV infection in the biological sample. Examples of biological samples include, but are not limited to, whole blood, sputum, serum, plasma, saliva, cerebrospinal fluid and urine. In one embodiment, the kit comprises a polypeptide of the invention in combination with a detectable marker. In another embodiment, the kit comprises a monoclonal antibody or a polyclonal antibody that binds with a polypeptide of the invention.

In another embodiment, the method for detecting HSV infection comprises obtaining a biological sample from a subject, and contacting the sample with at least two oligonucleotide primers in a polymerase chain reaction, wherein at least one of the oligonucleotide primers is specific for a polynucleotide of the invention. The method further comprises detecting a polynucleotide sequence that amplifies in the presence of the oligonucleotide primers in the sample. In one embodiment, the oligonucleotide primer comprises at least about 10 contiguous nucleotides of a nucleic acid sequence disclosed herein, or of a sequence that hybridizes thereto. Alternatively, the method can comprise contacting the sample with an oligonucleotide probe specific for a polynucleotide of the invention, and detecting in the sample a nucleic acid sequence that hybridizes to the oligonucleotide probe. In one embodiment, the oligonucleotide probe comprises at least about 15 contiguous nucleotides of a nucleic acid sequence disclosed herein, or a sequence that hybridizes thereto.

EXAMPLES

The following examples are presented to illustrate the present invention and to assist one of ordinary skill in making and using the same. The examples are not intended in any way to otherwise limit the scope of the invention. Details of the methods used herein are further described in Koelle et al., 2002, J. Clin. Invest. 110(4):537-48; and Koelle et al., 2001, J. Immunol. 166:4049-4058.

Example 1

Expression of Cutaneous Lymphocyte-Associated Antigen and Functional E-Selectin Ligand by CD8+ T-Cells Specific for a Skin-Tropic Virus This example demonstrates the use of herpes simplex virus type 2 (HSV-2) as a model system to investigate CD8+ T-cell trafficking to the skin in humans. Using HLA class I tetramers, the example shows that HSV-specific CD8+ T-cells in the peripheral blood express high levels of cutaneous lymphocyte-associated antigen (CLA). In contrast, CD8+ T-cells specific for non skin-tropic herpes viruses lacked CLA expression. CLA-positive HSV-2-specific CD8+ T-cells had the characteristics of central memory cells, expressing CCR7, CD62L, and CD28, and proliferate briskly in response to antigen. CLA is related to a functional E-selectin ligand and both E-selectin and CLA-positive cells were detected in HSV-2 infected skin. HSV-2-specific T-cells were found to adhere to cells transfected with E-selectin. A higher proportion of HSV-specific CD8+ T-cells recovered from herpes lesions express CLA compared with blood, consistent with a role for CLA in skin homing. This is the first report of expression of tissue-specific adhesion-associated molecules by virus-specific CD8+ T-cells. The evaluation of vaccines for skin and mucosal pathogens should include study of the induction of appropriate tissue-specific homing molecules.

Fluorescent HLA tetramers were used to detect CD8+ cells specific for the HSV-2 virion proteins 22 (VP22) and 13/14 (VP13/14) and HSV-2-infected cell protein 0 (ICP0). As controls, T-cells specific for cytomegalovirus (CMV) tegument protein pp 65, and the Epstein-Barr virus EBV) protein BMLF-1, were also studied. The majority of memory HSV-2-specific T-cells in the blood expressed CLA, while CMV- and EBV-specific T-cells lacked CLA expression. Recurrent herpetic skin biopsies showed up-regulated E-selectin expression and contained a CLA-expressing dermal infiltrate locally enriched in HSV-specific CD8+ T-cells. These data suggest that homing receptor expression on memory T-cells may be programmed by the site of original antigen encounter, promoting migration for immune surveillance or responses to reactivation of infection. Additional studies indicated that circulating CLA+ HSV-2-specific CD8+ T-cells have a preserved capacity for self-renewal and the characteristics of central memory T-cells.

Methods

Subjects and specimens. Subjects were human leukocyte antigen (HLA) typed. Subjects used for HSV-2 analyses were HSV-2 seropositive, HIV-1 seronegative, generally healthy, and not taking immune-suppressive medication. For subjects with a clinical history of genital herpes, the first clinical episode had occurred at least six months prior to phlebotomy. No subject was experiencing a symptomatic recurrence of genital herpes or receiving antiviral therapy at the time of phlebotomy. HSV-2-seropositive subjects filled out a questionnaire concerning their history of genital herpes. Some subjects had daily HSV cultures of multiple genital and peri-rectal sites on a daily basis for >50 consecutive days to determine their rates of HSV shedding. PBMC were cryopreserved after Ficoll-Hypaque centrifugation. For CD62L, flow cytometry used freshly isolated PBMC. For two subjects, biopsies of peri-anal HSV-2 culture-positive lesions and forearm normal skin were performed. Portions were frozen in OCT (Sakura, Torrance, Calif.). Subjects used for EBV and CMV analyses were healthy lab personnel known to be seropositive for these agents and to have appropriate HLA types. Protocols were IRB approved and conducted according to Declaration of Helsinki principles.

Cells and viruses. PBMC were re-stimulated with peptide, IL-2, and IL-7 in T-cell medium (TCM), or alternatively in TCM with 1.6 µg/ml phytohaemagglutinin (PHA-P, Remel, Lenexa, Kans.) and 64 units/ml human natural IL-2 (Hemagen, Columbia, Md.) beginning on day three. To test tetramer B7-RPR, peptide-stimulated cells (day 12) were stained with tetramer and FITC-conjugated anti-CD8α clone MHCD0801 (Caltag, Burlingame, Calif., sorted (FACSVantage, Becton Dickinson, San Jose, Calif.), rested overnight in TCM with 50 U/ml IL-2 (Chiron, Emeryville, Calif.), cloned at 1 cell/well and expanded, and tested for cytotoxicity (see below). Skin-derived lymphocytes were expanded from biopsies in TCM with PHA-P and human natural IL-2 beginning on day three for 10-14 days. HSV-2 strain 333 and HSV-1 strain E115 were grown and titrated in Vero cells.

HSV-2 CD8+ T-cell epitopes. HLA restriction was assigned by transfection/infection of Cos-7 cells with B*0702 cDNA/HSV-2, co-culture with 5491.2000.81, and measurement of IFN-γ secretion by ELISA. A library of Sau3a I-digested HSV-2 strain HG52 DNA was interrogated by co-transfection with HLA B*0702 cDNA using the Cos-7/IFN-γ readout. The positive library "hit" encoded amino acids 306 to 825 of ICP0. Epitope localization was done by C-terminal truncation analysis with nested PCR-generated fragments originating at amino acid 306. Transfection/IFN-γ readout was used to narrow the epitope to amino acids 708-778. Algorithms predicted HLA B*0702 binding by amino acids 743-751.

Lymphocyte assays. Four-hour, triplicate cytotoxicity assays used 51Cr release and an effector:target ratio of 20:1 unless otherwise indicated. Target infection used a multiplicity of 10 for 18 hours; peptides were loaded for 90 minutes at 37° C. prior to washing. Spontaneous release was less than 25%. To measure adhesion, CHO or CHO-E cells were plated at 2×106/60 mm diameter dish. The next day, 1×106 peptide-stimulated (eight days) or 2×106 un-stimulated PBMC were added. Dishes were rotated (50 RPM, one hour, 37° C.). Unbound cells and cells from a PBS wash were pooled to form the unbound fraction. Bound cells were collected with chilled PBS, 4 mM EDTA and vigorous pipetting. Microscopy confirmed removal of lymphocytes. Fractions were washed and processed for flow cytometry. Results are expressed as the proportion of CD8-high cells that bind tetramer in the bound fraction divided by the proportion of similar cells in the unbound fraction.

Tetramers. Phycoerythrin-labeled tetramers from the NIAID core facility at Emory University were HLA B*0702-RPR(HSV-2 protein VP22 amino acids 49-57) and HLA B*0702-APA (HSV-2 protein ICP0 amino acids 743-751), and the previously described tetramer A*0201-GLA, which binds T-cells specific for HSV-2 protein VP13/14, amino acids 551-559. Tetramer A*0201-NLV, which binds T-cells specific for CMV pp 65 595-603 (NLVPMVATV; SEQ ID NO: 13), was produced according to published methods. Briefly, HLA A*0201 heavy chain or β2-microglobulin were produced in E. coli. The heavy chain was truncated to contain the extracellular domain. A substrate sequence for BirA biotinylation was added at the COOH terminus. HLA complexes were folded using 30 mg of heavy chain, 25 mg of β2-microglobulin, and 10 mg of peptide. Biotinylatation used BirA at 5 mg/ml, 0.5 mM biotin, and 5 mM ATP for 16 hours at room temperature. Biotinylated complexes were purified by HPLC, and tetramers assembled by mixing biotinylated complexes with streptavidin-phycoerythrin at a 4:1 molar ratio. Tetramers A*0201-CLG, specific for EBV LMP2 426-434, and A2-VLE, specific for CMV 1E-1 316-324 were produced similarly by Proimmune, Oxford, United Kingdom. Phycoerythrin-labeled tetramer A*0201-GLC, specific for EBV BMLF-1 280-288, has been described.

Flow cytometry. For detection of HSV- or EBV-specific T-cells, 1–5×10$^6$ cryopreserved, thawed PBMC, or ~2×10$^5$ cultured cells, were stained with 1 µg phycoerythrin-labeled tetramer in 50 µl TCM at 20° C. for one hour. 20 µl anti-CD8α-Cychrome or 20 µl anti-CD8α-PerCP and 20 µl FITC-labeled anti-CLA mAb HECA-452 or FITC-labeled anti-CD62L (Pharmingen, San Diego, Calif.) were added for 30 minutes at 4° C., followed by washes and fixation. For CCR7, tetramer was followed by 2 μg anti-CCR7 clone 2H4 (Pharmingen), washes, and then FITC-labeled goat anti-mouse (Southern Biotechnologies, Birmingham, Ala.). For CMV-specific T-cells, 5×105 PBMC were incubated with 10 μg/ml tetramer in 20 μl PBS/20% FCS for 20 minutes at 37° C. Cells were washed, incubated at 4° C. for 30 minutes with 20 μl anti-CD8-PerCP (Becton Dickinson) and anti-CLA-FITC, washed, and fixed. Cells were analyzed with a FACScan or FACScalibur (Becton Dickinson) and WinMDI 2.8 software (http://facs.scripps.edu). CD8+ T-cells were lymphocytes (forward/side scatter) intensely staining with anti-CD8 cc. Tetramer binding was expressed as the percentage of CD8α-high cells with bright (usually >102 fluorescence units) tetramer staining. CLA positivity was defined from the FL1/cell number histogram for all lymphocytes at the junction between negative cells and a "tail" of FL1-brighter events, typically at 101.0 to 101.1 fluorescence units. Two-color analyses used FITC-conjugated anti-CD8α (Caltag, Burlingame, Calif.) after the tetramer. Selected T-cell clones were stained with anti-TCR αβ-FITC (Becton Dickenson, San Jose, Calif.) per the manufacturer's directions. To document expression of E-selectin, CHO and CHO-E cells were stained with 10 μg/ml anti-CD62E (Becton Dickinson) or isotype control at 4° C. for 30 minutes, washed, stained with 2 μl phycoerythrin-labeled goat anti-mouse (Biomeda, Hayward, Calif.) for 30 minutes at 4° C., washed, and fixed.

Immunohistochemistry. Frozen, four μM sections were acetone-fixed, quenched (4:1 methanol:hydrogen peroxide) and stained. Briefly, E-selectin was detected with anti-CD62E (see above) followed by isotype-specific peroxidase-conjugated secondary antibody and ABC peroxidase kit with 3,3' diaminobenzidine substrate (Vector, Burlingame, Calif.). CLA was detected using biotin-conjugated mAb HECA-452 (PharMingen), anti-biotin mAb MB-9100@1:200 (Vector) and detection as above. To control for nonspecific binding, staining was performed with isotype-matched primary antibodies specific for irrelevant antigens. Sections were counterstained with Mayer's haematoxylin.

Statistics. Expression of surface antigens were compared between tetramer staining and non-staining CD8+ lymphocytes by Mann-Whitney test, two-tailed.

Results

Detection of HSV-2-specific CD8+ T-cells in PBMC. Whether HSV-2-specific CD8+ T-cells in the blood would express a characteristic pattern of cell surface molecules involved in cell trafficking was examined by developing tools to identify HSV-specific T-cells. An HLA B*0702 tetramer, B7-RPR, was folded with peptide VP22 49-57 from the HSV-2 UL49 open reading frame. This tetramer specifically stained the HLA B7-restricted T-cell clone 5491.2000.48 isolated from a cutaneous HSV-2 lesion (FIG. 6). To confirm that this tetramer bound HSV-2-specific CTL, PBMC from a HSV-2 infected, B*0702 subject were stimulated with VP22 49-57, sorted on the basis of tetramer binding and CD8+ expression, and cloned by limiting dilution. Resultant clones had specific cytotoxicity (FIG. 6).

To obtain an additional marker of the HSV-2-specific CD8+ response, the fine specificity of CD8+ clone 5491.2000.81, also recovered from a HSV-2 skin lesion, was determined. The epitope was found to be amino acids 743-751 of the immediate early viral protein ICP0 (FIG. 6). An HLA B*0702 tetramer, B7-APA, was constructed and specifically bound clone 5491.2000.81 (FIG. 6).

The frequency of CD8+ T-cells for these HSV-2 epitopes was then examined in PBMC from HSV-2 seropositive, HLA B*0702-expressing adults with symptomatic genital herpes for 0.5 to 29 years duration (Table 3). Six of 11 subjects had VP22 49-57-specific CD8+ cells in their PBMC. From 0.11% to 0.60% of CD8α-high lymphocytes stained with tetramer B7-RPR (FIG. 6). Control PBMC from control HSV-2 infected, HLA B*0702 (−) persons and HSV-uninfected, HLA B*0702 (+) persons had <0.01% tetramer-positive CD8+ cells.

TABLE 3

Characteristics of the HSV-2-infected subjects.

| Subject | Duration of hsv-2 infection[a] | Recurrences/year[b] | Shedding rate[c] |
|---|---|---|---|
| 10521 | 11 | not avail. | 10.5 |
| 10292 | 0.5 | not avail. | not avail. |
| 4196 | 17 | not avail. | 26.1 |
| 10026 | 29 | 0 | not avail. |
| 5491 | 26 | 10 | not avail. |
| 6376 | unknown[D] | 0 | 0 |
| 10433 | 16 | 10 | 1.4 |
| 5101 | 17 | 12 | 31.7 |

[a]Years between the first clinical episode of a syndrome consistent with genital herpes and phlebotomy.
[b]Derived from subject self-report about the number of episodes of genital ulceration in the six months prior to enrollment.
[c]Percentage of days during which any anogenital anatomic site was positive for HSV-2 by culture during >50 consecutive days of sampling.
[D]Subject is HSV-2 seropositive but has no history consistent with genital herpes.

Figure 7:
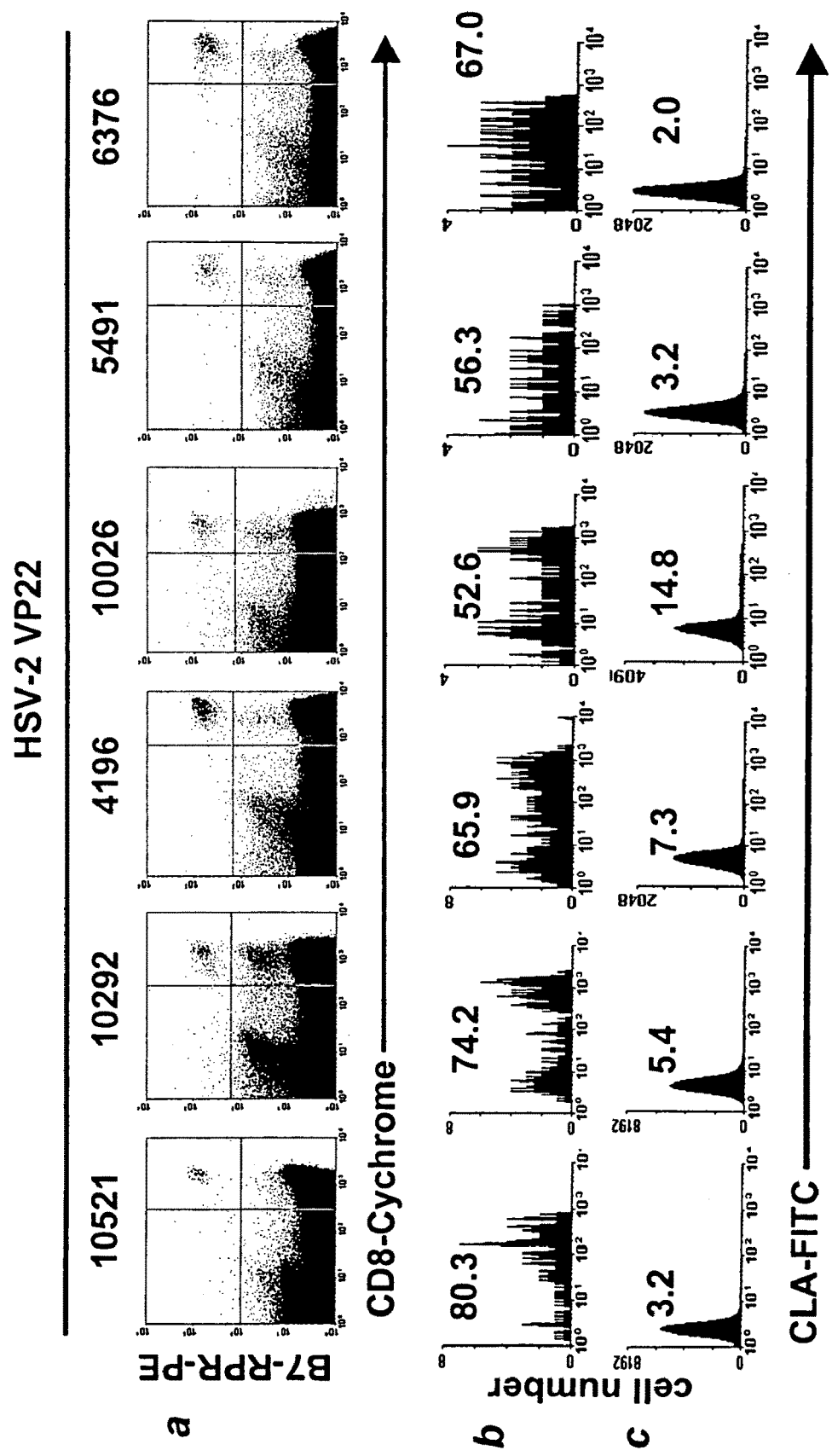
FIGS. 7A-7F. CLA expression by circulating CD8+ lymphocytes specific for three human herpes viruses. For HSV-2-specific T-cells, unique subject ID numbers are indicated below the HSV-2 antigens.
Figure 7:
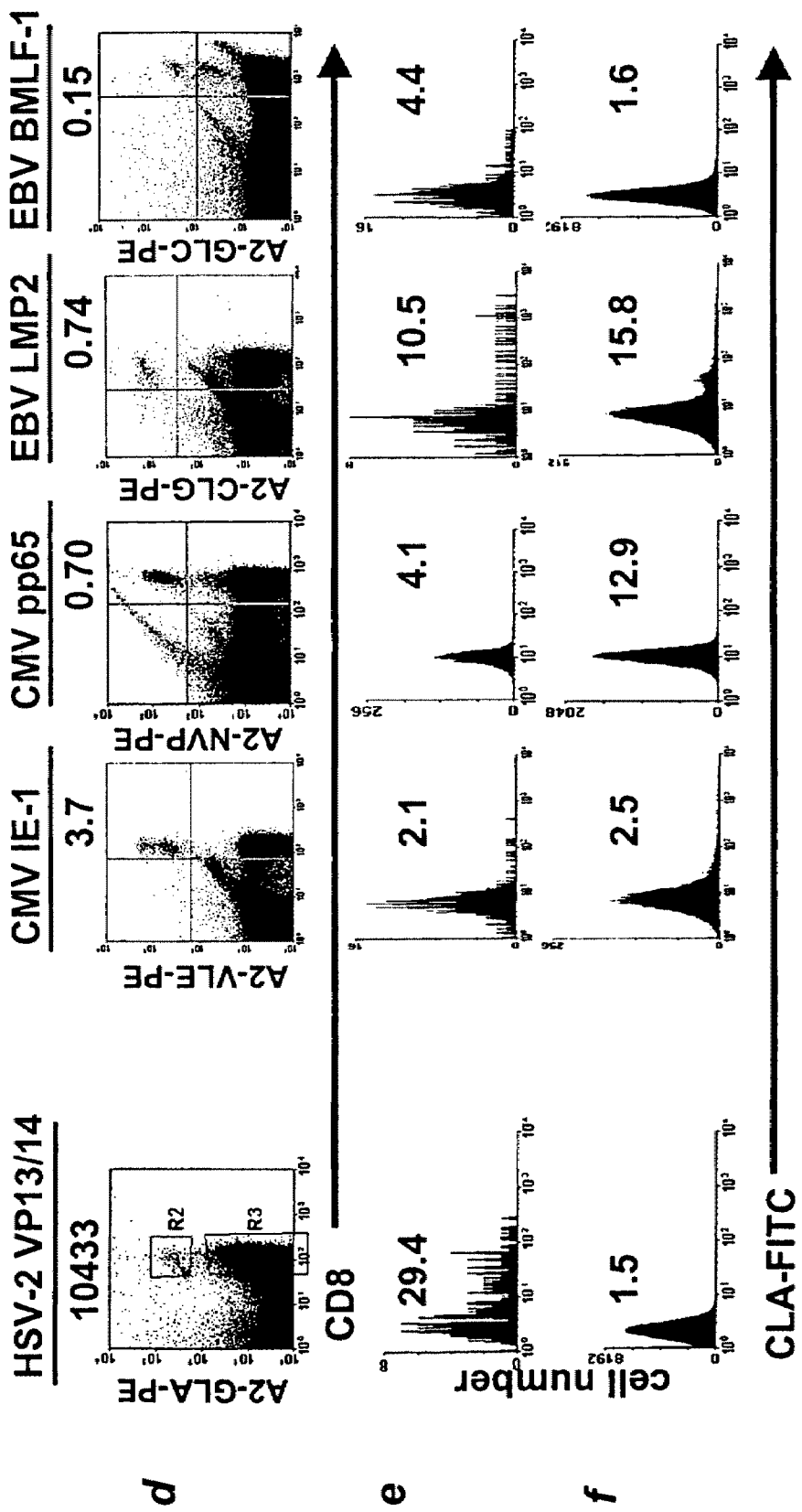

CLA expression by circulating virus-specific memory CD8+ cells. CIA was expressed by 52.6% to 80.3% of circulating CD8α-high cells that stained with tetramer B7-RPR (mean±SD, 66.0±10.4) (FIG. 7). Only 2.0% to 14.8% of tetramer-negative CD8+ cells from these same subjects expressed CLA (mean±SD, 6.0±4.3). For a HSV-2 epitope in protein VP13/14, 29.4% of CD8α-high cells staining with the previously described tetramer A2-GLA expressed CLA, in comparison to 1.5% of tetramer-negative CD8+ cells. In this small study, no association was observed between the proportion of VP22-specific CD8+ T-cells that expressed CLA (FIG. 7) and the severity of HSV-2 infection (Table 3).

CLA expression by HLA A*0201-restricted CD8+ cells specific for either CMV or EBV was examined. For each virus, two independent epitopes were studied. Expression of CIA by EBV- and CMV-specific CD8+ cells was low, and generally similar to that of tetramer-negative CD8+ cells (examples in FIG. 7). A similar pattern was noted for each subject and each epitope (Table 4 summarizes the entire data set). For CMV, the mean±SD for the expression of CLA by virus-specific and bystander CD8+ cells were 7.5%±5.1% and 7.7%±3.6%, respectively. For EBV, CLA was expressed by 5.2%±3.1% of EBV-specific cells and 5.4%±4.2% of other CD8+ cells, respectively.

TABLE 4

CLA expression by EBV- and CMV-specific CD8+ T-cells in PBMC.

| | | | | CLA expression by CD8 (+) cells | |
|---|---|---|---|---|---|
| Subject | Virus | Tetramer | Tetramer (+)[a] | Tetramer (+) | Tetramer (−) |
| 1 | CMV | A2-NVP | 0.70 | 4.1 | 12.9 |
| 2 | CMV | A2-NVP | 6.6 | 5.1 | 6.0 |
| 3 | CMV | A2-NVP | 0.51 | 5.6 | 2.7 |
| 4 | CMV | A2-NVP | 0.33 | 2.9 | 3.4 |
| 5 | CMV | A2-VLE | 3.7 | 2.1 | 2.5 |
| 6 | CMV | A2-VLE | 0.47 | 17.5 | 11.1 |
| 7 | CMV | A2-VLE | 2.3 | 11.1 | 9.5 |
| 8 | CMV | A2-VLE | 0.98 | 10.4 | 7.8 |
| 9 | EBV | A2-GLC | 0.11 | 1.2 | 2.7 |
| 10 | EBV | A2-GLC | 0.15 | 4.4 | 1.6 |

TABLE 4-continued

CLA expression by EBV- and CMV-specific CD8+ T-cells in PBMC.

| | | | | CLA expression by CD8 (+) cells | |
|---|---|---|---|---|---|
| Subject | Virus | Tetramer | Tetramer (+)[a] | Tetramer (+) | Tetramer (−) |
| 11 | EBV | A2-CLG | 0.57 | 7.2 | 6.2 |
| 12 | EBV | A2-CLG | 0.74 | 10.5 | 15.8 |

[a]Percentage of CD8α-high cells that stain with the indicated tetramer.

Figure 8:
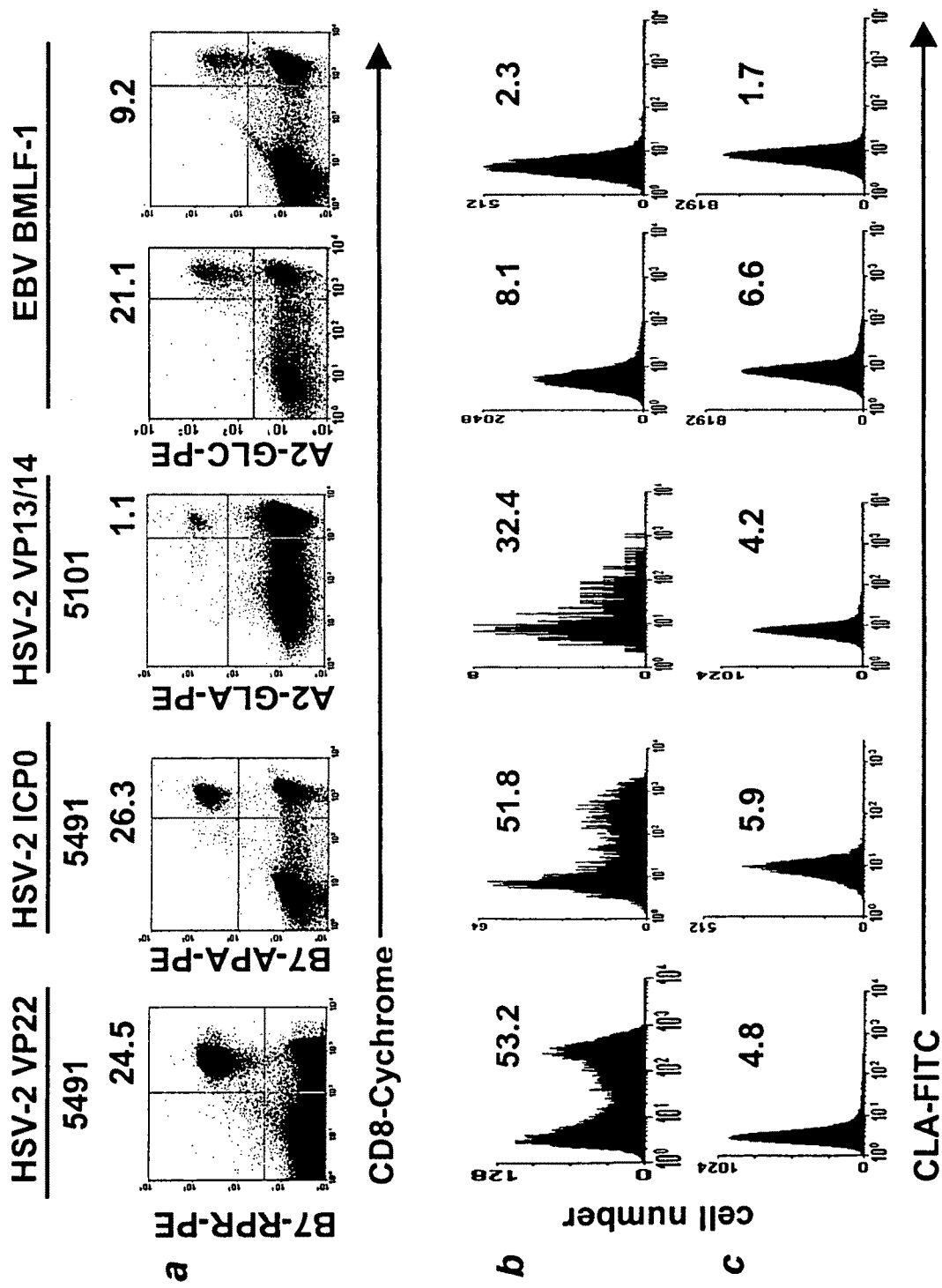
FIGS. 8A-8C. Expression of CLA by in vitro re-stimulated herpesvirus-specific CD8+ T-cells. For HSV-2-specific T-cells, unique subject ID numbers are indicated below the HSV-2 antigens.

Proliferative capacity and phenotype of circulating HSV-2-specific CD8+ cells. The above data indicate that HSV-2-specific memory CD8+ T-cells express the skin-associated adhesion molecule, CLA, while still in the circulation. Circulating cells specific for VP22 49-57, VP13/14 551-559, or ICP0 743-751 were able to expand briskly in vitro in response to one re-stimulation with specific HSV-2 peptide (FIG. 8). The proportions of VP22- and % VP13/14-specific cells that expressed CLA were similar before and after their peptide-driven expansion (FIGS. 7 and 8). The proportion of V-113/14-specific CD8+ T-cells expressing CLA was somewhat lower than the proportion of VP22-specific T-cells. This comparison could not be made for ICP0, as the cells were not abundant enough to identify in un-manipulated PBMC. The same peptide re-stimulation protocol did not induce CLA expression by EBV-specific cells. These results are consistent with a model in which lineages of CLA-expressing and CLA-negative HSV-2-specific cells can proliferate in vitro, although shifts in phenotype during the expansion of initially CLA-expressing and CLA-negative cells, or shorter-term fluctuations during progression through the cell cycle, cannot be ruled out.

Figure 9:
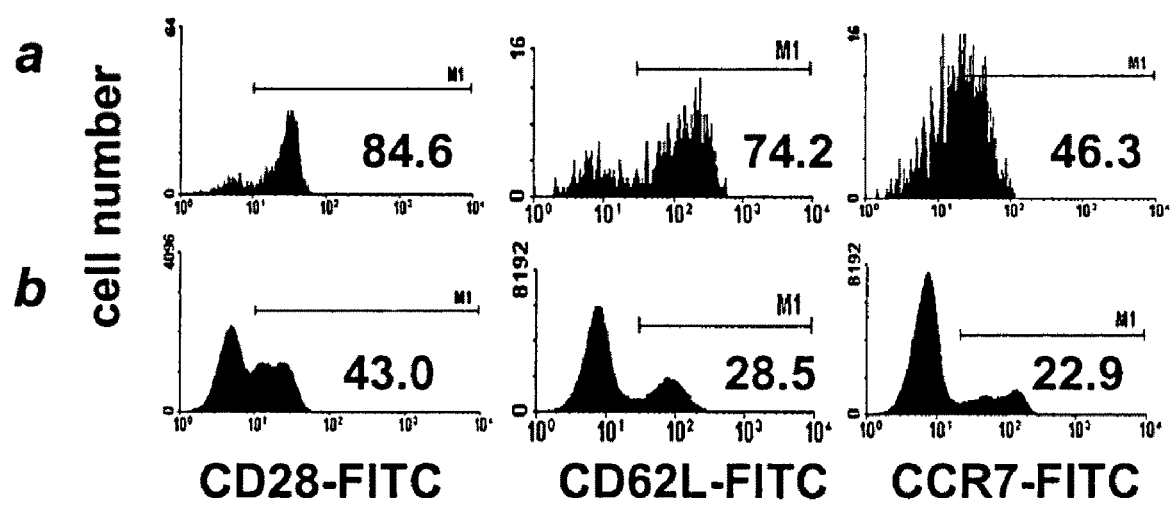
FIGS. 9A-9B. Expression of cell surface antigens by circulating HSV-2-specific CD8+ T-cells.

It has been reported that circulating CD8+ cells can be divided into central memory cells expressing CD62L and CCR7 which can traffic to lymph nodes, and effector memory cells, lacking CD62L and CCR7 but expressing cytolytic molecules. Effector memory cells may have a reduced replicative potential. Circulating VP22-specific cells were >50% CD62L (+) for four of the five subjects studied (Table 5 and FIG. 9). CCR7 expression varied from 46% to 89%. VP22-specific cells were also >80% CD28 (+) from each donor, correlating with their ability to expand in vitro (Table 5). Each of these markers was more highly expressed by VP22-specific cells than by CD8α-high lymphocytes with other specificities (Table 5). Comparison between tetramer and non-tetramer staining CD8+ groups reached statistical significance (P=0.009) for CD28 expression, but not for CCR7 or CD62L for these small groups. These results are consistent with most HSV-2-specific CD8+ T-cells specific for VP13/14 49-57 having the central memory phenotype. The concept of central memory can be extended to include CD8+ T-cells that have acquired the ability to selectively home to sites of antigenic challenge.

TABLE 5

Phenotype of CD8α-high cells in PBMC analyzed by binding of tetramer B7-RPR, which identifies cells specific for HSV-2 VP22 49-57.

| | CD28 | | CD62L | | CCR7 | |
|---|---|---|---|---|---|---|
| Subject | B7-RPR (+) | B7-RPR (−) | B7-RPR (+) | B7-RPR (−) | B7-RPR (+) | B7-RPR (−) |
| 10521 | 92.6 | 55.2 | 82.6 | 49.7 | 75.9 | 31.2 |
| 4196 | 84.6 | 43 | 74.2 | 28.5 | 46.3 | 22.9 |
| 10026 | 95 | 80.4 | 35.5 | 49.7 | 88.7 | 64 |
| 5491 | 95.7 | 30.6 | 79.5 | 44.6 | 53.4 | 32.7 |
| 6376 | 98.6 | 46.7 | 53 | 47 | 50.1 | 43.2 |
| 10292 | 80.9 | 76.4 | nd | nd | nd | nd |
| mean ± SD | 91.2 ± 6.9 | 55.4 ± 19.5 | 65.0 ± 20.1 | 43.9 ± 8.9 | 62.9 ± 18.5 | 38.8 ± 15.8 |

CLA and CLA ligand expression by T-cells infiltrating genital HSV-2 lesions. To explore the possible role of CLA-associated E-selectin ligand in the migration of HSV-specific CD8+ T-cells to herpetic lesion, skin biopsy tissue was obtained from a HLA B*0702-expressing person. Because too few cells were available from skin biopsies for direct analysis, skin-infiltrating cells were expanded with PHA and IL-2, which provides a fairly uniform replication stimulus to most T and NK cells. HSV-2-specific T-cells were locally enriched among cells expanded from a HSV-2 culture-positive lesion obtained on the third day of symptoms compared to cells expanded from normal skin and cells in un-manipulated PBMC. 6.4% of CD8α-high cells from a HSV-2 biopsy were specific for VP22 amino acids 49-57 (FIG. 10), compared to 0.1% for normal skin and 0.21% from blood obtained the day of biopsy, representing a 60-fold local enrichment at the site of infection. 2.3% of lesion-infiltrating CD8α-high cells were specific for HSV-2 ICP0 743-751, while the level in normal skin was 0.06% and the level in blood was below the limit of detection. Circulating cells with this specificity were detectable after peptide re-stimulation (FIG. 8). Similar results for both T-cell specificities were obtained from a biopsy of a recurrent HSV-2 lesion obtained two months after the first, again, both local enrichment and almost universal (>90%) CLA expression was noted. To rule out non-specific induction of CLA expression during replication of skin-derived T-cells in vitro, PBMC from four donors were expanded for 11 days with the culture conditions used for skin biopsies. CLA was expressed by 4.5±2.3% of CD8α-high cells, similar to fresh PBMC.

Figure 10:
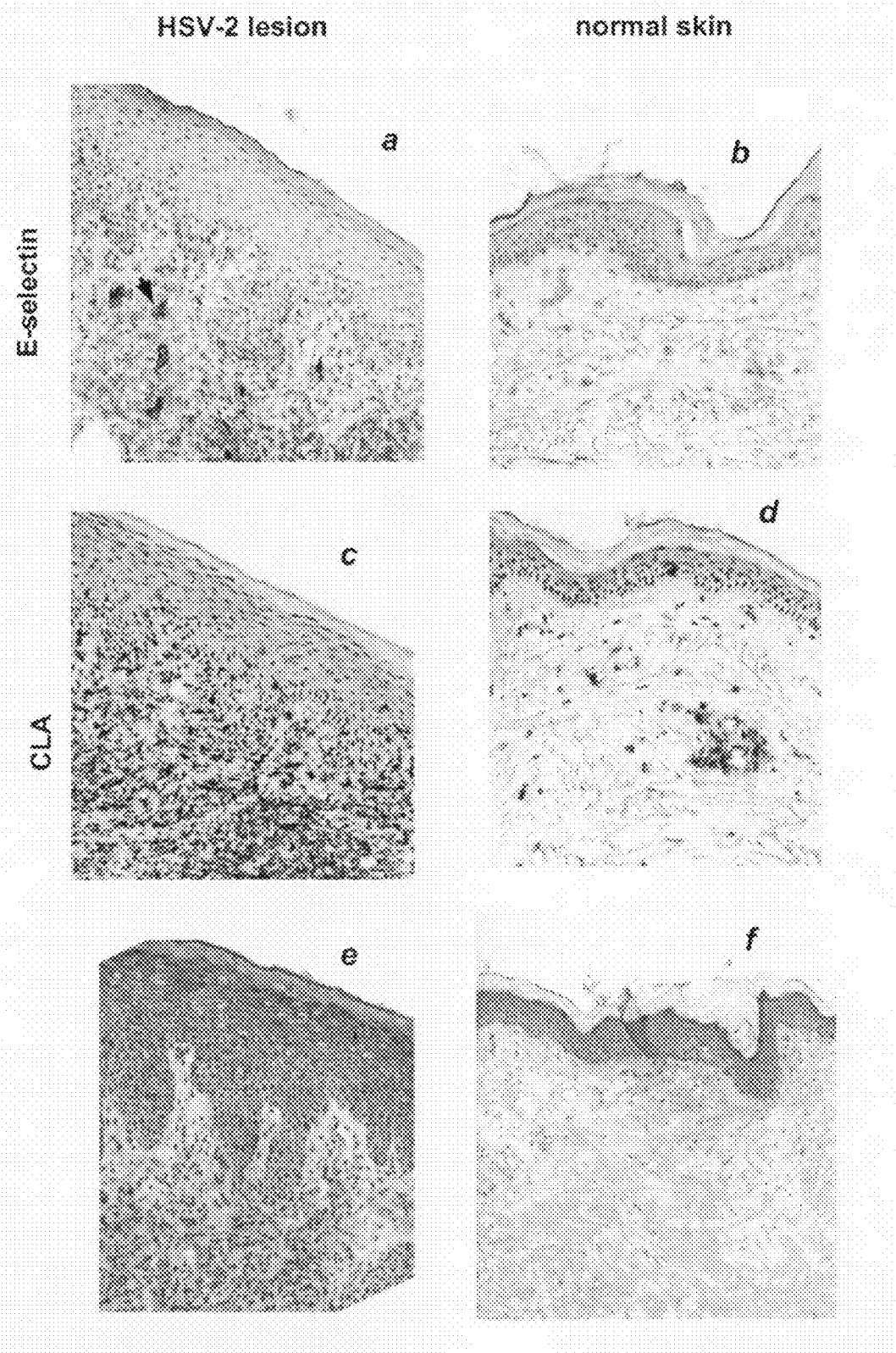
FIGS. 10A-10I. CLA and CLA-ligand expression in skin and by lesion-derived cells.
Figure 10:
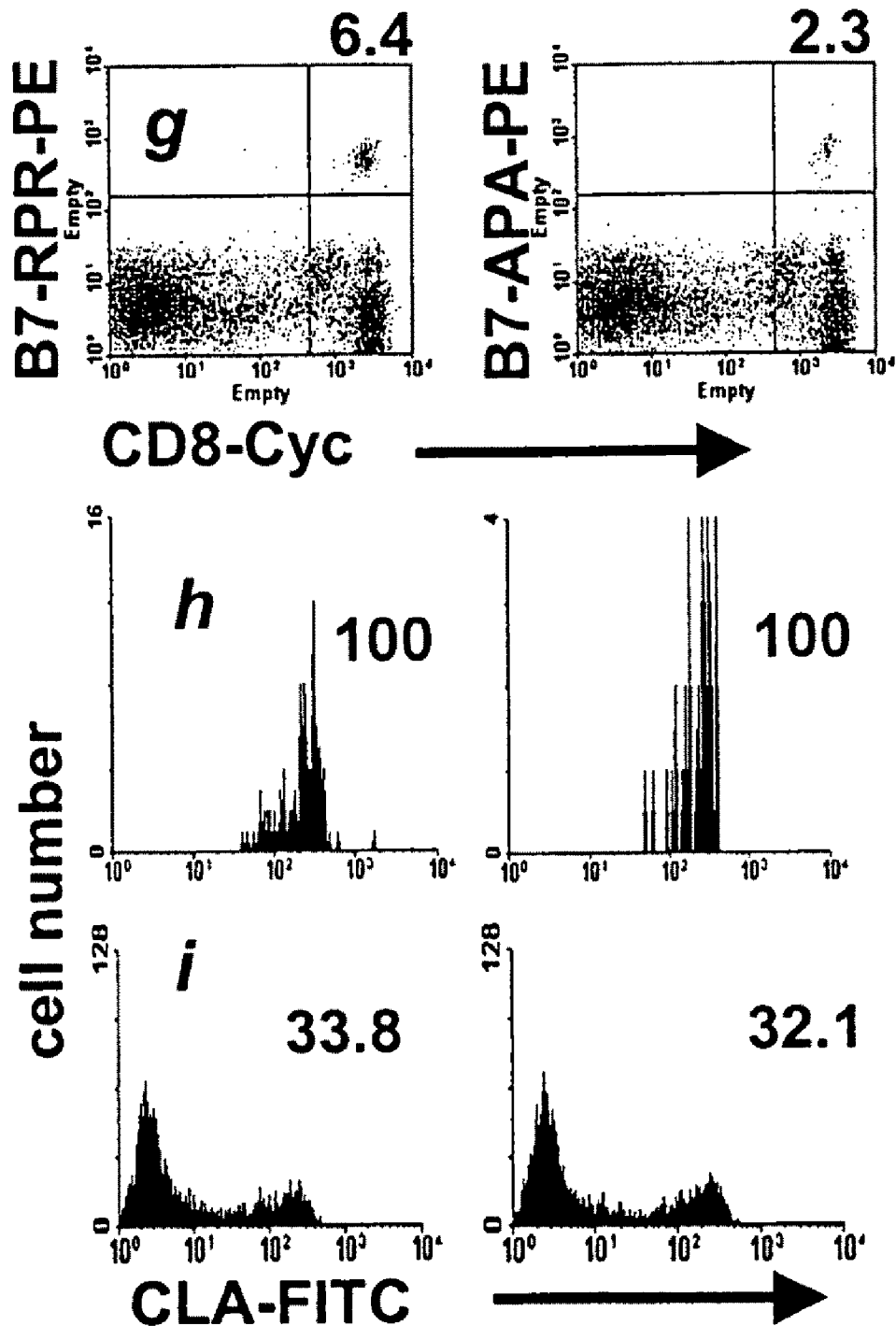

CLA expression by HSV-2-specific T-cells derived from different sites was compared. HSV-2-specific cells in PBMC displayed a broad distribution of CLA expression including some CLA-negative cells (FIG. 7). HSV-specific cells from the herpetic lesion were uniformly CLA-positive (FIG. 10). The tetramer-negative CD8+ lymphocytes from these cultures also displayed a higher level (~30%) of CLA expression than did similar cells from PBMC (FIG. 7).

Immunohistologic examination of a HSV-2 culture positive buttock lesion from subject 5491, obtained on day three of symptoms of recurrent genital herpes, showed that about 30% of small dermal mononuclear cells stained with anti-CLA antibody. E-selectin was strongly expressed in a dermal venular pattern (FIG. 10). In normal skin, E-selectin staining showed a less intense venular pattern, while CLA-positive cells were rarely observed. The presence of CLA and E-selectin in HSV-2-infected skin supports suggests that a CLA-associated E-selectin ligand, and E-selectin, may participate in leukocyte trafficking to recurrent HSV-2 lesions.

Binding of CLA-expressing, HSV-specific cells to E-selectin. To determine if CLA expression by circulating HSV-2-specific CD8+ T-cells was associated with functional binding to E-selectin, PBMC from three HSV-2 infected, HLA B7 subjects were incubated with E-selectin-expressing CHO-E cells, which uniformly expressed E-selectin, or control CHO cells, which lacked expression. Measurement of the proportion of CD8α-high cells that were tetramer B7-RPR+ in the bound and unbound fractions indicated that T-cells specific for HSV-2 VP22 49-57 were enriched about 10-fold by CHO-E binding (Table 6). HSV-specific CD8+ T-cell lines generated in vitro by re-stimulation with the HSV-2 peptide (FIG. 9) were also tested. Again, HSV-2-specific cells detected with fluorescent HLA tetramers were selectively bound by CHO-E cells, but not control CHO cells.

control of ganglionic infection, the maintenance of neuronal latency, and in protection against infectious challenge in murine models. HSV evades CD8+ T-cells by inhibiting TAP and degrading host mRNA. The tetramer-based measurements in this example reveal higher levels of circulating HSV-2-specific CD8+ T-cells than previously observed with limiting dilution CTL assays. In particular, high levels of VP22-specific CD8+ T-cells were detected. VP22 may be recognized efficiently due to its delivery into the class I antigen processing pathway prior to TAP inhibition, and without a requirement for endogenous synthesis, or due to its efficient intercellular spread, which can mediate CTL adjuvant activity.

In this example, HSV-2-specific T-cells were studied before and after trafficking from the circulation to HSV-2

TABLE 6

Binding of virus-specific CD8+ lymphocytes to E-selectin. Cells were analyzed by flow cytometry before or after one hour incubation with CHO cells expressing E-selectin or control CHO cells.

| Subject | Stimulation | Virus | Tetramer | Input[a] | CHO-E-selectin enrichment[b] | CHO enrichment[b] |
|---|---|---|---|---|---|---|
| 5491 | none[c] | HSV-2 | B7-RPR | 0.14 | 10.1 | 1.1 |
| 4196 | none[c] | HSV-2 | B7-RPR | 0.26 | 5.6 | 0.7 |
| 6376 | none[c] | HSV-2 | B7-RPR | 0.19 | 13.2 | 0.8 |
| 5491 | VP22 49-57 | HSV-2 | B7-RPR | 23.6 | 9.5 | 1.1 |
| 5491 | ICP0 743-751 | HSV-2 | B7-APA | 12.4 | 8.3 | 1.3 |

[a]Percentage of CD8α-high cells that bind tetramer in the cells used for binding assays.
[b]Ratio of the percentages of CD8α-high cells that bind tetramer in the bound and unbound fractions of cells after one hour of rotary co-incubation with CHO-E or CHO monolayers.
[c]Un-manipulated PBMC were thawed, washed, and used for binding experiments. Phlebotomy for subject 4196 was a different date from specimens used for FIG. 6 and FIG. 7.

Discussion

This is the first description of the selective expression of a putative tissue-specific homing molecule by circulating microbe-specific CD8+ T-cells. The cell surface expression and functional data in this example are consistent with a role for a CLA-associated E-selectin ligand in the trafficking of circulating HSV-2-specific memory CD8+ T-cells to skin during recurrent genital herpes. Because many patients with genital herpes have lesions on keratinized epithelial surfaces of the external genitalia, perineum, back, or legs, CLA expression by HSV-2-specific T-cells is anatomically appropriate.

In common with HSV-2, EBV and CMV undergo intermittent reactivations and are episodically shed in infectious form by most immunocompetent, infected individuals. In contrast to HSV-2, neither primary nor recurrent infection with EBV or CMV are associated with cutaneous infection. The most common site of EBV shedding is the oropharynx, while the most common sites of CMV shedding are uterine cervix, urine, and oropharynx. Reactivations of EBV and CMV in immunocompetent persons are usually asymptomatic. Reactivations of EBV and CMV are intermittent, brief, and anatomically unpredictable, complicating the assessment of the possible influence of reactivation status on homing receptor expression at the time of phlebotomy. Expression by CD8+ T-cells specific for EBV and CMV was similar to the background level of 5-10% observed for circulating CD8+ lymphocytes.

HSV-specific CD8+ T-cells are functionally important in containing HSV-2 infection. Levels of CD8+ CTL correlate inversely with the severity of HSV-2 in HIV-HSV-2 co-infected men and correlate temporally with the local clearance of HSV-2 in lesions. CD8+ CTL are also important in the infected skin. MelanA-specific CD8+ T-cells in PBMC from subjects with vitiligo express higher levels of CLA than do similar cells from normal subjects. In atopic subjects, proliferative responses to allergy-associated antigens are enriched among CLA+CD4+ T-cells. Few reports have examined homing receptor expression by circulating virus-specific T-cells. Circulating memory rotavirus-specific CD4+ cells preferentially express the adhesion molecule A4B7 integrin. The data described herein indicate that memory CD8+ T-cells specific for the skin-tropic herpesvirus HSV-2 express CLA prior to leaving the circulation.

E-selectin expression is expressed at low basal levels in non-inflamed skin, and is increased in diverse skin inflammatory conditions. Apparent up-regulation of E-selectin in HSV-2-infected tissue was observed. This is not surprising, since IFN-γ, IL-1β and TNF-α, which are up-regulated in HSV lesions, cooperate to increase E-selectin expression by endothelial cells. Additional work is required to document the magnitude and time course of up-regulation. Lymphocytes infiltrating the dermis commonly express CLA. The influx of HSV-2-specific CD4+ cells and of NK cells into recurrent HSV-2 lesions precedes the inflow of HSV-2-specific CD8+ T-cells. The proportion of HSV-2-specific CD8+ T-cells that express CLA appears to be higher in the skin than the blood (FIG. 10). The ~50-80% of circulating HSV-2-specific cells which express CLA (FIG. 7) may preferentially migrate to skin, or the local microenvironment may further promote CLA expression.

The finding that circulating HSV-2-specific memory cells express CLA implies that expression of this antigen is up-regulated during the priming of naïve HSV-2-specific CD8+ T-cells, or at a subsequent stage of conditioning. Expression of α(1,3)-fucosyltransferase VII (FVII) is a probable key regulator of CLA expression, although control over other glycosyltransferases and the primary polypeptide backbone, PSGL-1 may also be important. In vivo, CLA is expressed by cells co-expressing CD45RA and CD45RO in skin-draining lymph nodes, consistent with up-regulation during the priming of naïve T-cells. In a murine model, skin-homing-associated selectin ligands are up-regulated during cutaneous priming. It is rational to hypothesize that inflammatory cytokines and local antigen presenting cells could influence CLA expression during priming.

In this cross-sectional study, the proportion of HSV-2 VP22-specific CD8+ T-cells that expressed CLA was relatively constant in the set of six subjects (FIG. 7). Two more HLA B*0702-bearing persons who are HSV-2 seropositive but with no clinical history of genital herpes have been studied. Staining of un-manipulated PBMC with tetramer B7-RPR showed that 54.5% and 62.10% of tetramer-high, CD8α-high cells expressed CLA, similar to the six subjects shown in FIG. 7. No obvious segregation of CLA expression by HSV-2-specific CD8+ T-cells by the clinical or virologic (shedding) severity of HSV-2 infection was observed (Table 3, FIG. 7). Similarly, it is not yet known if CLA expression by HSV-2-specific cells in the periphery fluctuates temporally in association with symptomatic or asymptomatic recurrences of HSV-2.

In summary, subjects with recurrent, symptomatic HSV-2 infection have readily detectable circulating VP22-specific CD8+ T-cells that express CLA. CLA is tightly associated with functional E-selectin binding activity, which is an anatomically appropriate property for HSV-2-specific T-cells. HSV-specific CD8+ T-cells in PBMC expressed functional E-selectin binding activity. Neither CLA expression nor E-selectin binding was noted for responses to CMV or EBV, two non skin-tropic herpes viruses. Accordingly, the vaccines and immunotherapies for HSV disclosed herein would not only elicit specific T-cells, but also guide these T-cells to express appropriate homing molecules. More broadly, preventative and therapeutic T-cell based treatments can be optimized if the identity, mechanisms of action, and control mechanisms for homing molecules is understood and manipulated.

Example 2

Immunodominance Amongst Herpes Simplex Virus-Specific CD8 T-Cells Expressing a Tissue-Specific Homing Receptor This Example shows a novel approach to create unbiased panels of CD8 cytotoxic T lymphocyte clones specific for herpes simplex virus type 2. Circulating herpes simplex virus type 2-specific cells were enriched and cloned after sorting for expression of the skin-homing receptor, cutaneous lymphocyte-associated antigen, bypassing re-stimulation with antigen. The specificity of every resultant cytotoxic clone was determined. Clonal frequencies were compared with each other and the total number of cytotoxic clones. For each subject, the specific CD8 cytotoxic T-lymphocyte response was dominated by T-cells specific for only a few peptides. Newly described antigens and epitopes in viral tegument, capsid, or scaffold proteins were immunodominant in some subjects. Clone enumeration analyses were confirmed in some subjects with bulk T-cell cultures using herpes simplex mutants and vaccinia recombinants. This example demonstrates that, during chronic infection with herpes simplex virus type 2, the CD8 T-cell response becomes quite focused, despite the presence of many potential antigenic peptides.

Methods

Subjects and specimens. Subjects were human immunodeficiency virus type 1 (HIV-1) seronegative, HSV-2 seropositive, generally healthy, and not taking immune suppressive medication or anti-HSV therapy or experiencing symptomatic reactivations of HSV at the time of specimen collection. All subjects had documented HSV-2 infection for longer than one year. PBMC were isolated from peripheral blood by Ficoll centrifugation and cryopreserved. Some subjects completed daily sampling for the detection of HSV shedding as described. Cultures showing cytopathic effect were confirmed as HSV-2 by immunofluorescence. HLA typing used DNA or serologic methods.

TABLE 7

Subjects studied in Example 2.

| Subject | Age, sex | HSV infections | Years HSV-2 infection* | Shedding rate† | Recurrences/year‡ |
|---|---|---|---|---|---|
| 1 | 33, F | 1, 2 | 13 | 0 | 1 |
| 2 | 35, F | 2 | 15 | 2.7 | 5 |
| 3 | 21, F | 2 | 13 | 0 | 0 |
| 4 | 35, F | 2 | 16 | 1.4 | 1 |
| 5 | 39, M | 2 | Unknown§ | 0.6 | 1 |
| 6 | 43, F | 1, 2 | 26 | ND | 3 |
| 7 | 63, F | 2 | 48 | ND | 1 |
| 8 | 38, F | 2 | 17 | 31.7 | 3 |
| 9 | 28, F | 2 | 5 | 16.9 | 0 |
| 10 | 49, F | 1, 2 | 4 | 5.3 | 2 |
| 11 | 35, F | neither | NA | NA | NA |

*Years between the first clinical episode of a syndrome consistent with genital herpes and phlebotomy, rounded off to the nearest whole year.
†Percentage of days during which any anogenital anatomic site was positive for HSV-2 by culture during consecutive days of sampling.
‡Subject self-report in the six months prior to enrollment.
§Subject tested HSV-2 seropositive, has no history of genital herpes, but recognized typical lesions after study entry.
ND = not done.
NA = not applicable.

Cells, viruses, and antigens. Epstein Barr virus-transformed B cells (EBV-LCL) were cultured as described. Vero and BSC40 cells were cultured in DMEM-α with 10% heat-inactivated FCS, L-glutamine, and penicillin-streptomycin. HSV-2-reactive, protein virion protein (VP)-16-specific CD4+ clone 1A.B.25.1 has been described. To enrich HSV-specific CTL, thawed PBMC were washed in TCM* (RPMI 1640 with 25 mM Hepes, 1% penicillin-streptomycin, 2 mM L-glutamine (Invitrogen, Carlsbad, Calif.), 10% heat-inactivated human serum (Serologicals Corporation, Norcross, Ga.), and 10 µg/ml ciprofloxacin. Cells ($5 \times 10^6$) were stained per the manufacturer's directions with FITC-labeled anti-CLA and PE*-labeled anti-CD28 (Pharmingen, San Diego, Calif.), and PE-Cy5*-labeled anti-CD8 cc (Caltag, Burlingame, Calif.). Cells were sorted (FacsVantage II, Becton Dickenson, San Jose, Calif.) gating on $CD8^{high}$ $CD28^+$ lymphocytes with bright ($>10^{1.6}$ fluorescence units) or negative ($<10^{1.0}$ fluorescence units) staining for CIA. $CD8^{intermediate}$ (NK) cells were excluded. For cloning, the cells were rested overnight in 200 µl TCM with 50 U/ml human IL-2 (Chiron), and cloned. Clones of interest were expanded using anti-CD3 mAb and IL-2. For bulk expansion, sorted $CD8^{high}$ $CD28^+$ $CLA^{bright}$ or $CD8^{high}$ $CD28^+$ $CLA^{negative}$ cells (~200-500 cells/well) were stimulated with PHA and IL-2 in 96-well U-bottom plates with same protocol used for cloning, combined into larger wells as needed, and tested after 14-20 days.

Recombinant vaccinia expressing immediate early protein ICP* 27 of HSV-2 has been described. Vaccinia expressing full-length HSV-2 strain 333 open reading frame UL*47 and UL49 were created by standard methods using vaccinia strain Western Reserve and targeting vector pSC11. Full-length HSV-2 genes were cloned for this purpose by PCR. Expression of HSV-2 proteins by recombinant vaccinia was confirmed in lymphocyte functional assays using protein-specific T-cell clones (see Results). Vaccinia stocks were made by infecting 75 cm² monolayers of BSC-40 cells at MOI* 1 for 2-3 days and sonicating scraped cells in 2.0 ml of their supernatant. Virus was titrated on BSC-40 cells. For lymphoproliferation assays, aliquots of vaccinia or HSV strains were UV irradiated (10 cm from GT-038 bulbs for 30 minutes) and used at 1:100 final concentration.

CTL assays used HSV-2 strain 333 and HSV-1 strain E115. Viruses with disrupted or repaired UL47, the ORF encoding VP*13/14, were made by homologous recombination. A fragment of HSV-2 DNA encoding amino acids 500-695 of VP13/14, the intergenic region, and the N-terminal portion of VP11/12 (gene UL46) was generated by PCR with primers GAC<u>GCTAGC</u>CACGACCGTCTGGAGGTACT (SEQ ID NO: 14) and GAC<u>TCTAGA</u>GCGACCGTTACCCTG AAATA (SEQ ID NO: 15) (Nhe I and Xba I sites underlined) and cloned after Nhe I/Xba I digestion into similarly digested pcDNA3.1 (−) (Invitrogen). A fragment encoding the C-terminal portion of VP16 (gene UL48) was amplified with primers GAC<u>TCTAGA</u>GACGAGGAAAGGGGTGGT (SEQ ID NO: 16) and GAC<u>AAGCTT</u>CCGCTCCTCTG GGTACTTTA (SEQ ID NO: 17) and cloned, after Xba I/Hind III digestion, into the plasmid generated above digested with Xba I/Hind III. HSV-2 strain HG52 was used as template. A DNA fragment encoding enhanced green fluorescent protein and bacterial guanosine phosphoribosyl transferase with promoters was cloned into the Xba I site of this second construct. The resultant targeting vector has the UL47 promoter and DNA encoding amino acids 1-499 of VP13/14 deleted. DNA linearized with Nhe I/Hind III, organic extracted, and alcohol precipitated was electroporated into Vero cells, followed by infection with HSV-2 HG52. Bulk product virus was plated on Vero cells. A green fluorescing plaque, del47, was triple-plaque purified. To rescue UL47, the HSV-2 HG52 Bgl II i fragment was linearized with Bgl II and electroporated into Vero cells, followed by infection with del47. Bulk product virus was plated on HGPRT(−) STO cells and revertants selected with 6-thioguanine. A resultant non-fluorescent plaque, 47rev, was triple plaque-purified. Southern blots used standard techniques, PCR-generated probes from UL46, UL47, and green fluorescent protein, and viral DNA prepared from infected Vero cells.

HSV-2 CD8 T-cell epitope discovery. An expression cloning system based on genomic HSV-2 DNA libraries, as documented for epitopes in VP22, VP13/13, and ICP0, was used. In brief, the HLA restricting alleles of novel HSV-2-specific CD8 clones (above) were determined in CTL assays with panels of partially HLA class I-matched EBV-LCL as APC*. Confirmation of correct assignment of restricting alleles was obtained by transfection of Cos-7 cells with HLA class I cDNA and infection with HSV-2 as described. HLA B*5701, B*2705, and B*1402 cDNAs were obtained by RT-PCR using total RNA (Trizol, Invitrogen) from subjects' EBV-LCL as starting material, using a specific primer for reverse transcription. The resultant cDNA, paired specific primers with distal restriction endonuclease sites, and a proof-reading thermostable DNA polymerase were used for PCR as described. PCR products were cloned into pcDNA3.0 (Invitrogen), fully sequenced, and compared to a database. HLA A*0101 cDNA in pcDNA3.1 was obtained from the 13th IHWG Gene Bank.

To interrogate the HSV-2 genome for T-cell epitopes, Cos-7 cells were co-transfected with the relevant HLA class I heavy chain cDNA and a library of Sau3a I-digested HSV-2 strain HG52 DNA. This method uses IFN-γ secretion to detect T-cell activation. Positive library pools were decoded in a reiterative process to yield single antigenic HSV-2 fragments. The positive library "hits" were sequenced (Big Dye 3.0, ABI, Foster City, Calif.) and compared (nBLAST) to HSV-2 HG52 to identify the antigenic region. In one case a fragment of HSV-2 gene UL7 encoding amino acids 50-192 was identified from the primary library. PCR-generated fragments encoding amino acids 50-150 and 150-192 were generated with appropriate primers, ligated to the pcDNA3.1-His vector predicted to yield an in-frame fusion protein product, and both fragments tested by co-transfection with HLA cDNA into Cos-7 as described. In a case in which a fragment of HSV-2 DNA predicted to contain portions of unique short open reading frame (US) 8 and US8.5 and all of US9 was identified from the primary library, full-length HSV-2 ORFs US8.5 and US9 PCR-cloned into pcDNA 3 and full-length HSV-2 US8 from strain HG52 cloned into pcDNA 3.1-His were tested separately by co-transfection with HLA cDNA as described. To help find candidate peptide epitopes, relevant regions of HSV-1 and HSV-2 predicted amino acid sequences were aligned. For each HSV-2-reactive T-cell clone, reactivity with HSV-1 in CTL assays was used to prioritize areas of HSV-2 peptide sequence for detailed workup. HLA binding motifs were then used to find peptides predicted to bind the relevant HLA class I molecule. Peptides were synthesized with free termini as described.

Lymphocyte functional assays. Cytotoxicity was tested in 4-hour $^{51}$Cr release assays. Clones were screened in singlicate or duplicate using autologous EBV-LCL targets with or without infection with HSV-2. Bulk T-cell lines and established clones were tested in triplicate at effector to target ratios of 20:1 unless specified. Targets were infected with HSV-2 strains at MOI 10 or vaccinia at MOI 5 for 18-20 hours, or incubated with 1 μM peptide for 90 minutes at 37° C. prior to washing. The congenic parent HSV-2 strain HG52 was used with UL47 mutants. Spontaneous release was usually less than 25%. Blocking mAb specific for HLA DR, HLA DP, or HLA DQ (clones L243, B7.21, or SPTL3, respectively) were used as 1:4 hybridoma supernatants; anti-HLA class I mAb (clone W6/32) was added at 10 μg/ml. IFN-γ release was measured by ELISA after exposure of T-cell clones for 24 hours to APC; either to transfected Cos-7, as described, or to 2.5×10⁴ mock- or HSV-2 infected autologous B-cells in 96-well U-bottom plates in 200 μl RPMI 1640 with HEPES, pen-strep, L-glutamine, and 10% FCS. LCL were pre-infected for 18 hours at MOI 10 and mAb W6/32 used during co-cultivation at 10 μg/ml. Proliferation assays (triplicate) used ³H thymidine incorporation with 10⁴ cloned responder T-cells, 10⁵ autologous irradiated PBMC as APC per well, and UV-irradiated virus with addition of label 72 hours after setup and harvesting 18 hours later.

Flow cytometry. To validate the cloning of HLA B*2705 and B*1402 cDNA, expression was checked by transfection of Cos-7 cells and flow cytometry using allele-specific mAb (One Lambda) as described. T-cell clones were stained with PE or allophycocyanin-labeled tetrameric complexes of HLA B*0702 and VP22 49-57 (B7-RPR), HLA A*0201 and VP13/14 551-559 (A2-GLA), or HLA A*0201 and VP13/14 289-298 (A2-FLV), obtained from the Tetramer Facility of the National Institutes of Allergy and Infectious Diseases, followed by anti-CD8 FITC or anti-CD8-PE-Cy5 (Caltag) as described. T-cell clones were stained with directly labeled mAb specific for human CD4, CD8α, CD3, or a combination of CD16 and CD56, as previously described or with unlabeled murine mAb to human CD16 or CD56 (Pharmingen) followed by FITC-labeled goat anti-mouse IgG (Sigma) per the manufacturer's directions.

Results

Figures 11A, 11B:
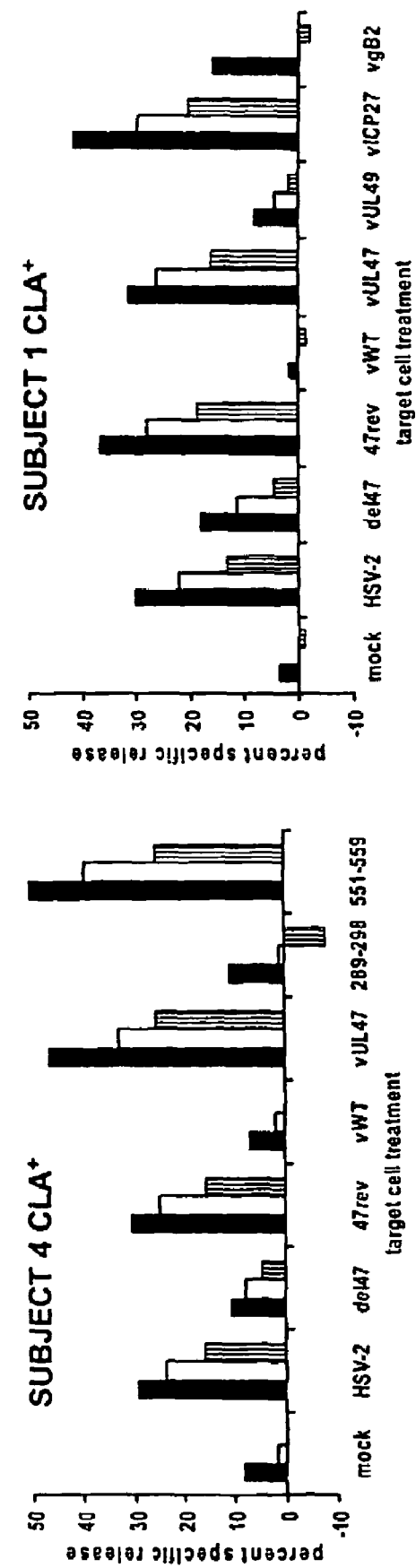
FIGS. 11A-11D. Cytotoxicity of PBMC from donor 4 (FIGS. 11A and 11C) and 1 (11B and 11D), sorted into CD8+ CD28+ CLAhigh (11A and 11B) or CD8+ CD28+ CLAlow (11C and 11D) fractions, and expanded with PHA and IL-2. Effectors were tested against autologous EBV-LCL targets infected with the indicated viruses, or pulsed with VP13/14 peptides amino acids 289-298 or 551-559. Results are percent specific release from CTL assays at effector to target ratios of 40 (solid bars), 20 (open bars) or 10 (vertical striped bars).
Figure 11D:
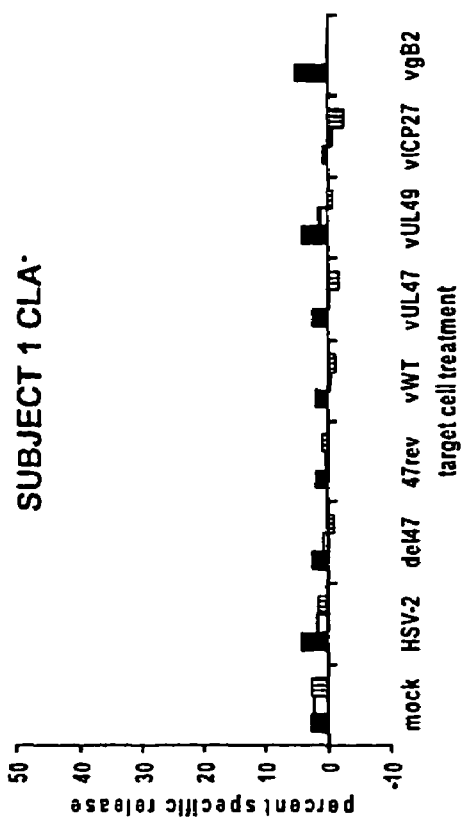
Figure 11C:
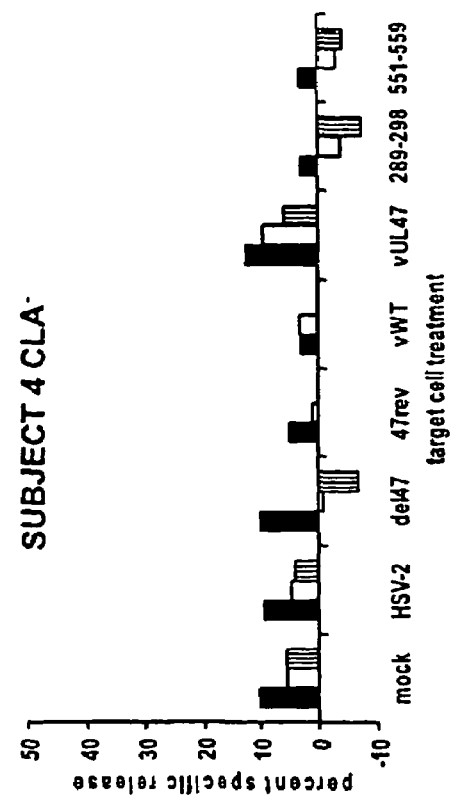

Circulating HSV-2-specific CTL express CLA. Circulating CD8 T-cells specific for HSV-2 epitopes in the viral tegument proteins VP13/14 and VP22 have been observed, and the non-structural protein ICP0, expresses CLA. VP13/14-specific T-cells were CD28$^+$. To determine whether HSV-2-specific CTL were preferentially present in the CLA$^+$ fraction of CD8$^+$ PBMC, CD8$^+$, CD28$^+$ cells expressing either high or low levels of CLA were evaluated, sorted and polyclonally expanded, and subsequently tested for HSV-2-specific cytotoxicity. Virus-specific killing was only observed in the CLA$^{high}$ cells (FIG. 11). In contrast, CLA$^{low}$ cells did not show detectable cytotoxicity at effector to target ratios of up to 40:1.

The expression of CLA by HSV-2-specific CD8 T-cells was also examined by direct cloning. CD8$^+$, CD28$^+$, CLA$^{high}$ cells were cloned with a non-specific mitogen shortly after sorting from whole PBMC. Among 10 consecutively studied HSV-2 infected adults, HSV-2-specific CD8 CTL clones were derived from nine persons. Overall, 14.8% of clones derived from the CLA$^{high}$ fractions were HSV-2-specific, with a range from 0 to 31.5%/within individual subjects and a mean of 10.5% (Table 8). The number of HSV-2-specific CTL clones recovered per subject ranged from 2 to 95. No HSV-2-specific clones were recovered from one person seronegative for HSV-1 and HSV-2.

TABLE 8

Clones derived from CD8+ CD28+ CLA$^{high}$ PBMC with HSV-2-specific CTL activity.

| Subject | Clones screened | CTL clones* | Percent CTL clones |
|---|---|---|---|
| 1 | 241 | 76 | 31.5 |
| 2 | 319 | 95 | 29.8 |
| 3 | 86 | 14 | 16.3 |
| 4 | 64 | 4 | 6.2 |
| 5 | 96 | 6 | 6.2 |
| 6 | 84 | 5 | 5.9 |
| 7 | 288 | 10 | 3.5 |
| 8 | 194 | 6 | 3.1 |
| 9 | 93 | 2 | 2.1 |
| 10 | 12 | 0 | 0 |
| 11† | 58 | 0 | 0 |

*Clones with greater than 25% specific release for autologous HSV-2-infected B-cell targets and <10% specific release for autologous uninfected targets.
†Seronegative for HSV-1 and HSV-2, control subject.

Figure 12:
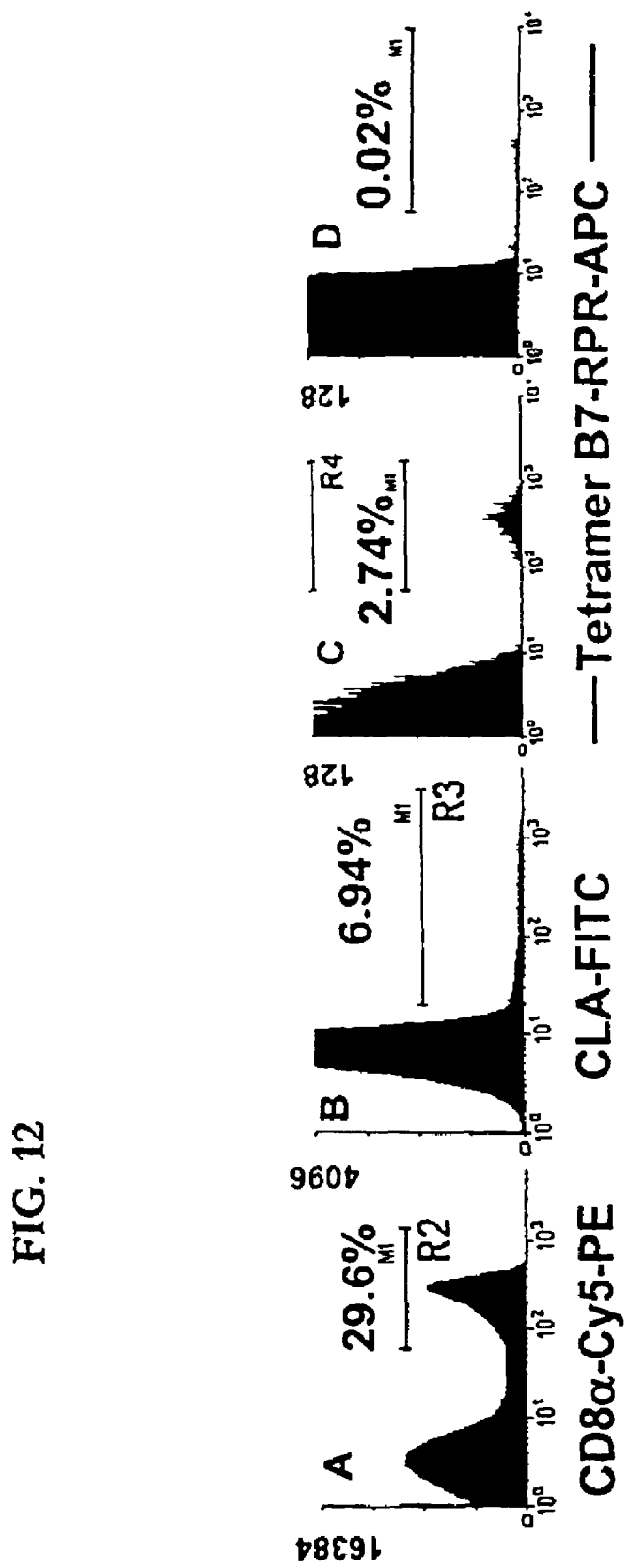
FIGS. 12A-12D. Enrichment of HSV-2-specific cells in the circulating CLA$^{high}$ compartment, presented as histograms of cell number vs. fluorescence intensity after sequential, multi-reagent staining.

Data consistent with enrichment of HSV-2-specific CD8 T-cells in the CLA-positive fraction of PBMC were also obtained by directly staining of PBMC. PBMC from HLA B*0702-positive, HSV-2 infected persons were gated for CD8 and CLA expression and analyzed for binding of tetramer B7-RPR, which stains cells specific for an epitope in the HSV-2 tegument protein VP22. In one example (subject 5), 29.6% of circulating lymphocytes were CD8α$^{high}$, and 6.9% of these were CLA$^+$. Among CD8α$^{high}$, CLA$^+$ cells, 2.74% stained with tetramer B7-RPR (FIG. 12); CD8α$^{high}$ CLA$^-$ cells were only 0.02% tetramer-positive. Among six HLA B7$^+$/HSV-2 infected persons, between 0.42% and 2.74% percent of CLA$^{high}$ CD8$^{high}$ lymphocytes were positive for this single HSV-2 specificity. Much lower levels of tetramer staining were observed among CD8$^{high}$, CLA$^{low}$ lymphocytes (all <0.05%). Taken together, the CTL activity in bulk and clonal CLA$^{high}$, CD8 T cells, and the segregation of tetramer binding and CLA expression, were consistent with the observation that HSV-2-specific CD8 CTL of diverse specificity express CLA in persons with chronic HSV-2 infection.

Definition of HSV-2 CD8 T-cell antigens and epitopes. To determine patterns of dominance and complexity within the CD8 CTL response to HSV-2, the fine specificity of each available HSV-2-specific CD8 T-cell clone was determined. For subjects 1 and 2, from whom large numbers of CTL clones were detected (Table 8), an unselected subset of well-growing clones were selected for detailed work-up. For the other subjects, the fine specificities of all or most of the HSV-specific clones that successfully expanded in cell culture (90-100% of those detected in screening assays) were determined Clones restricted by HLA A*0201 or B*0702 were initially checked for reactivity with epitopes in VP13/14, VP22, ICP0, or glycoprotein D2, and an A*0201-restricted epitope in glycoprotein gB2, amino acids 443-451, known to be restricted by these alleles. Several subjects yielded clones reactive with known epitopes in VP13/14, VP22, or ICP0 (Table 9). However, known epitopes collectively accounted for only a small minority of the CTL clones.

TABLE 9

Fine specificity of HSV-2-specific CD8 CTL clones made from directly sorted CLA$^{high}$ PBMC.

| Subject ID. HLA | Clones tested | Number (%) of clones | Restricting allele* | HSV-2 ORF† | HSV-2 protein† | Amino acid† | HSV reactivity‡ |
|---|---|---|---|---|---|---|---|
| 1 | 34 | 18 (53) | A*0201 | UL47 | VP13/14 | 551-559 | TS |
| A*02,*23 B*58,*13 | | 7 (20) | B*5801 | UL54 | ICP27 | Unknown | TS |
| | | 5 (15) | A*0201 | UL47 | VP13/14 | 289-298 | TS |
| | | 2 (6) | A*0201 | UL54 | ICP27 | Unknown | TS |
| | | 2 (6) | | | Unknown | | |
| 2 | 11 | 6 (55) | B*1402 | UL25 | UL25 | 405-413 | TS |
| A*01,*32 B*14,*27 | | 3 (27) | B*1402 | UL7 | UL7 | 174-186 | TS |
| | | 1 (9) | B*27052 | US6 | gD2 | 365-373 | TS |
| | | 1 (9) | DR*01∥ | | Unknown | | |
| 3 | 14 | 9 (64) | B*1402 | UL25 | UL25 | 405-413 | TS |
| A 2, 3 B 14 | | 5 (36) | B*1402 | UL7 | UL7 | 174-186 | TS |
| 4 | 4 | 4 (100) | A*0201 | UL47 | VP 13/14 | 551-559 | TS |
| A*02,*24 B*44 | | | | | | | |

TABLE 9-continued

Fine specificity of HSV-2-specific CD8 CTL clones made from directly sorted CLA$^{high}$ PBMC.

| Subject ID. HLA | Clones tested | Number (%) of clones | Restricting allele* | HSV-2 ORF† | HSV-2 protein† | Amino acid† | HSV reactivity‡ |
|---|---|---|---|---|---|---|---|
| 5 | 6 | 4 (67) | B*0702 | UL49 | VP22 | 49-57 | TS |
| A*02,*03 B*07,*44 | | 2 (34) | B*0702 | UL26 | UL26§ | 475-483 | TS |
| 6 | 5 | 2 (40) | B*0702 | RL2 | ICP0 | 743-751 | TS |
| A1, 26 B7, 8 | | 2 (40) | A*0101 | UL46 | VP11/12 | 354-362 | TC |
| | | 1 (20) | B*0702 | UL49 | VP22 | 49-57 | TS |
| 7 | 7 | 7 (100) | B*37 | | Unknown¶ | | TS/TC¶ |
| A*02,*24 B*07,*37 | | | | | | | |
| 8 | 5 | 2 (40) | B*5701 | US8 | gE2 | 518-526 | TS |
| A1, 2 B8, 57 | | 2 (40) | A*0201 | UL47 | VP13/14 | 551-559 | TS |
| | | 1 (20) | A*0201 | UL47 | VP13/14 | 289-298 | TS |

*Data from cDNA positive in Cos-7 co-transfection assay except for partially matched APC (subject 7) or mAb inhibition (subject 2, HLA DR-restricted clone).
†From Dolan et al., 1998, J. Virol. 72: 2010-2021.
‡TS (type-specific) clones lyse only HSV-2 infected cells. TC (type-common) clones lyse both HSV-1 and HSV-2 infected cells.
§Nomenclature for proteins encoded by overlapping UL26/UL26.5 genes is complex.
¶Cell culture failure prevented work-up. One clone HSV type-common, six HSV-2 type-specific.
∥A single DR*01-restricted, CD4$^+$ CD8$^{smear+}$ TCRαβ$^+$ CD3$^+$ CTL clone was detected.

Epitope discovery for the remaining clones began with determination of their HLA restricting alleles. Clear evidence of HLA class I restriction was obtained, with a few exceptions (below). Only one or two restricting HLA class I alleles were detected per subject (Table 9), an early indicator that the dominant responses might be oligospecific. The HLA cDNAs for each restricting HLA alleles were made, and their cell-surface expression, as well as clonal T-cell restriction, were confirmed in a transfection/infection system. Expression cloning was then performed with a library of genomic HSV-2 DNA. This uses co-transfection of primate cells with the relevant HLA class I heavy chain cDNA and library DNA, and detection of T-cell activation by IFN-γ secretion. As HSV-2 DNA fragments encoding novel antigens were uncovered (Table 10), remaining HLA-appropriate clones were assayed for reactivity with the new, reactive HSV-2 DNA fragments. As peptide epitopes became available (below), clones with suitable HLA restriction were re-tested with synthetic peptides to definitively assign fine specificity.

definition of HSv-2 UL7, UL25, UL46, and US8 as T-cell antigens. For two clones, the initial positive genomic fragment contained portions of more than one known HSV-2 ORF. In the first example, CD8 clone 8.2H1 (Table 10) reacted with an 1.35 kB genomic fragment containing part of genes US8, all of US9 and its promoter, and parts of US8.5 and US10 out of frame or back-wards. US8, US8.5, and US9 were tested in isolation by co-transfection of single ORFs with HLA B*5701 cDNA. Only US8, which encodes membrane glycoprotein E, was active. In the second example, CD8 clone 5.1E4 (Table 10) reacted with 316 base-pair fragment in-frame both the UL26 and internally overlapping UL26.5 ORFs.

Figure 13:
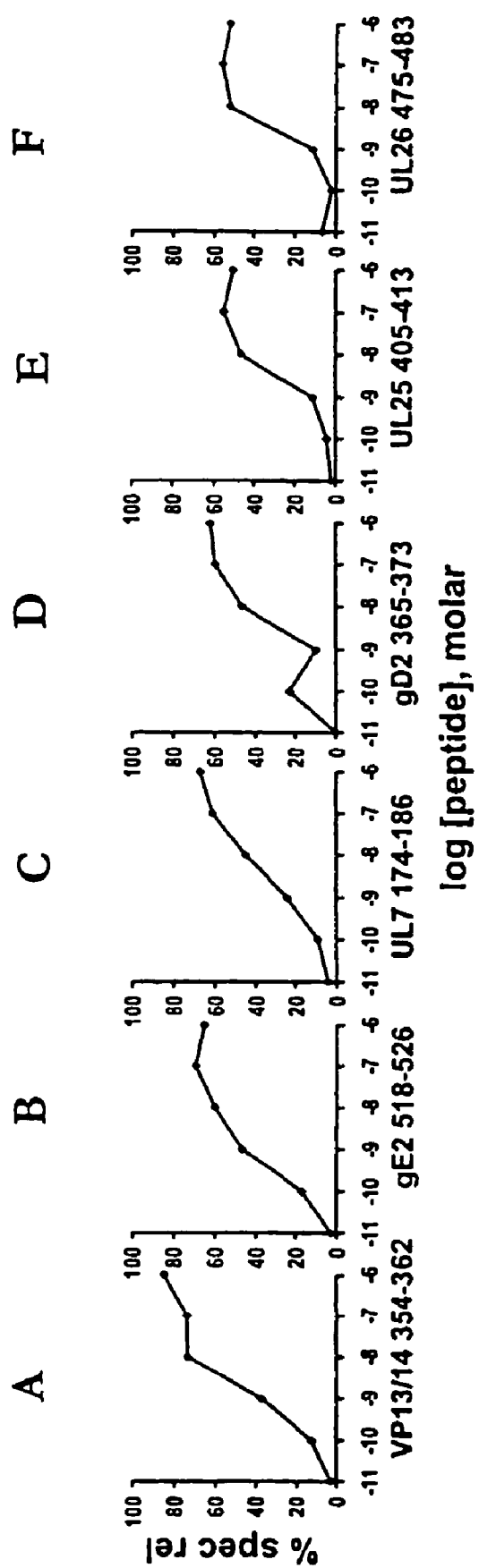
FIGS. 13A-13F. Cytotoxicity of HLA class I-restricted CD8 clones towards autologous EBV-LCL targets pulsed with the indicated concentrations of HSV-2 peptides. Predicted HSV-2 proteins and amino acid residue numbers are indicated. Results are percent specific release at effector to target ratios of 20.

The newly discovered antigens (Table 9) were each confirmed with synthetic peptides (FIG. 13). For CD8 clone 3.F8 (Table 10), truncation analysis at the genomic viral DNA level, followed by detection of T-cell activation in the Cos-7 co-transfection assay, reduced the antigenic region to amino acids 150-192. This was followed by evaluation of overlap-

TABLE 10

HSV-2 DNA fragments stimulating IFN-γ secretion by CD8 CTL clones with novel specificities derived by CLA-based sorting of PBMC.

| Subject | CD8 clone | Co-transfected HLA cDNA | HSV-2 genomic DNA fragment | HSV-2 gene(s)* | HSV-2 protein fragment(s): amino acids |
|---|---|---|---|---|---|
| 3 | F8 | B*1402 | 17,406-17,824 | UL7 | UL7: 50-192 |
| 2 | 1F3 | B*1402 | 49,999-50,287 | UL25 | UL25: 322-417 |
| 5 | 1E4 | B*0702 | 52,594-52,910 | UL26/UL26.5 | UL26: 404-627 |
| 6 | E2 | A*0101 | 99,085-100,838 | UL46 | VP11/12: 254-722 |
| 2 | 2B9 | B*27052 | 142,038-142,393 | US6 | gD2: 342-393 |
| 8 | 2H1 | B*5701 | 145,347-146,693 | US8, US9† | gE2: 503-545, US9: 1-89 |

*HSV-2 genes predicted to be forward and in-frame with vector translational start, or to follow their endogenous promoter.
†A portion of US8.5 is forward but out of frame. A portion of US10 is present, but backwards.

Six new epitopes were discovered in the course of studying 36 clones from five subjects. In four cases, the initial positive HSV-2 genomic DNA library fragments contained portions of a single known HSV-2 ORF (Table 10). This allowed ping 13-mer peptides in CTL assays to find the epitope (amino acids 174-186, FIG. 13). For the other five clones (Table 10), sequencing data, HSV type-specific vs. type-common reactivity, and HLA peptide-binding motifs allowed more targeted syntheses of candidate nonamer peptide epitopes, which were successful in each case. Each blood-derived CD8 CTL clone recognized synthetic peptides at low concentrations, with 50% maximal responses detected near 1 nanomolar (FIG. 13).

Two of the newly described antigens were HSV-2 virion tegument proteins. Previously, strong recognition of tegument proteins was detected among CD8 CTL recovered from skin biopsies of healing HSV-2 genital lesions. Clone 6.E2 (Table 10) recognized VP11/12, the product of gene UL46. Clone 3.F8 (Table 10), and similar clones, recognized the predicted translation product of gene UL7. This protein is in the tegument, but is otherwise little-studied. Neither UL25 nor UL7 have previously been described as CD8 antigens. Two of the new HSV-2 CD8 antigens were capsid or capsid-associated proteins. The protein VP26, encoded by UL25, was recognized by CD8 CTL from two subjects. A protein in the capsid scaffold, encoded by UL26 or UL26.5, was also recognized by CD8 CTL. The scaffold is a precursor framework for virion capsid assembly that is degraded prior to formation of mature virions, although scaffold proteins persist in immature B capsids. This is the first description of CD8 T-cell reactivity with either a capsid or scaffold protein of HSV. The final two new CD8 epitopes were in HSV-2 envelope glycoproteins. Clone 2.2B9 (Table 10) reacted with an epitope in the C-terminal cytoplasmic domain of glycoprotein D. Clone 8.2H1 (Table 10) recognized a peptide in the C-terminal cytoplasmic domain of glycoprotein E. While CD8 responses to gD2 have been detected, this is the initial description of CD8 responses to gE of HSV. Peptide sequences can be derived from the predicted amino acid sequences of the relevant HSV-2 proteins as published in Genbank NC_001798.

Patterns of antigen and epitope immunodominance. Within individual subjects, clones reactive with one or two proteins tended to predominate (Table 9). Responses were detected to a maximum of three antigens per person. Several patterns were present. For subject 4, each clone reacted with single epitope in VP13/14; this expansion was earlier detected in this subject with direct tetramer staining of PBMC. For subject 1, all 34 clones reacted with either VP13/14 or a single immediate early protein, ICP27 (see below). The other two subjects (numbers 2 and 3) from whom large numbers of clones were obtained were both HLA B14 positive. Each predominantly recognized both tegument protein UL7 and capsid protein UL25 in the context of HLA B*1402. HLA B*1402-restricted responses seemed to dominate over responses restricted by any of the other available HLA class I alleles; in subject 3, a single, B*2705-restricted clone recognizing gD2 was detected as a minor response. Two-thirds of the clones from subject 5 recognized VP22 49-57; this expansion was also detectable with tetramer staining of PBMC (0.6% of CD8$^{hi}$ cells). The total number of clones available from some subjects was low, precluding definitive conclusions about immunodominance, but it was again noted for subject 7 that all seven HSV-2-specific clones were HLA B*37-restricted, consistent with a relative oligoclonality among the numerically predominant responses.

Immunodominance can also be studied within populations. Some trends were observed from the data described herein. HLA A*0201 is the commonest HLA class I allele in most ethnic groups. Among six HLA A2-positive persons, reactivity was detected with VP13/14 in three. Clones reactive with amino acids 551-559 were recovered from three persons, while clones reactive with 289-298 were recovered from two. No subject yielded clones reacted with gB2 443-451; responses to this peptide, if present, are predicted to be numerically subdominant in most persons. Among three HLA B7-positive subjects, two had blood-derived clones reactive with VP22 49-57 and one had an ICP0 743-751-reactive clone. Of note, some subjects with the appropriate HLA alleles had no detectable responses to peptides restricted by these alleles. For example, neither subjects 3 and 7, both HLA A2-positive, had A2-restricted responses among 23 independent clones studied, and subject 9906 had no HLA B7-restricted clones detected. Among other subjects, HLA A2 or HLA B7 completely dominated the response.

The relative immunogenicity of different structural and kinetic classes of HSV-2 proteins can also be compared within the population. Overall, amongst 86 independent HSV-2-specific CD8 CTL clones derived by sorting CLA-expressing cells from the peripheral blood of seven subjects, 45 (52.3%) recognized tegument, 15 (17%) recognized capsid, 3 (3%) recognized envelope glycoprotein, and 2 (2%) recognized scaffold proteins (Table 10). An additional 11 (13%) recognized non-structural immediate early proteins, either ICP0 or ICP27 (below). The specificity of 10 clones (12%) were not determined. All seven subjects who had analyses of fine specificity yielded tegument-specific clones. Two subjects each had scaffold, envelope glycoprotein, or immediate-early protein-specific clones, and one subject had capsid-specific responses. These data indicate that memory CD8 responses to HSV-2 tegument proteins are efficiently maintained in chronically infected, immunocompetent persons.

Immunodominance studies with bulk CTL cultures. It is possible that lower-abundance CD8 CTL responses are not detected in the clonal frequency analyses presented above. Therefore, in selected subjects, the specificity of CLA+ HSV-2-specific CTL was investigated using alternate assay formats. As noted above (FIG. 11), HSV-specific cytotoxicity was preferentially present in cultures derived from CD8' CD28' PBMC that also expressed CLA. One to two thousand sorted PBMC were expanded to a few million cells over two weeks using PHA and IL-2; one additional cycle of expansion of a portion of these cells with anti-CD3 yielded several hundred million cells in an additional 10-14 days. These bulk lymphocyte cultures were tested with target cells expressing, or failing to express, defined HSV-2 genes.

Figure 14:
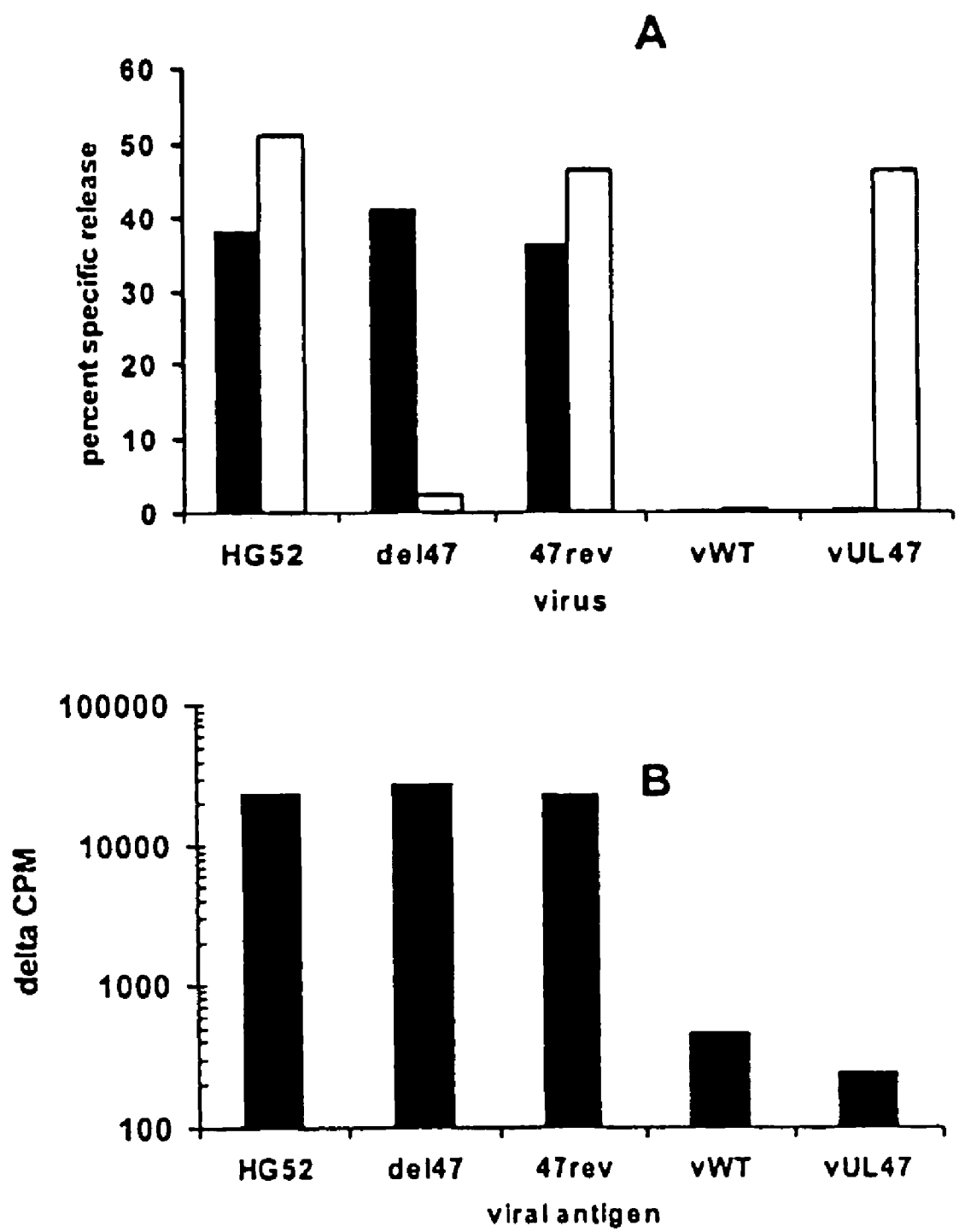
FIGS. 14A-14B. Antigen expression by recombinant viruses.

To isolate responses to VP13/14, new reagents were created and first validated. Wild-type HSV-2, an HSV-2 mutant deleted for VP13/14 (del47), and a revertant virus with wild-type UL47 re-inserted (47rev) were compared. VP13/14-specific clones failed to lyse del47, but did recognize lysed 47rev (FIG. 14). The disruption strategy for UL47 risked disturbing expression of the proteins VP11/12 and VP16, which are encoded by the respective adjacent genes UL46 and UL48. Both of these proteins are known T-cell antigens. VP11/12 and VP16-specific T-cell clones recognized the deletion and rescue viruses, confirming that disruption in del47 was isolated to UL47. In addition, southern blots of restriction endonuclease-digested cytoplasmic DNA preparations from cells infected with HG52, 47del, and rev47 gave the expected patterns with probes from the UL46 and UL47 ORFs and eGFP. A recombinant vaccinia expressing VP13/14 (gene UL47) was also created and checked for protein expression with a T-cell clone specific for VP13/14 551-559. Specific lysis was of autologous target cells was observed (FIG. 14), consistent with VP13/14 expression.

PBMC-derived bulk effectors from subjects 1 and 4, both of whom yielded multiple CD8 CTL clones specific for VP13/14, were studied with these new reagents. For both subjects, deletion of UL47 (VP13/14) was associated with significantly decreased lysis of HSV-2-infected cells (FIG.

11). Restoration of UL47 lead to a return of lysis to levels similar to that seen with parental, wild-type virus. Consistent with these findings, bulk, non-cloned effectors selected on the basis of homing receptor expression showed considerable lysis of target cells infected with vaccinia-VP13/14. Autologous cells pulsed with a single peptide, VP13/14 551-559, were highly recognized by bulk polyclonal CTL from subject 4, in agreement with the clonal analysis from this subject showing that each available clone recognized this peptide (Table 9). Subject 1 also showed significant lysis of cells infected with vaccinia-ICP27, again consistent with their clonal analysis.

Type specificity of HSV-reactive CD8 CTL. Each HSV-2-reactive CD8 CTL clone was analyzed for recognition of HSV-1. Several of the subjects were seropositive for both HSV-1 and HSV-2 (Table 7). Among the six new CD8 T-cell epitopes (Table 10), only one, HSV-2 UL46 354-362, has the identical sequence in the analogous HSV-1 protein. The two clones from subject 6 recognizing this epitope killed both HSV-1 and HSV-2 infected cells. This subject was seropositive for both HSV-1 and HSV-2 (Table 7). Every clone tested among those recognizing the other five novel epitopes (Table 10), the previously described epitopes, and the ICP27-specific clones from subject 1 were all HSV-2 type-specific. Among the seven HLA B*37-restricted HSV-2-specific CD8 CTL clones from subject 7, one had type-common cytotoxicity towards HSV-1. Amongst the nine precisely known HSV-2 CD8 epitopes and 86 HSV-2-reactive CD8 CTL clones studied in this example, only one epitope and three clones are type-common for both HSV-1 and HSV-2.

Figure 15:
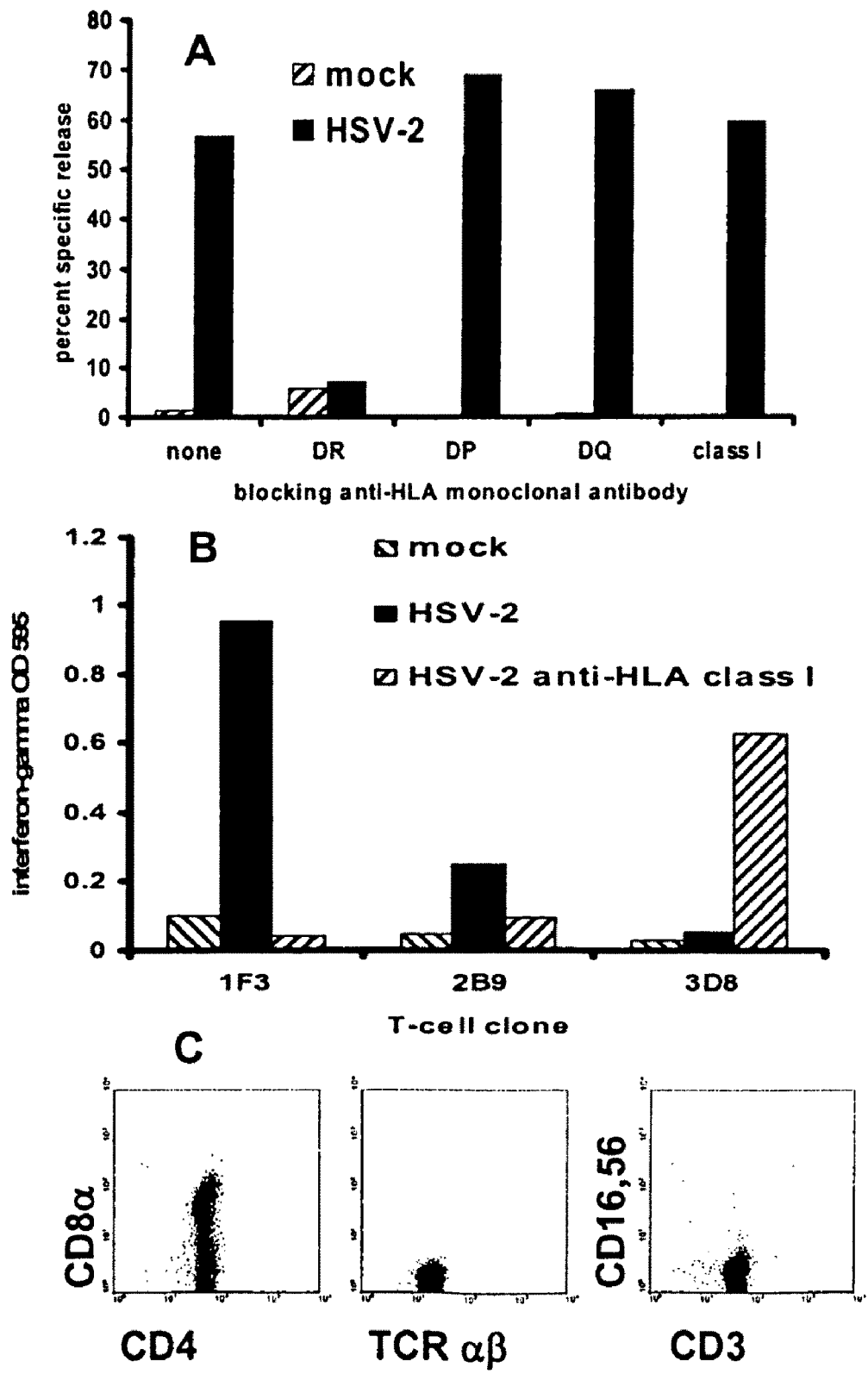
FIGS. 15A-15C. Properties of atypical clone 2.3D8 selected by CD8α, CD28, and CLA expression.

HLA DR-restriction by HSV-2-specific CD4$^+$ CD8$^+$ CTL. A single clone was detected from subject 2 (Table 9) that displayed lysis of allogeneic EBV-LCL that were mismatched at HLA A and B alleles. Lysis by this atypical clone, which recognized both HSV-1 and HSV-2, was strongly inhibited by anti-HLA DR mAb but not anti-class I mAb (FIG. 15A-15C). The subject is homozygous for DRB1*01, and allogeneic cells mismatched at HLA class I but matched at DR were lysed after HSV-2 infection. In contrast to typical CD8 clones, secretion of IFN-γ in response to autologous infected EBV-LCL was weak, but was strongly enhanced, rather than inhibited, by anti-HLA class I. This clone displayed heterogeneous CD8α expression, but was uniformly CD4$^+$, CD3$^+$, and TCRαβ$^+$ and negative for CD16 and CD56 analyzed together (FIG. 15) or separately.

Discussion

Newer technologies have revealed expansions of CD8 T-cells reactive with defined viral epitopes in individuals with chronic viral infections. However, it has been challenging to measure the relative contributions of peptide-specific T-cells in the context of the global anti-viral response. In the case of HSV-2, detailed knowledge of hierarchies of immunodominance is also of practical interest with regards to vaccine design. In this example, a novel one-step purification method was used, based on the expression of the skin homing receptor, CLA, to enrich HSV-2-specific CD8 T-cells from the peripheral blood of humans. HSV-2 is a member of the subfamily Alphaherpesvirinae, a group of pathogens with tropism for the skin. Employing this strategy, a striking concentration of the virus-specific CD8 CTL response to just a few dominant antigens and epitopes per subject was discovered.

The HSV-2-specific CD8 CTL, recognized antigens were recovered in diverse viral structural and kinetic classes. Clonal responses to tegument proteins VP13/14 and VP22 and immediate early protein ICP0, previously described for CD8 clones recovered from HSV-2-infected tissue, were confirmed in blood. Reactivity to two additional tegument proteins was found: the UL7 gene product and VP11/12. Clonal recognition of the immediate early protein ICP27 confirms work with CTL bulk effectors. In addition, responses to structural envelope, capsid, and scaffold proteins were observed. CD8 recognition of the envelope glycoprotein gD2 has previously been described, but this is the first description of CD8 responses to envelope glycoprotein gE2, a component of the HSV-encoded Fc receptor involved in immune evasion. This is also the initial description of CD8 T-cell reactivity with HSV capsid or scaffold proteins. The UL25 gene product, VP26, is a structural capsid protein present at low levels (about 40 copies) in mature virions. The protein products of the UL26 and co-linear UL26.5 genes are a complex family of polypeptides. They form a part of the capsid scaffold, and are thought to be excluded from mature virions. Taken together, these findings indicate that analyses of HSV CD8 T-cell antigens should include the entire viral proteome.

By producing panels of independently-derived HSV-2-specific CD8 CTL clones from several subjects, and determining their fine specificity, it was possible to determine the frequency distribution of the numerically predominant CTL precursors recognizing specific viral epitopes. In most subjects, only a few HSV peptides accounted for the majority of the circulating CTL precursors. This finding suggests that, in the chronic phase of infection, the numerically immunodominant memory CTL response to this genomically complex organism is quite focused on a small number of antigens and epitopes. For one subject, 10063, the immunodominant response was spread over four epitopes, but these occurred within two proteins (tegument VP13/14 and immediate early ICP27). Strikingly, two persons with the B*1402 allele, subjects 2 and 3, both displayed immunodominant B*1402-restricted responses to the same two epitopes in the protein products of the UL25 and UL7 genes. In this regard, HSV-2 may be similar to HIV-1, in which specific epitopes tend to be immunodominant in HLA B*1402-positive persons.

Circulating CD8 T-cells specific for HSV-2 epitopes in the viral tegument proteins VP13/14 and VP22, and an epitope in the viral immediate early protein ICP0, were earlier shown to preferentially express CLA. In contrast, CD8 T-cells specific for CMV or EBV, which do not infect skin, did not express CLA. This finding is now extended to HSV-2-specific CD8 T-cells of diverse fine specificity. Aggregate peptide, HLA restriction, and vaccinia data gable 9) indicate that at least ten additional HLA class I-restricted HSV-2 CD8 epitopes are recognized by circulating CLA$^+$ cells. CLA expression also co-segregated with HSV-2-specific cytotoxicity in assays with bulk effector cells (FIG. 11). While low levels of HSV-2-specific CTL may be still be present among CD8 cells that are not CLA$^+$, the data concerning antigenic specificity are believed to apply to the principle population of circulating HSV-2-specific CD8 T-cells.

CD28 expression was also used as a criteria for cell sorting. The expression of CD28 by virus-specific CD8 T-cells appears to vary between viruses and between epitopes and individuals. The successful recovery of HSV-2-specific CTL from almost every HSV-2-infected person studied is consistent with CD28 expression by circulating virus-reactive CD8 cells recognizing a variety of epitopes. Further research is required to determine if, within the CLA$^+$ compartment, significant levels of CTL are present in within CD28$^-$ cells.

The factors influencing immunodominance in the human CD8 response to HSV-2 are largely unknown. In C57BL/6 mice, cells reactive with a single HSV epitope in glycoprotein B are numerically dominant, despite the presence of many peptides with appropriate MHC binding motifs, during primary and secondary responses. Immunization with this epitope protects against viral challenge. Endogenous synthesis of gB, rather than cross-presentation, is required for memory CD8 T-cell recognition. The HSV protein ICP47 is a powerful inhibitor of TAP in humans, but not mice. It has been hypothesized the CD8 response in humans is weighted towards recognition of proteins that are delivered into the cytoplasm upon virion entry, or are synthesized within infected cells very quickly after viral infection. In this scenario, T-cells recognize antigens that are processed and presented prior to TAP inhibition. Data with mutant viruses with incomplete replication cycles, metabolic inhibitors, and previously described CTL clones are consistent with this hypothesis. The expanding spectrum of HSV CD8 antigens reported herein need to be evaluated for recognition of pre-formed versus endogenously synthesized protein. As treatment of APC with IFN-γ can overrule the immune evasion effects of ICP47 and vhs, and high levels of IFN-γ are present in HSV lesions, the concept that these genes modulate the CD8 repertoire to HSV in humans may need to be re-evaluated.

This example demonstrates that, in humans, while HLA genotype has an influence, it is not the most important factor in determining immunodominance. For example, within the group of HLA A*02-bearing persons, A*0201-restricted clones were commonly detected in some subjects, such as 1 and 4, but were not detected in subjects 3 or 3. Similarly, B*0702 was internally dominant in subject 5, but no B*07-restricted clones were detected in the panel of CTL from subject 7.

Using IFN-γ ELISPOT, responses were detected to known A*0201- or B*0702-restricted epitopes in VP13/14 and VP22 in subjects who did not have clones with these specificities recovered by CLA enrichment. The algorithm starts with cytotoxicity as the index criteria for selection, which differs from ELISPOT. Of note, every clone initially detected by CTL, activity was a brisk secretor of IFN-γ, a readout used during the expression cloning process.

In animal models, several factors other than MHC haplotype can influence immunodominance. These include the frequency of naïve precursors, and competition for antigen processing or presentation between antigens, MHC alleles, or T-cells. Prior antigenic experience can also profoundly effect immunodominance. It has also been observed in human EBV infection that HLA haplotypes at the non-restricting allele can influence the makeup of the CD8 response. EBV-specific responses that are typically immunodominant in persons with specific HLA alleles are modified if these clonal responders are also fortuitously cross-reactive with self HLA-restricted autodeterminants. Clonal cross-reactivity does occur between self HLA plus HSV-2 peptide, and allogeneic HLA molecules plus presumed housekeeping peptides. The examples and data mentioned above support the hypothesis that self antigenic structures may also modify the CD8 response to HSV-2.

An atypical, $CD4^+CD8^{variable}$ T-cell clone that was HSV-2-specific and restricted by HLA DR was detected in this study. This clone may represent an in vivo cell population, rather titan a consequence of non-physiologic in vitro T-cell expansion conditions, because the initial cell sorting criteria included high CD8α selection. This is unlikely to have enriched for routine $CD4^+$ $CD8α^-$ cells. Future sorting experiments will address the prevalence of this cell type in the population.

Comparison of these findings with HSV-2 to other studies of human pathogens is challenging. The algorithm of enrichment based on homing receptor expression, cloning, and exhaustive epitope determination has not previously been applied. While large expansions can be found with tetramers, the denominator, representing the entire virus-reactive population, is usually measured with an alternative method. Overlapping peptides covering the entire predicted protein sequence of viruses have been used to as an alternative method to interrogate circulating lymphocytes. Walker et al. used overlapping peptides and a set of known HLA-restricted peptides encoded by HCV, and IFN-γ ELISPOT, to study CD8 responses in HCV infection. The overall correlation between HLA type and the detection of specific HLA-restricted responses was low. Similar to these findings, responses to single HCV epitopes were found to comprise 40-80% of the overall, integrated response against the peptide set covering the entire virus (Lauer et al., 2002, J. Virol. 76:6104-13). Different technologies were used, and the overall magnitude of the response to HCV is low. CD8 responses to peptides covering the entire HIV-1 genome were also studied with IFN-γ ELISPOT. A median of 14 epitopes were recognized per subject, but data on within-subject immunodominance were not provided. A similar analysis using IFN-γ intracellular cytokine cytometry and HIV-1 peptide pools showed that responses to individual proteins could be internally immunodominant in some subjects, but data were not provided to address dominance at the peptide level.

In this example, responses were analyzed to the level of viral peptide specificity. Microheterogeneity can be found in the predicted CDR3-encoded regions of TCR α and β V region cDNAs. Shifts in dominant TCR clonotypes have been documented within peptide-specific responses during the evolution of the CD8 response to EBV. Other analyses have found that dominance at the level of TCR sequences is relatively stable over time. Panels of independent human HSV-2-specific CD8 clones were derived from skin lesions after preliminary in vitro expansion that recognized the same viral peptide. Limited heterogeneity in TCV β cDNA sequences was observed, with no changes for some reactivities over intervals up to seven years.

The identification of immunodominant HSV-2 CD8 CTL antigens has practical applications. HSV-2 can cause serious infections of neonates and of immunocompromised hosts, may double the risk of HIV-1 acquisition, and causes painful skin lesions. A vaccine eliciting antibody and CD4 responses had only partial protective efficacy that was limited to HSV-1 and HSV-2 dually-seronegative women. Replication-competent or discontinuously replicating HSV-2 mutants, better suited for CD8 responses, have reached clinical trials for HSV prevention or immunotherapy and are also used for cancer therapy. Overall, the data disclosed herein indicate that, in the context of chronic viral infection, responses specific for a limited number of epitopes and antigens become immunodominant, and the specificity of the numerically immunodominant clones cannot be predicted from HLA typing. While vaccines elicit responses in a different context from wild-type infection, similar hierarchies and patterns of immunodominance may occur. Vaccines designed to elicit CD8 responses should therefore contain several epitopes for each population-prevalent HLA allele, ideally picked from analyses of immunodominant epitopes.

The clonal analysis found that CD8 CTL to HSV-2 in the circulating $CLA^+$ compartment are largely type-specific for HSV-2. Earlier studies had estimated cross-reactivity to be about 50%. Prior HSV-1 infection reduces the severity of initial HSV-2 infections. The relative contributions of T-cells and antibodies to this effect are not known. The current findings will also allow a more systematic approach to define if the immunodominant CD8 T-cell response to HSV-2 differs between HSV-2 infected versus HSV-1/HSV-2 co-infected persons.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims. Throughout this application various publications are referenced. The disclosures of these publications in their entireties are hereby incorporated by reference into this application in order to describe more fully the state of the art to which this invention pertains.

What is claimed is:

1. A pharmaceutical composition comprising a herpes simplex virus (HSV) polypeptide, wherein the polypeptide comprises amino acids 405-413 and up to 30% of the full length of UL25 (SEQ ID NO: 8).

2. The pharmaceutical composition of claim 1, wherein the polypeptide is a fusion protein comprising the HSV polypeptide fused to an unrelated immunogenic protein.

3. The pharmaceutical composition of claim 2, wherein the fusion protein is soluble.

4. The pharmaceutical composition of claim 1 further comprising an adjuvant.

5. The pharmaceutical composition of claim 1, wherein the polypeptide comprises up to 10% of the full length of the HSV polypeptide.

6. A pharmaceutical composition comprising a herpes simplex virus (HSV) polypeptide or a polynucleotide encoding said polypeptide, wherein the polypeptide consists of amino acids 405-413 or 322-417 of UL25.

7. A pharmaceutical composition comprising a polynucleotide that encodes a HSV polypeptide comprising amino acids 405-413 and up to 30% of the full length of UL25 (SEQ ID NO: 8).

8. The pharmaceutical composition of claim 7, further comprising an adjuvant.

9. The pharmaceutical composition of claim 7, wherein the polypeptide is a fusion protein comprising the HSV polypeptide fused to an unrelated immunogenic protein.

10. The pharmaceutical composition of claim 7, wherein the polynucleotide comprises a recombinant virus genetically modified to express the HSV polypeptide.

11. The pharmaceutical composition of claim 10, wherein the recombinant virus is a vaccinia virus, canary pox virus or adenovirus.

12. The pharmaceutical composition of claim 10, further comprising an adjuvant.

13. A method of inducing an immune response to an HSV infection in a subject comprising administering the composition of claim 1 to the subject.

14. A method of inducing an immune response to an HSV infection in a subject comprising administering the composition of claim 7 to the subject.

15. A method of treating an HSV infection in a subject comprising administering the composition of claim 1 to the subject.

16. A method of treating an HSV infection in a subject comprising administering the composition of claim 7 to the subject.

17. The pharmaceutical composition of claim 6, wherein the polynucleotide comprises a recombinant virus genetically modified to express amino acids 405-413 or 322-417 of UL25 (SEQ ID NO: 8).

18. The pharmaceutical composition of claim 1, wherein the polypeptide comprises up to 20% of the full length of the HSV polypeptide.

19. The pharmaceutical composition of claim 7, wherein the polypeptide comprises up to 20% of the full length of the HSV polypeptide.

* * * * *

```
                           SEQUENCE LISTING

<160> NUMBER OF SEQ ID NOS: 17

<210> SEQ ID NO 1
   <211> LENGTH: 9
   <212> TYPE: PRT
   <213> ORGANISM: Herpes Simplex Virus 2

<400> SEQUENCE: 1

Asp Arg Leu Asp Asn Arg Leu Gln Leu
   1               5

<210> SEQ ID NO 2
   <211> LENGTH: 9
   <212> TYPE: PRT
   <213> ORGANISM: Herpes Simplex Virus 2

<400> SEQUENCE: 2

Gly Pro His Glu Thr Ile Thr Ala Leu
   1               5

<210> SEQ ID NO 3
   <211> LENGTH: 13
   <212> TYPE: PRT
   <213> ORGANISM: Herpes Simplex Virus 2

<400> SEQUENCE: 3

His Ala Ser Pro Phe Glu Arg Val Arg Cys Leu Leu Leu
   1               5                   10

<210> SEQ ID NO 4
   <211> LENGTH: 9
   <212> TYPE: PRT
   <213> ORGANISM: Herpes Simplex Virus 2

<400> SEQUENCE: 4

Ala Ser Asp Ser Leu Asn Asn Glu Tyr
   1               5

<210> SEQ ID NO 5
   <211> LENGTH: 9
   <212> TYPE: PRT
   <213> ORGANISM: Herpes Simplex 2

<400> SEQUENCE: 5

Arg Arg Ala Gln Met Ala Pro Lys Arg
   1               5

<210> SEQ ID NO 6
   <211> LENGTH: 9
   <212> TYPE: PRT
   <213> ORGANISM: Herpes Simplex 2
```

```
<400> SEQUENCE: 6

Lys Ser Arg Arg Pro Leu Thr Thr Phe
 1               5

<210> SEQ ID NO 7
<211> LENGTH: 296
<212> TYPE: PRT
<213> ORGANISM: Herpes Simplex Virus 2

<400> SEQUENCE: 7

Met Ala Asp Pro Thr Pro Ala Asp Glu Gly Thr Ala Ala Ile Leu
 1               5                  10                  15

Lys Gln Ala Ile Ala Gly Asp Arg Ser Leu Val Glu Val Ala Glu Gly
                 20                  25                  30

Ile Ser Asn Gln Ala Leu Leu Arg Met Ala Cys Glu Val Arg Gln Val
                 35                  40                  45

Ser Asp Arg Gln Pro Arg Phe Thr Ala Thr Ser Val Leu Arg Val Asp
     50                  55                  60

Val Thr Pro Arg Gly Arg Leu Arg Phe Val Leu Asp Gly Ser Ser Asp
 65                  70                  75                  80

Asp Ala Tyr Val Ala Ser Glu Asp Tyr Phe Lys Arg Cys Gly Asp Gln
                 85                  90                  95

Pro Thr Tyr Arg Gly Phe Ala Val Val Leu Thr Ala Asn Glu Asp
                100                 105                 110

His Val His Ser Leu Ala Val Pro Pro Leu Val Leu His Arg Leu
            115                 120                 125

Ser Leu Phe Arg Pro Thr Asp Leu Arg Asp Phe Glu Leu Val Cys Leu
    130                 135                 140

Leu Met Tyr Leu Glu Asn Cys Pro Arg Ser His Ala Thr Pro Ser Leu
145                 150                 155                 160

Phe Val Lys Val Ser Ala Trp Leu Gly Val Val Ala Arg His Ala Ser
                165                 170                 175

Pro Phe Glu Arg Val Arg Cys Leu Leu Leu Arg Ser Cys His Trp Ile
            180                 185                 190

Leu Asn Thr Leu Met Cys Met Ala Gly Val Lys Pro Phe Asp Asp Glu
        195                 200                 205

Leu Val Leu Pro His Trp Tyr Met Ala His Tyr Leu Leu Ala Asn Asn
    210                 215                 220

Pro Pro Pro Val Leu Ser Ala Leu Phe Cys Ala Thr Pro Gln Ser Ser
225                 230                 235                 240

Ala Leu Gln Leu Pro Gly Pro Val Pro Arg Thr Asp Cys Val Ala Tyr
                245                 250                 255

Asn Pro Ala Gly Val Met Gly Ser Cys Trp Asn Ser Lys Asp Leu Arg
            260                 265                 270

Ser Ala Leu Val Tyr Trp Trp Leu Ser Gly Ser Pro Lys Arg Arg Thr
        275                 280                 285

Ser Ser Leu Phe Tyr Arg Phe Cys
    290                 295

<210> SEQ ID NO 8
<211> LENGTH: 585
<212> TYPE: PRT
<213> ORGANISM: Herpes Simplex Virus 2
```

<400> SEQUENCE: 8

```
Met Asp Pro Tyr Tyr Pro Phe Asp Ala Leu Asp Val Trp Glu His Arg
 1               5                  10                  15

Arg Phe Ile Val Ala Asp Ser Arg Ser Phe Ile Thr Pro Glu Phe Pro
            20                  25                  30

Arg Asp Phe Trp Met Leu Pro Val Phe Asn Ile Pro Arg Glu Thr Ala
        35                  40                  45

Ala Glu Arg Ala Ala Val Leu Gln Ala Gln Arg Thr Ala Ala Ala Ala
    50                  55                  60

Ala Leu Glu Asn Ala Ala Leu Gln Ala Ala Glu Leu Pro Val Asp Ile
65                  70                  75                  80

Glu Arg Arg Ile Arg Pro Ile Glu Gln Gln Val His His Ile Ala Asp
                85                  90                  95

Ala Leu Glu Ala Leu Glu Thr Ala Ala Ala Ala Glu Glu Ala Asp
            100                 105                 110

Ala Ala Arg Asp Ala Glu Ala Arg Gly Glu Gly Ala Ala Asp Gly Ala
        115                 120                 125

Ala Pro Ser Pro Thr Ala Gly Pro Ala Ala Glu Met Glu Val Gln
130                 135                 140

Ile Val Arg Asn Asp Pro Pro Leu Arg Tyr Asp Thr Asn Leu Pro Val
145                 150                 155                 160

Asp Leu Leu His Met Val Tyr Ala Gly Arg Gly Ala Ala Gly Ser Ser
                165                 170                 175

Gly Val Val Phe Gly Thr Trp Tyr Arg Thr Ile Gln Glu Arg Thr Ile
            180                 185                 190

Ala Asp Phe Pro Leu Thr Thr Arg Ser Ala Asp Phe Arg Asp Gly Arg
        195                 200                 205

Met Ser Lys Thr Phe Met Thr Ala Leu Val Leu Ser Leu Gln Ser Cys
    210                 215                 220

Gly Arg Leu Tyr Val Gly Gln Arg His Tyr Ser Ala Phe Glu Cys Ala
225                 230                 235                 240

Val Leu Cys Leu Tyr Leu Leu Tyr Arg Thr Thr His Glu Ser Ser Pro
                245                 250                 255

Asp Arg Asp Arg Ala Pro Val Ala Phe Gly Asp Leu Leu Ala Arg Leu
            260                 265                 270

Pro Arg Tyr Leu Ala Arg Leu Ala Ala Val Ile Gly Asp Glu Ser Gly
        275                 280                 285

Arg Pro Gln Tyr Arg Tyr Arg Asp Asp Lys Leu Pro Lys Ala Gln Phe
    290                 295                 300

Ala Ala Ala Gly Gly Arg Tyr Glu His Gly Ala Leu Ala Thr His Val
305                 310                 315                 320

Val Ile Ala Thr Leu Val Arg His Gly Val Leu Pro Ala Ala Pro Gly
                325                 330                 335

Asp Val Pro Arg Asp Thr Ser Thr Arg Val Asn Pro Asp Asp Val Ala
            340                 345                 350

His Arg Asp Asp Val Asn Arg Ala Ala Ala Phe Leu Ala Arg Gly
        355                 360                 365

His Asn Leu Phe Leu Trp Glu Asp Gln Thr Leu Leu Arg Ala Thr Ala
    370                 375                 380

Asn Thr Ile Thr Ala Leu Ala Val Leu Arg Arg Leu Leu Ala Asn Gly
385                 390                 395                 400

Asn Val Tyr Ala Asp Arg Leu Asp Asn Arg Leu Gln Leu Gly Met Leu
                405                 410                 415
```

```
Ile Pro Gly Ala Val Pro Ala Glu Ala Ile Ala Arg Gly Ala Ser Gly
            420                 425                 430

Leu Asp Ser Gly Ala Ile Lys Ser Gly Asp Asn Asn Leu Glu Ala Leu
        435                 440                 445

Cys Val Asn Tyr Val Leu Pro Leu Tyr Gln Ala Asp Pro Thr Val Glu
    450                 455                 460

Leu Thr Gln Leu Phe Pro Gly Leu Ala Ala Leu Cys Leu Asp Ala Gln
465                 470                 475                 480

Ala Gly Arg Pro Leu Ala Ser Thr Arg Val Val Asp Met Ser Ser
                485                 490                 495

Gly Ala Arg Gln Ala Ala Leu Val Arg Leu Thr Ala Leu Glu Leu Ile
                500                 505                 510

Asn Arg Thr Arg Thr Asn Thr Thr Pro Val Gly Glu Ile Ile Asn Ala
                515                 520                 525

His Asp Ala Leu Gly Ile Gln Tyr Glu Gln Gly Pro Gly Leu Leu Ala
            530                 535                 540

Gln Gln Ala Arg Ile Gly Leu Ala Ser Asn Thr Lys Arg Phe Ala Thr
545                 550                 555                 560

Phe Asn Val Gly Ser Asp Tyr Asp Leu Leu Tyr Phe Leu Cys Leu Gly
                565                 570                 575

Phe Ile Pro Gln Tyr Leu Ser Val Ala
            580                 585

<210> SEQ ID NO 9
<211> LENGTH: 637
<212> TYPE: PRT
<213> ORGANISM: Herpes Simplex Virus 2

<400> SEQUENCE: 9

Met Ala Ser Ala Glu Met Arg Glu Arg Leu Glu Ala Pro Leu Pro Asp
1               5                   10                  15

Arg Ala Val Pro Ile Tyr Val Ala Gly Phe Leu Ala Leu Tyr Asp Ser
                20                  25                  30

Gly Asp Pro Gly Glu Leu Ala Leu Asp Pro Asp Thr Val Arg Ala Ala
            35                  40                  45

Leu Pro Pro Glu Asn Pro Leu Pro Ile Asn Val Asp His Arg Ala Arg
        50                  55                  60

Cys Glu Val Gly Arg Val Leu Ala Val Val Asn Asp Pro Arg Gly Pro
65                  70                  75                  80

Phe Phe Val Gly Leu Ile Ala Cys Val Gln Leu Glu Arg Val Leu Glu
                85                  90                  95

Thr Ala Ala Ser Ala Ala Ile Phe Glu Arg Arg Gly Pro Ala Leu Ser
            100                 105                 110

Arg Glu Glu Arg Leu Leu Tyr Leu Ile Thr Asn Tyr Leu Pro Ser Val
        115                 120                 125

Ser Leu Ser Thr Lys Arg Arg Gly Asp Glu Val Pro Pro Asp Arg Thr
    130                 135                 140

Leu Phe Ala His Val Ala Leu Cys Ala Ile Gly Arg Arg Leu Gly Thr
145                 150                 155                 160

Ile Val Thr Tyr Asp Thr Ser Leu Asp Ala Ala Ile Ala Pro Phe Arg
                165                 170                 175

His Leu Asp Pro Ala Thr Arg Glu Gly Val Arg Arg Glu Ala Ala Glu
            180                 185                 190

Ala Glu Leu Ala Leu Ala Gly Arg Thr Trp Ala Pro Gly Val Glu Ala
        195                 200                 205
```

```
Leu Thr His Thr Leu Leu Ser Thr Ala Val Asn Asn Met Met Leu Arg
    210                 215                 220
Asp Arg Trp Ser Leu Val Ala Glu Arg Arg Gln Ala Gly Ile Ala
225                 230                 235                 240
Gly His Thr Tyr Leu Gln Ala Ser Glu Lys Phe Lys Ile Trp Gly Ala
                245                 250                 255
Glu Ser Ala Pro Ala Pro Glu Arg Gly Tyr Lys Thr Gly Ala Pro Gly
                260                 265                 270
Ala Met Asp Thr Ser Pro Ala Ala Ser Val Pro Ala Pro Gln Val Ala
                275                 280                 285
Val Arg Ala Arg Gln Val Ala Ser Ser Ser Ser Ser Ser Phe Pro
    290                 295                 300
Ala Pro Ala Asp Met Asn Pro Val Ser Ala Ser Gly Ala Pro Ala Pro
305                 310                 315                 320
Pro Pro Pro Gly Asp Gly Ser Tyr Leu Trp Ile Pro Ala Ser His Tyr
                325                 330                 335
Asn Gln Leu Val Thr Gly Gln Ser Ala Pro Arg His Pro Pro Leu Thr
                340                 345                 350
Ala Cys Gly Leu Pro Ala Ala Gly Thr Val Ala Tyr Gly His Pro Gly
                355                 360                 365
Ala Gly Pro Ser Pro His Tyr Pro Pro Pro Ala His Pro Tyr Pro
370                 375                 380
Gly Met Leu Phe Ala Gly Pro Ser Pro Leu Glu Ala Gln Ile Ala Ala
385                 390                 395                 400
Leu Val Gly Ala Ile Ala Ala Asp Arg Gln Ala Gly Gly Leu Pro Ala
                405                 410                 415
Ala Ala Gly Asp His Gly Ile Arg Gly Ser Ala Lys Arg Arg His
                420                 425                 430
Glu Val Glu Gln Pro Glu Tyr Asp Cys Gly Arg Asp Glu Pro Asp Arg
                435                 440                 445
Asp Phe Pro Tyr Tyr Pro Gly Glu Ala Arg Pro Glu Pro Arg Pro Val
    450                 455                 460
Asp Ser Arg Arg Ala Ala Arg Gln Ala Ser Gly Pro His Glu Thr Ile
465                 470                 475                 480
Thr Ala Leu Val Gly Ala Val Thr Ser Leu Gln Gln Glu Leu Ala His
                485                 490                 495
Met Arg Ala Arg Thr His Ala Pro Tyr Gly Pro Tyr Pro Pro Val Gly
                500                 505                 510
Pro Tyr His His Pro His Ala Asp Thr Glu Thr Pro Ala Gln Pro Pro
    515                 520                 525
Arg Tyr Pro Ala Lys Ala Val Tyr Leu Pro Pro His Ile Ala Pro
    530                 535                 540
Pro Gly Pro Pro Leu Ser Gly Ala Val Pro Pro Ser Tyr Pro Pro
545                 550                 555                 560
Val Ala Val Thr Pro Gly Pro Ala Pro Leu His Gln Pro Ser Pro
                565                 570                 575
Ala His Ala His Pro Pro Pro Pro Gly Pro Thr Pro Pro
    580                 585                 590
Ala Ala Ser Leu Pro Gln Pro Glu Ala Pro Gly Ala Glu Ala Gly Ala
                595                 600                 605
```

```
Leu Val Asn Ala Ser Ser Ala Ala His Val Asn Val Asp Thr Ala Arg
    610                 615                 620
Ala Ala Asp Leu Phe Val Ser Gln Met Met Gly Ser Arg
625                 630                 635
```

<210> SEQ ID NO 10
<211> LENGTH: 722
<212> TYPE: PRT
<213> ORGANISM: Herpes Simplex Virus 2

<400> SEQUENCE: 10

```
Met Gln Arg Arg Ala Arg Gly Ala Ser Ser Leu Arg Leu Ala Arg Cys
 1               5                  10                  15
Leu Thr Pro Ala Asn Leu Ile Arg Gly Ala Asn Ala Gly Val Pro Glu
                20                  25                  30
Arg Arg Ile Phe Ala Gly Cys Leu Leu Pro Thr Pro Glu Gly Leu Leu
            35                  40                  45
Ser Ala Ala Val Gly Val Leu Arg Gln Arg Ala Asp Asp Leu Gln Pro
        50                  55                  60
Ala Phe Leu Thr Gly Ala Asp Arg Ser Val Arg Leu Ala Ala Arg His
65                  70                  75                  80
His Asn Thr Val Pro Glu Ser Leu Ile Val Asp Gly Leu Ala Ser Asp
                85                  90                  95
Pro His Tyr Asp Tyr Ile Arg His Tyr Ala Ser Ala Lys Gln Ala
                100                 105                 110
Leu Gly Glu Val Glu Leu Ser Gly Gly Gln Leu Ser Arg Ala Ile Leu
            115                 120                 125
Ala Gln Tyr Trp Lys Tyr Leu Gln Thr Val Val Pro Ser Gly Leu Asp
        130                 135                 140
Ile Pro Asp Asp Pro Ala Gly Asp Cys Asp Pro Ser Leu His Val Leu
145                 150                 155                 160
Leu Arg Pro Thr Leu Leu Pro Lys Leu Leu Val Arg Ala Pro Phe Lys
                165                 170                 175
Ser Gly Ala Ala Ala Lys Tyr Ala Ala Val Ala Gly Leu Arg
                180                 185                 190
Asp Ala Ala His Arg Leu Gln Gln Tyr Met Phe Phe Met Arg Pro Ala
        195                 200                 205
Asp Pro Ser Arg Pro Ser Thr Asp Thr Ala Leu Arg Leu Ser Glu Leu
210                 215                 220
Leu Ala Tyr Val Ser Val Leu Tyr His Trp Ala Ser Trp Met Leu Trp
225                 230                 235                 240
Thr Ala Asp Lys Tyr Val Cys Arg Arg Leu Gly Pro Ala Asp Arg Arg
                245                 250                 255
Phe Val Ala Leu Ser Gly Ser Leu Glu Ala Pro Ala Glu Thr Phe Ala
            260                 265                 270
Arg His Leu Asp Arg Gly Pro Ser Gly Thr Thr Gly Ser Met Gln Cys
        275                 280                 285
Met Ala Leu Arg Ala Ala Val Ser Asp Val Leu Gly His Leu Thr Arg
290                 295                 300
Leu Ala His Leu Trp Glu Thr Gly Lys Arg Ser Gly Gly Thr Tyr Gly
305                 310                 315                 320
Ile Val Asp Ala Ile Val Ser Thr Val Glu Val Leu Ser Ile Val His
                325                 330                 335
His His Ala Gln Tyr Ile Ile Asn Ala Thr Leu Thr Gly Tyr Val Val
                340                 345                 350
```

```
Trp Ala Ser Asp Ser Leu Asn Asn Glu Tyr Leu Thr Ala Ala Val Asp
        355                 360                 365

Ser Gln Glu Arg Phe Cys Arg Thr Ala Ala Pro Leu Phe Pro Thr Met
370                 375                 380

Thr Ala Pro Ser Trp Ala Arg Met Glu Leu Ser Ile Lys Ser Trp Phe
385                 390                 395                 400

Gly Ala Ala Leu Ala Pro Asp Leu Leu Arg Ser Gly Thr Pro Ser Pro
                405                 410                 415

His Tyr Glu Ser Ile Leu Arg Leu Ala Ala Ser Gly Pro Pro Gly Gly
            420                 425                 430

Arg Gly Ala Val Gly Gly Ser Cys Arg Asp Lys Ile Gln Arg Thr Arg
        435                 440                 445

Arg Asp Asn Ala Pro Pro Leu Pro Arg Ala Arg Pro His Ser Thr
450                 455                 460

Pro Ala Ala Pro Arg Arg Cys Arg Arg His Arg Glu Asp Leu Pro Glu
465                 470                 475                 480

Pro Pro His Val Asp Ala Ala Asp Arg Gly Pro Glu Pro Cys Ala Gly
                485                 490                 495

Arg Pro Ala Thr Tyr Tyr Thr His Met Ala Gly Ala Pro Pro Arg Leu
            500                 505                 510

Pro Pro Arg Asn Pro Ala Pro Pro Glu Gln Arg Pro Ala Ala Ala Ala
        515                 520                 525

Arg Pro Leu Ala Ala Gln Arg Glu Ala Ala Gly Val Tyr Asp Ala Val
530                 535                 540

Arg Thr Trp Gly Pro Asp Ala Glu Ala Glu Pro Asp Gln Met Glu Asn
545                 550                 555                 560

Thr Tyr Leu Leu Pro Asp Asp Asp Ala Ala Met Pro Ala Gly Val Gly
                565                 570                 575

Leu Gly Ala Thr Pro Ala Ala Asp Thr Thr Ala Ala Ala Trp Pro
            580                 585                 590

Ala Glu Ser His Ala Pro Arg Ala Pro Ser Glu Asp Ala Asp Ser Ile
        595                 600                 605

Tyr Glu Ser Val Gly Glu Asp Gly Gly Arg Val Tyr Glu Glu Ile Pro
610                 615                 620

Trp Val Arg Val Tyr Glu Asn Ile Cys Pro Arg Arg Arg Leu Ala Gly
625                 630                 635                 640

Gly Ala Ala Leu Pro Gly Asp Ala Pro Asp Ser Pro Tyr Ile Glu Ala
                645                 650                 655

Glu Asn Pro Leu Tyr Asp Trp Gly Gly Ser Ala Leu Phe Ser Pro Arg
            660                 665                 670

Arg Ala Thr Arg Ala Pro Asp Pro Gly Leu Ser Leu Ser Pro Met Pro
        675                 680                 685

Ala Arg Pro Arg Thr Asn Ala Leu Ala Asn Asp Gly Pro Thr Asn Val
690                 695                 700

Ala Ala Leu Ser Ala Leu Leu Thr Lys Leu Lys Arg Gly Arg His Gln
705                 710                 715                 720

Ser His

<210> SEQ ID NO 11
<211> LENGTH: 393
<212> TYPE: PRT
<213> ORGANISM: Herpes Simplex Virus 2
```

<400> SEQUENCE: 11

```
Met Gly Arg Leu Thr Ser Gly Val Gly Thr Ala Ala Leu Leu Val Val
 1               5                  10                  15

Ala Val Gly Leu Arg Val Val Cys Ala Lys Tyr Ala Leu Ala Asp Pro
            20                  25                  30

Ser Leu Lys Met Ala Asp Pro Asn Arg Phe Arg Gly Lys Asn Leu Pro
        35                  40                  45

Val Leu Asp Gln Leu Thr Asp Pro Pro Gly Val Lys Arg Val Tyr His
    50                  55                  60

Ile Gln Pro Ser Leu Glu Asp Pro Phe Gln Pro Ser Ile Pro Ile
 65                  70                  75                  80

Thr Val Tyr Tyr Ala Val Leu Glu Arg Ala Cys Arg Ser Val Leu Leu
                85                  90                  95

His Ala Pro Ser Glu Ala Pro Gln Ile Val Arg Gly Ala Ser Asp Glu
            100                 105                 110

Ala Arg Lys His Thr Tyr Asn Leu Thr Ile Ala Trp Tyr Arg Met Gly
            115                 120                 125

Asp Asn Cys Ala Ile Pro Ile Thr Val Met Glu Tyr Thr Glu Cys Pro
130                 135                 140

Tyr Asn Lys Ser Leu Gly Val Cys Pro Ile Arg Thr Gln Pro Arg Trp
145                 150                 155                 160

Ser Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
            195                 200                 205

Arg Ala Arg Ala Ser Cys Lys Tyr Ala Leu Pro Leu Arg Ile Pro Pro
210                 215                 220

Ala Ala Cys Leu Thr Ser Lys Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255

Ala Leu Tyr Ser Leu Lys Ile Ala Gly Trp His Gly Pro Lys Pro Pro
            260                 265                 270

Tyr Thr Ser Thr Leu Leu Pro Pro Glu Leu Ser Asp Thr Thr Asn Ala
            275                 280                 285

Thr Gln Pro Glu Leu Val Pro Glu Asp Pro Glu Asp Ser Ala Leu Leu
        290                 295                 300

Glu Asp Pro Ala Gly Thr Val Ser Ser Gln Ile Pro Pro Asn Trp His
305                 310                 315                 320

Ile Pro Ser Ile Gln Asp Val Ala Pro His His Ala Pro Ala Ala Pro
                325                 330                 335

Ser Asn Pro Gly Leu Ile Ile Gly Ala Leu Ala Gly Ser Thr Leu Ala
            340                 345                 350

Val Leu Val Ile Gly Gly Ile Ala Phe Trp Val Arg Arg Arg Ala Gln
            355                 360                 365

Met Ala Pro Lys Arg Leu Arg Leu Pro His Ile Arg Asp Asp Asp Ala
        370                 375                 380

Pro Pro Ser His Gln Pro Leu Phe Tyr
385                 390
```

<210> SEQ ID NO 12
<211> LENGTH: 545
<212> TYPE: PRT
<213> ORGANISM: Herpes Simplex Virus 2

<400> SEQUENCE: 12

```
Met Ala Arg Gly Ala Gly Leu Val Phe Phe Val Gly Val Trp Val Val
 1               5                  10                  15

Ser Cys Leu Ala Ala Pro Arg Thr Ser Trp Lys Arg Val Thr Ser
            20                  25                  30

Gly Glu Asp Val Val Leu Leu Pro Ala Pro Ala Glu Arg Thr Arg Ala
            35                  40                  45

His Lys Leu Leu Trp Ala Ala Glu Pro Leu Asp Ala Cys Gly Pro Leu
        50                  55                  60

Arg Pro Ser Trp Val Ala Leu Trp Pro Pro Arg Val Leu Glu Thr
65                  70                  75                  80

Val Val Asp Ala Ala Cys Met Arg Ala Pro Glu Pro Leu Ala Ile Ala
                85                  90                  95

Tyr Ser Pro Pro Phe Pro Ala Gly Asp Glu Gly Leu Tyr Ser Glu Leu
            100                 105                 110

Ala Trp Arg Asp Arg Val Ala Val Asn Glu Ser Leu Val Ile Tyr
        115                 120                 125

Gly Ala Leu Glu Thr Asp Ser Gly Leu Tyr Thr Leu Ser Val Val Gly
    130                 135                 140

Leu Ser Asp Glu Ala Arg Gln Val Ala Ser Val Val Leu Val Val Glu
145                 150                 155                 160

Pro Ala Pro Val Pro Thr Pro Thr Pro Asp Asp Tyr Asp Glu Glu Asp
                165                 170                 175

Asp Ala Gly Val Thr Asn Ala Arg Arg Ser Ala Phe Pro Pro Gln Pro
            180                 185                 190

Pro Pro Arg Arg Pro Pro Val Ala Pro Pro Thr His Pro Arg Val Ile
        195                 200                 205

Pro Glu Val Ser His Val Arg Gly Val Thr Val His Met Glu Thr Leu
    210                 215                 220

Glu Ala Ile Leu Phe Ala Pro Gly Glu Thr Phe Gly Thr Asn Val Ser
225                 230                 235                 240

Ile His Ala Ile Ala His Asp Asp Gly Pro Tyr Ala Met Asp Val Val
                245                 250                 255

Trp Met Arg Phe Asp Val Pro Ser Ser Cys Ala Asp Met Arg Ile Tyr
            260                 265                 270

Glu Ala Cys Leu Tyr His Pro Gln Leu Pro Glu Cys Leu Ser Pro Ala
        275                 280                 285

Asp Ala Pro Cys Ala Val Ser Ser Trp Ala Tyr Arg Leu Ala Val Arg
    290                 295                 300

Ser Tyr Ala Gly Cys Ser Arg Thr Thr Pro Pro Arg Cys Phe Ala
305                 310                 315                 320

Glu Ala Arg Met Glu Pro Val Pro Gly Leu Ala Trp Leu Ala Ser Thr
                325                 330                 335

Val Asn Leu Glu Phe Gln His Ala Ser Pro Gln His Ala Gly Leu Tyr
            340                 345                 350

Leu Cys Val Val Tyr Val Asp Asp His Ile His Ala Trp Gly His Met
        355                 360                 365

Thr Ile Ser Thr Ala Ala Gln Tyr Arg Asn Ala Val Val Glu Gln His
    370                 375                 380
```

```
Leu Pro Gln Arg Gln Pro Glu Pro Val Glu Pro Thr Arg Pro His Val
385                 390                 395                 400

Arg Ala Pro His Pro Ala Pro Ser Ala Arg Gly Pro Leu Arg Leu Gly
            405                 410                 415

Ala Val Leu Gly Ala Ala Leu Leu Leu Ala Ala Leu Gly Leu Ser Ala
            420                 425                 430

Trp Ala Cys Met Thr Cys Trp Arg Arg Ser Trp Arg Ala Val Lys
            435                 440                 445

Ser Arg Ala Ser Ala Thr Gly Pro Thr Tyr Ile Arg Val Ala Asp Ser
    450                 455                 460

Glu Leu Tyr Ala Asp Trp Ser Ser Asp Ser Glu Gly Arg Asp Gly
465                 470                 475                 480

Ser Leu Trp Gln Asp Pro Pro Glu Arg Pro Asp Ser Pro Ser Thr Asn
                485                 490                 495

Gly Ser Gly Phe Glu Ile Leu Ser Pro Thr Ala Pro Ser Val Tyr Pro
            500                 505                 510

His Ser Glu Gly Arg Lys Ser Arg Arg Pro Leu Thr Thr Phe Gly Ser
            515                 520                 525

Gly Ser Pro Gly Arg Arg His Ser Gln Ala Ser Tyr Pro Ser Val Leu
    530                 535                 540

Trp
545

<210> SEQ ID NO 13
<211> LENGTH: 9
<212> TYPE: PRT
<213> ORGANISM: Cytomegalovirus

<400> SEQUENCE: 13

Asn Leu Val Pro Met Val Ala Thr Val
  1               5

<210> SEQ ID NO 14
<211> LENGTH: 29
<212> TYPE: DNA
<213> ORGANISM: Artificial Sequence
<220> FEATURE:
<223> OTHER INFORMATION: Primer

<400> SEQUENCE: 14
gacgctagcc acgaccgtct ggaggtact                                    29

<210> SEQ ID NO 15
<211> LENGTH: 29
<212> TYPE: DNA
<213> ORGANISM: Artificial Sequence
<220> FEATURE:
<223> OTHER INFORMATION: Primer

<400> SEQUENCE: 15
gactctagag cgaccgttac cctgaaata                                    29

<210> SEQ ID NO 16
<211> LENGTH: 27
<212> TYPE: DNA
<213> ORGANISM: Artificial Sequence
<220> FEATURE:
<223> OTHER INFORMATION: Primer

<400> SEQUENCE: 16
gactctagag acgaggaaag gggtggt                                      27
```

```
<210> SEQ ID NO 17
<211> LENGTH: 29
<212> TYPE: DNA
<213> ORGANISM: Artificial Sequence
<220> FEATURE:
<223> OTHER INFORMATION: Primer

<400> SEQUENCE: 17
gacaagcttc cgctcctctg ggtacttta                                      29
```